United States Patent
Cottrell et al.

(10) Patent No.: US 8,344,153 B2
(45) Date of Patent: Jan. 1, 2013

(54) INHIBITORS OF PHOSPHATIDYLINOSITOL 3-KINASE

(75) Inventors: Kevin Michael Cottrell, Cambridge, MA (US); Alex Aronov, Newton, MA (US); Robert J. Davies, Watertown, MA (US); Jon H. Come, Cambridge, MA (US); David Messersmith, Somerville, MA (US); Jinwang Xu, Framingham, MA (US); Upul Keerthi Bandarage, Lexington, MA (US); Jingrong Cao, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 392 days.

(21) Appl. No.: 12/796,825

(22) Filed: Jun. 9, 2010

(65) Prior Publication Data

US 2010/0316605 A1  Dec. 16, 2010

Related U.S. Application Data

(60) Provisional application No. 61/185,674, filed on Jun. 10, 2009.

(51) Int. Cl.
*A61K 31/425* (2006.01)
*C07D 277/00* (2006.01)
(52) U.S. Cl. .......................................... 548/195; 514/371
(58) Field of Classification Search .................. 548/195; 514/371
See application file for complete search history.

(56) References Cited

FOREIGN PATENT DOCUMENTS

WO  2008/027584 A2  3/2008

*Primary Examiner* — Janet Andres
*Assistant Examiner* — John Mabry
(74) *Attorney, Agent, or Firm* — Daniel A. Pearson

(57) ABSTRACT

The present invention relates to compounds useful as inhibitors of PI3K, particularly of PI3Kγ. The invention also provides pharmaceutically acceptable compositions comprising said compounds and methods of using the compositions in the treatment of various disease, conditions, or disorders.

16 Claims, No Drawings

INHIBITORS OF PHOSPHATIDYLINOSITOL 3-KINASE

This present application claims the benefit, under 35 U.S.C. §119, to U.S. Provisional Application No. 61/185,674, filed Jun. 10, 2009 the entire disclosure of which is incorporated herein by reference.

TECHNICAL FIELD OF THE INVENTION

The present invention relates to compounds useful as inhibitors of phosphatidylinositol 3-kinase (PI3K). The invention also provides pharmaceutically acceptable compositions comprising the compounds of the invention and methods of using the compositions in the treatment of various disorders.

BACKGROUND OF THE INVENTION

PI3Ks are a family of lipid kinases that catalyze the phosphorylation of the membrane lipid phosphatidylinositol (PI) on the 3'-OH of the inositol ring to produce PI 3-phosphate [PI(3)P, PIP], PI 3,4-bisphosphate [PI(3,4)$P_2$, PIP2] and PI 3,4,5-trisphosphate [PI(3,4,5)$P_3$, PIP3]. PI(3,4)$P_2$ and PI(3,4,5)$P_3$ act as recruitment sites for various intracellular signaling proteins, which in turn form signaling complexes to relay extracellular signals to the cytoplasmic face of the plasma membrane.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain-containing p85 adapter subunit. Class Ia PI3Ks are activated through tyrosine kinase signaling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p101 regulatory subunit. PI3Kγ is regulated by G protein-coupled receptors (GPCRs) via association with βγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

Although a number of PI3K inhibitors have been developed, there is a need for additional compounds to inhibit PI3Ks for treating various disorders and diseases, especially those affecting the central nervous system (CNS). Accordingly, it would be desirable to develop additional compounds that are useful as inhibitors of PI3K that penetrate the blood-brain barrier (BBB).

SUMMARY OF THE INVENTION

It has been found that compounds of this invention, and pharmaceutically acceptable compositions thereof, are effective as inhibitors of PI3K, particularly PI3Kγ. Accordingly, the invention features compounds having the general formula:

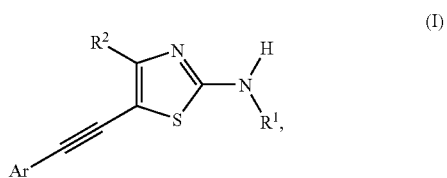

or a pharmaceutically acceptable salt thereof, where each of $R^1$, $R^2$, and Ar is as defined herein.

The invention also provides pharmaceutical compositions that include a compound of formula I and a pharmaceutically acceptable carrier, adjuvant, or vehicle. These compounds and pharmaceutical compositions are useful for treating or lessening the severity of a variety of disorders, including autoimmune diseases and inflammatory diseases of the CNS.

The compounds and compositions provided by this invention are also useful for the study of PI3K in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 3 to 7 ring members. The term "aryl" may be used interchangeably with the term "aryl ring." Examples of aryl rings include phenyl, naphthyl, and anthracene.

The term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 3 to 7 ring members. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl, and the like) or heteroaryl (including heteroaralkyl, heteroarylalkoxy, and the like) group may contain one or more substituents. Suitable substituents on the unsaturated carbon atom of an aryl or heteroaryl group include: halogen; $C_{1-4}$aliphatic, —OH; —OR°; —SH°; —SR°; 1,2-methylenedioxy; 1,2-ethylenedioxy; phenyl (Ph); —O(Ph); —(CH$_2$)$_{1-2}$(Ph); —CH=CH(Ph); —NO$_2$; —CN; —NH$_2$; —NH(R°); —N(R°)$_2$; —NHC(O)R°; —NR°C(O)R°; —NHC(S)R°; —NR°C(S)R°; —NHC(O)NH$_2$; —NHC(O)NH(R°); —NHC(O)N(R°)$_2$; —NR°C(O)NH(R°); —NR°C(O)N(R°)$_2$; —NHC(S)NH$_2$; —NHC(S)N(R°)$_2$; —NHC(S)NH(R°); —NR°C(S)NH(R°); —NR°C(S)N(R°)$_2$; —NHC(O)OR°; —NR°C(O)OR°; —C(O)OH; —C(O)OR°; —C(O)R°; —C(S)R°; —C(O)NH$_2$; —C(O)NH(R°); —C(O)N(R°)$_2$; —C(S)NH$_2$; —C(S)NH(R°); —C(S)N(R°)$_2$; —OC(O)NH$_2$; —OC(O)NH(R°); —OC(O)N(R°)$_2$; —OC(O)R°; —C(NOR°)H; —C(NOR°)R°; —S(O)$_2$R°; —S(O)$_3$R°; —S(O)$_3$H; —S(O)$_2$NH$_2$; —S(O)$_2$NH(R°); —S(O)$_2$N(R°)$_2$; —S(O)R°; —NHS(O)$_2$R°; —NR°S(O)$_2$R°; —N(OR°)R°; —(CH$_2$)$_{0-2}$NHC(O)R°; -L-R°; -L-N(R°)$_2$); -L-SR°; -L-OR°; -L-(C$_{3-10}$ cycloaliphatic), -L-(C$_{6-10}$ aryl), -L-(5-10 membered heteroaryl), -L-(5-10 membered heterocyclyl), oxo, $C_{1-4}$ haloalkoxy, $C_{1-4}$ haloalkyl, -L-NO$_2$, -L-CN, -L-OH, -L-CF$_3$; or two substituents, on the same carbon or on different carbons, together with the carbon or intervening carbons to which they are bound, form a 5-7 membered saturated, unsaturated, or partially saturated ring, wherein L is a $C_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each occurrence of R° is independently selected from optionally substituted $C_{1-6}$ aliphatic, an unsubstituted 5 to 6 membered heteroaryl or heterocyclic ring, phenyl, or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Optional substituents on the aliphatic group of R° include —NH$_2$, —NH(C$_{1-4}$ aliphatic), —N(C$_{1-4}$ aliphatic)$_2$, halogen, $C_{1-4}$ aliphatic, —OH, —O(C$_{1-4}$ aliphatic), —NO$_2$, —CN, —C(O)OH, —C(O)O(C$_{1-4}$ aliphatic), —O(haloC$_{1-4}$ aliphatic), or haloC$_{1-4}$ aliphatic, wherein each of the foregoing $C_{1-4}$ aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHC(O)O(alkyl), =NNHS(O)$_2$(alkyl), or =NR*, where each R* is independently selected from hydrogen or an optionally substituted $C_{1-8}$ aliphatic. Optional substituents on the aliphatic group of R* are selected from —NH$_2$, —NH(C$_{1-4}$ aliphatic), —N(C$_{1-4}$ aliphatic)$_2$, halogen, $C_{1-4}$ aliphatic, —OH, —O(C$_{1-4}$ aliphatic), —NO$_2$, —CN, —C(O)OH, —C(O)O(C$_{1-4}$ aliphatic), —C(O)NH$_2$, —C(O)NH(C$_{1-4}$ aliphatic), —C(O)N(C$_{1-4}$ aliphatic)$_2$, —O(halo-C$_{1-4}$ aliphatic), and halo(C$_{1-4}$ aliphatic), where each of the foregoing $C_{1-4}$ aliphatic groups of R* is unsubstituted; or two R* on the same nitrogen are taken together with the nitrogen to form a 5-8 membered heterocyclyl or heteroaryl ring having 1-3 heteroatoms independently selected from nitrogen, oxygen, and sulfur.

In some embodiments, optional substituents on the nitrogen of a non-aromatic heterocyclic ring include —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(=S)N(R$^+$)$_2$, —C(=NH)—N(R$^+$)$_2$, or —NR$^+$S(O)$_2$R$^+$; wherein R$^+$ is hydrogen, an optionally substituted $C_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from —NH$_2$, —NH(C$_{1-4}$ aliphatic), —N(C$_{1-4}$ aliphatic)$_2$, halogen, $C_{1-4}$ aliphatic, —OH, —O(C$_{1-4}$ aliphatic), —NO$_2$, —CN, —C(O)OH, —C(O)O(C$_{1-4}$ aliphatic), —O(halo(C$_{1-4}$ aliphatic)), or halo(C$_{1-4}$ aliphatic), wherein each of the foregoing $C_{1-4}$aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

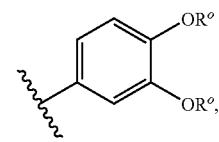

these two occurrences of R° are taken together with the oxygen atoms to which they are bound to form a fused 6-membered oxygen containing ring:

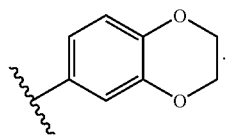 [SMILES: *c1ccc2c(c1)OCCO2]

It will be appreciated that a variety of other rings can be formed when two independent occurrences of R° (or R+, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NR°—, —OC(O)NH—, —OC(O)NR°—, —NHS(O)$_2$NH—, —NR°S(O)$_2$NR°—, —S(O)—, or —S(O)$_2$—, wherein R° is defined elsewhere herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH$_2$CH$_2$CH$_3$ was optionally replaced with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below) represents substitution of the substituent at any substitutable position in any of the rings within the multiple ring system. For example, Structure a represents possible substitution in any of the positions shown in Structure b.

Structure a

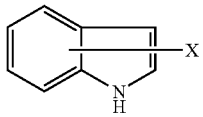

Structure b

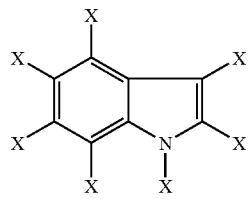

This also applies to multiple ring systems fused to optional ring systems (which would be represented by dotted lines). For example, in Structure c, X is an optional substituent both for ring A and ring B.

Structure c

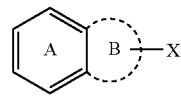

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

Structure d

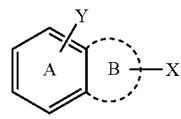

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I or a compound listed in Table 1. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in biological assays, or as PI3K inhibitors with improved therapeutic profile.

Description of Compounds of the Invention

In one aspect, the invention features compounds having formula I:

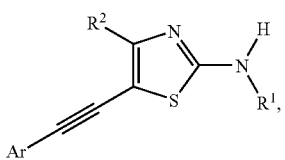

(I)

or a pharmaceutically acceptable salt thereof, wherein:
Ar is a phenyl ring or a 5-10 membered monocyclic or fused bicyclic heteroaryl ring having up to 2 atoms selected from nitrogen, wherein each ring is optionally substituted with up to 3 substituents independently selected from fluoro, chloro, $C_{1-4}$aliphatic, $C_{3-4}$cycloaliphatic, —$OC_{1-4}$aliphatic, —$OC_{3-4}$cycloaliphatic, —N($J^{R1}$)C(O)C$_{1-4}$aliphatic, or N($J^{R1}$)$_2$, wherein each of said aliphatic or cycloaliphatic is optionally substituted with up to 3 occurrences of fluoro;

$R^1$ is selected from —C(O)$R^{1a}$, —C(O)O$R^{1a}$, or —C(O)N($R^{1a}$)($R^{1b}$) wherein $R^{1a}$ is $C_{1-4}$ aliphatic, $C_{3-6}$ cycloaliphatic, or $C_{5-10}$ heterocyclic having up to 2 atoms selected from oxygen, sulfur, or nitrogen, wherein $R^{1a}$ is optionally substituted with 1, 2, 3, or 4, occurrences of $J^R$;

each $J^R$ is independently fluoro, oxo, —C(O)$J^{R1}$, —C(O)N($J^{R1}$)$_2$, —C(O)O($J^{R1}$), —N($J^{R1}$)C(O)$J^{R1}$, —O$J^{R1}$, —S$J^{R1}$, —S(O)$J^{R1}$, phenyl or a 5-10 membered heteroaryl or heterocyclyl ring having up to 2 atoms selected from nitrogen, oxygen, or sulfur, wherein said phenyl, heteroaryl, or heterocyclyl is optionally substituted with 1 or 2 $J^{R2}$ groups;

$R^{1b}$ is, independently, hydrogen, $C_{1-4}$aliphatic, $C_{3-6}$cycloaliphatic; or $R^{1a}$ and $R^{1b}$, together with the nitrogen to which they are attached, form a 4-6 membered heterocyclic ring, wherein said heterocyclic ring optionally comprises one additional heteroatom selected from nitrogen and oxygen, and wherein said heterocyclic ring is optionally substituted with 1 or 2 $J^{R2}$ groups;

$R^2$ is $C_{1-4}$aliphatic optionally substituted with 1, 2, or 3 $J^{R2}$ groups;

each $J^{R1}$ is independently selected from hydrogen, $C_{1-4}$aliphatic, $C_{3-6}$cycloaliphatic, phenyl, benzyl, or 5-6 membered heteroaryl ring having up to two atom selected from nitrogen, oxygen, or sulfur, wherein each of said $C_{1-4}$aliphatic, phenyl, benzyl, or heteroaryl is optionally substituted with up to three $J^{R2}$ groups; and each $J^{R2}$ is, independently, selected from chloro, fluoro, —CN, —NO$_2$, oxo, $C_{1-4}$alkyl, $C_{3-6}$cycloalkyl, —OH, —OC$_{1-4}$alkyl, —OPhenyl, or —OCH$_2$Phenyl, wherein each of said alkyl, cycloalkyl or phenyl is optionally substituted with up to 3 fluoro groups.

In one embodiment, the invention features compounds having formula II:

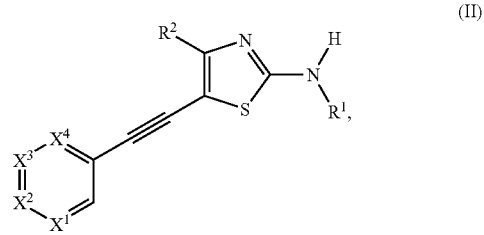

(II)

or a pharmaceutically acceptable salt thereof, wherein:
each of $X^1$, $X^2$, $X^3$, and $X^4$ is N or C$R^3$, where no more than two of $X^1$, $X^2$, $X^3$, and $X^4$ can be N;
$R^1$ is selected from —C(O)$R^{1a}$ or —C(O)N($R^{1a}$)($R^{1b}$);
$R^{1a}$ is $C_{1-4}$ aliphatic or $C_{3-6}$ cycloaliphatic, wherein $R^{1a}$ is optionally substituted with 1, 2, 3, or 4, occurrences of $J^R$;
each $J^R$ is independently fluoro, —C(O)$J^{R1}$, —C(O)N($J^{R1}$)$_2$, —C(O)O($J^{R1}$), —N($J^{R1}$)C(O)$J^{R1}$, —O$J^{R1}$, —S$J^{R1}$, phenyl or a 5-6 membered heteroaryl or heterocyclyl ring having up to 2 atoms selected from nitrogen, oxygen, or sulfur, wherein said phenyl, heteroaryl, or heterocyclyl is optionally substituted with 1 or 2 $J^{R2}$ groups;
each $R^{1b}$ is, independently, hydrogen, $C_{1-4}$aliphatic, $C_{3-6}$cycloaliphatic; or
$R^{1a}$ and $R^{1b}$, together with the nitrogen to which they are attached, form a 4-6 membered heterocyclic ring, wherein said heterocyclic ring optionally comprises one additional heteroatom selected from nitrogen and oxygen, and wherein said heterocyclic ring is optionally substituted with 1 or 2 $J^{R2}$ groups;
$R^2$ is $C_{1-4}$aliphatic or $C_{3-4}$ cycloaliphatic, wherein said aliphatic or cycloaliphatic is optionally substituted with 1, 2, or 3 $J^{R2}$ groups;
$R^3$ is hydrogen, fluoro, chloro, —CN, $C_{1-4}$aliphatic, $C_{3-4}$cycloaliphatic, —OC$_{1-4}$aliphatic, —OC$_{3-4}$cycloaliphatic, or N($J^{R1}$)$_2$, wherein each of said $C_{1-4}$aliphatic, $C_{3-4}$cycloaliphatic, —OC$_{1-4}$aliphatic, or —OC$_{3-4}$ cycloaliphatic is optionally substituted with up to 3 occurrences of fluoro;

each $J^{R1}$ is independently selected from hydrogen, $C_{1-4}$aliphatic, $C_{3-6}$cycloaliphatic, phenyl, benzyl, wherein each of said $C_{1-4}$aliphatic, phenyl, or benzyl is optionally substituted with up to three $J^{R2}$ groups; and each $J^{R2}$ is, independently, selected from chloro, fluoro, —CN, —NO$_2$, oxo, $C_{1-4}$alkyl, $C_{3-6}$cycloaliphatic, —OH, or —OC$_{1-4}$alkyl.

In another embodiment of compounds of formula I, Ar is an optionally substituted 5-10 membered heteroaryl ring. In a further embodiment, Ar is an optionally substituted group selected from:

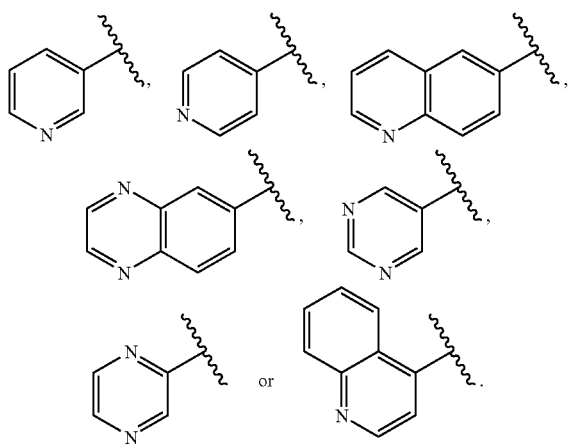

In another further embodiment, Ar is substituted with 1 to 2 groups independently selected from —OCH$_3$, —OCF$_3$, —OCHF$_2$, Cl, F, or CF$_3$.

In one embodiment, $R^2$ is methyl.

In one embodiment, $R^1$ is —C(O)N($R^{1a}$)($R^{1b}$). In a further embodiment, $R^{1b}$ is hydrogen.

In one embodiment, $R^{1a}$ is —CH$_2$CH(R)-$J^R$, wherein R is hydrogen or methyl and $J^R$ is —O$J^{R1}$ or a 5-membered heteroaryl ring having 2 nitrogen atoms, said heteroaryl ring substituted with $C_{1-3}$alkyl or cyclopropyl, each of said alkyl and cyclopropyl optionally substituted with up to 3 fluoro groups.

In a further embodiment, $J^R$ is

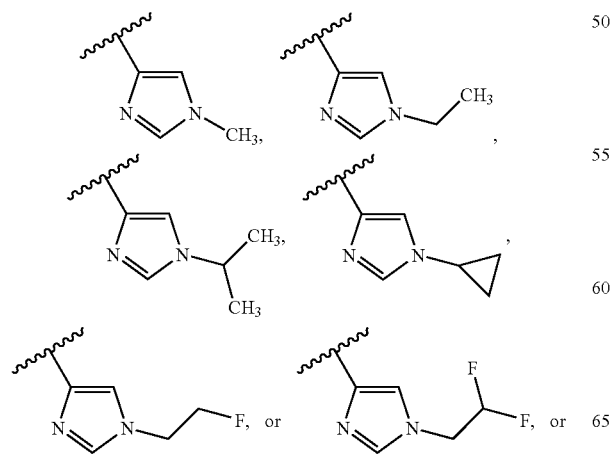

-continued

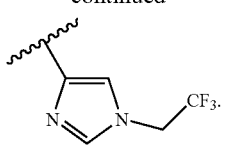

In another embodiment, $J^R$ is —O$J^{R1}$ and $J^{R1}$ is $C_{1-4}$alkyl, optionally substituted with cyclopropyl or up to three fluoro or methyl groups. In a further embodiment, $J^{R1}$ is —CH$_2$-cyclopropyl.

In another embodiment, $J^R$ is —O$J^{R1}$ and $J^{R1}$ is phenyl or pyridyl, optionally substituted with up to three fluoro groups.

In another embodiment, the invention features a compound selected from the group of compounds listed in Table 1.

TABLE 1

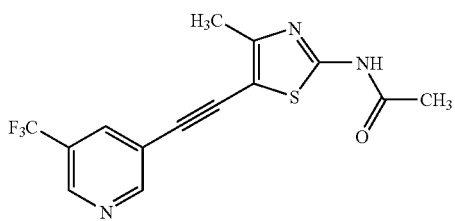

1

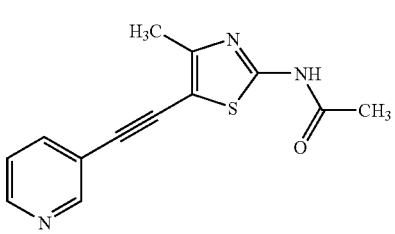

2

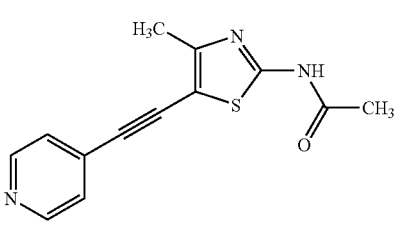

3

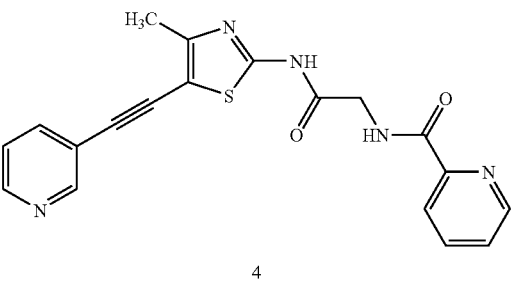 [SMILES: Cc1nc(NC(=O)CNC(=O)c2ccccn2)sc1C#Cc1cccnc1]

4

TABLE 1-continued
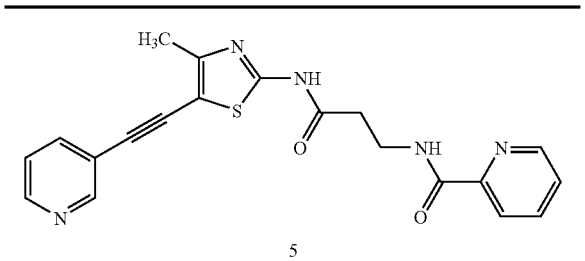
5
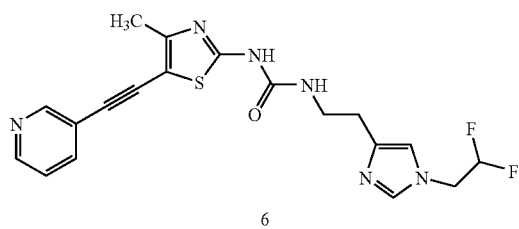 [SMILES: Cc1nc(NC(=O)NCCc2cn(CC(F)F)cn2)sc1C#Cc1cccnc1]
6
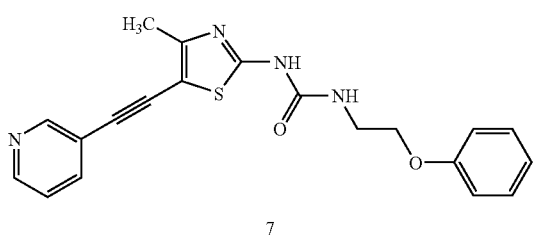 [SMILES: Cc1nc(NC(=O)NCCOc2ccccc2)sc1C#Cc1cccnc1]
7
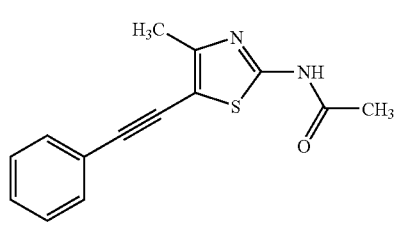
8
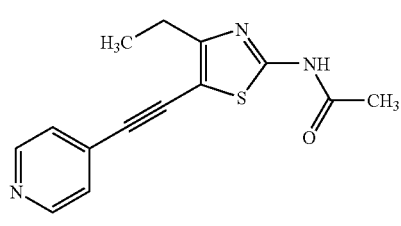
9
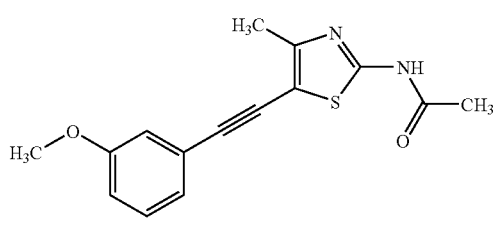
10
TABLE 1-continued
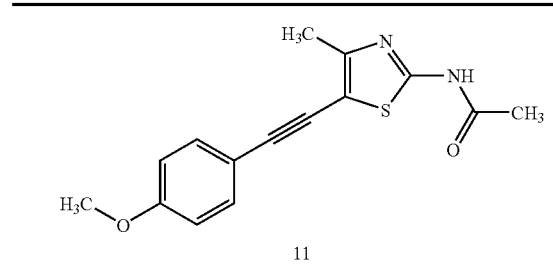
11
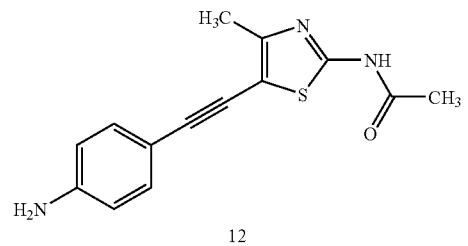 [SMILES: CC(=O)Nc1nc(C)c(C#Cc2ccc(N)cc2)s1]
12
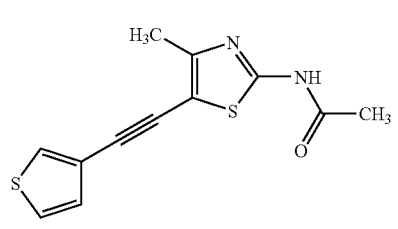
13
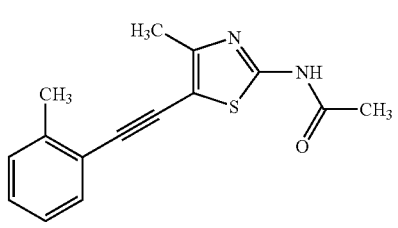
14
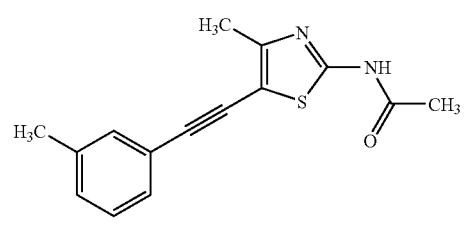
15
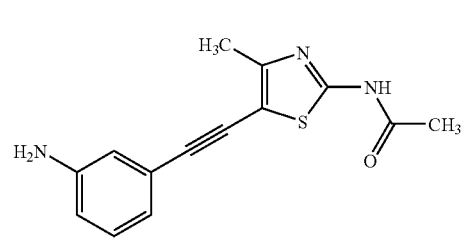
16

TABLE 1-continued
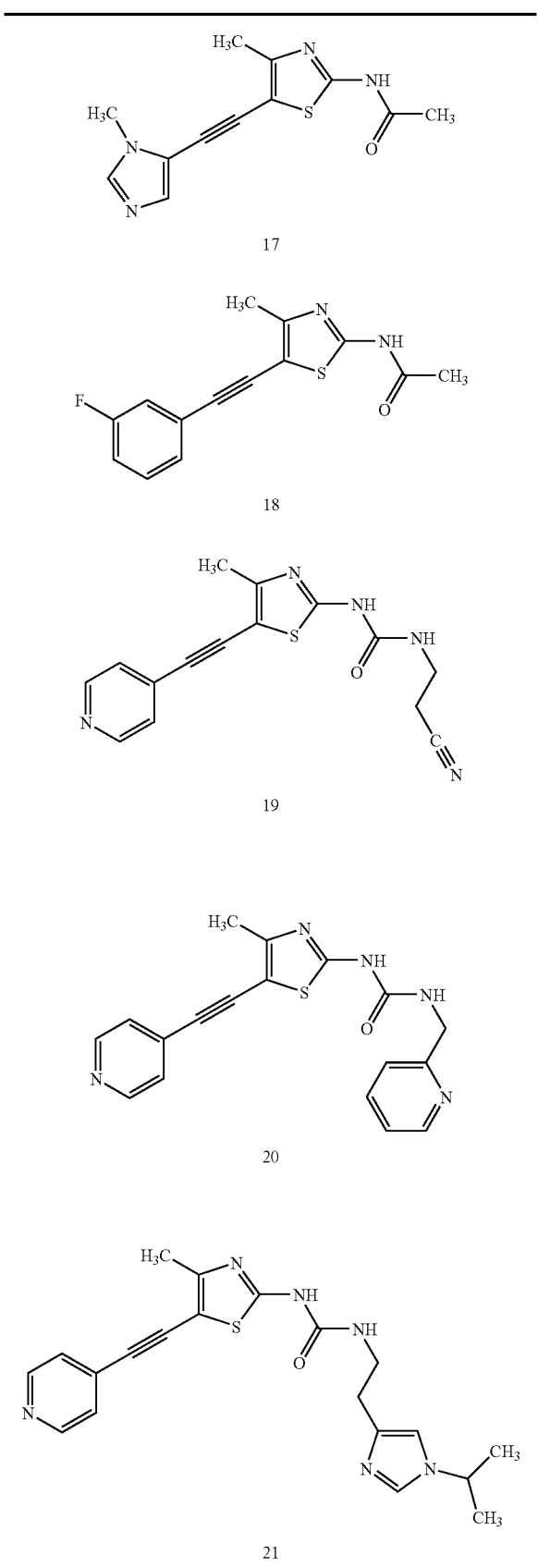
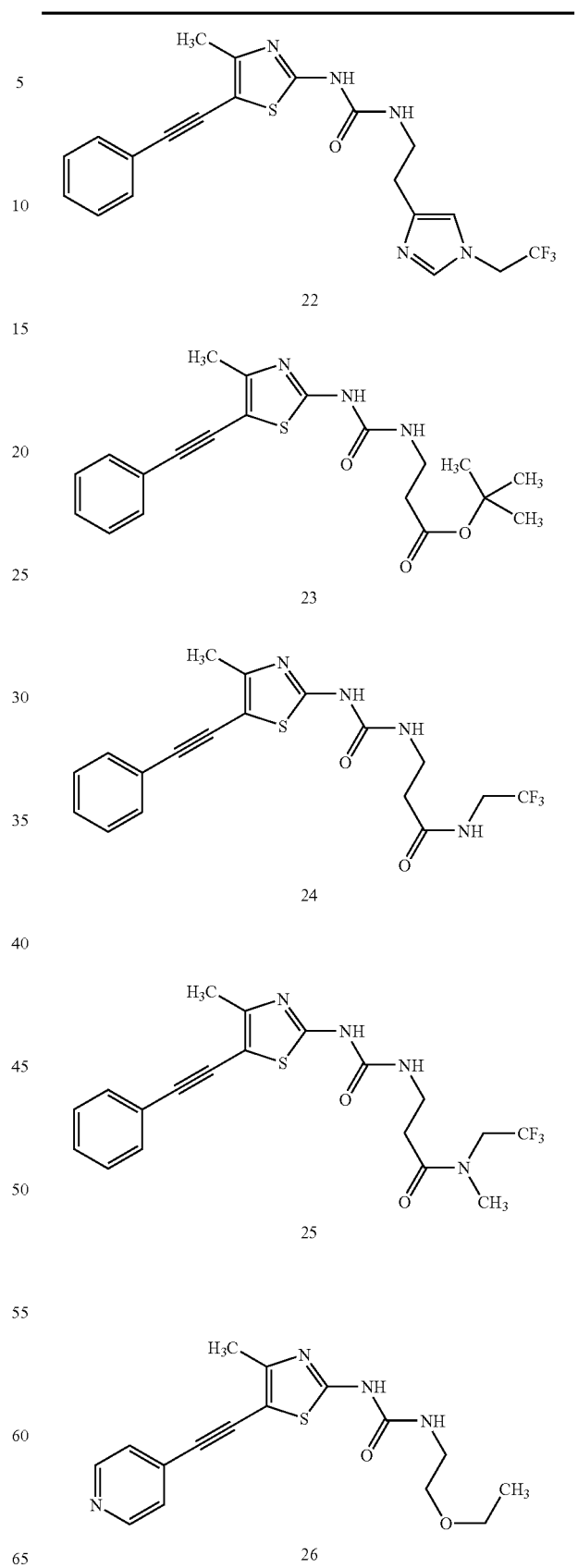

TABLE 1-continued
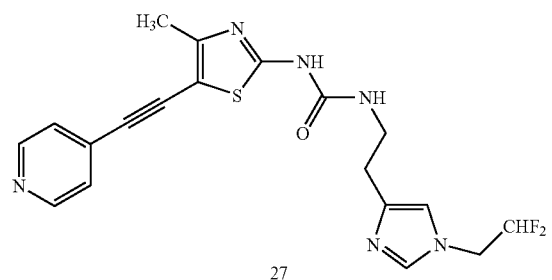 [SMILES: Cc1nc(NC(=O)NCCc2cn(CC(F)F)cn2)sc1C#Cc1ccncc1]
27
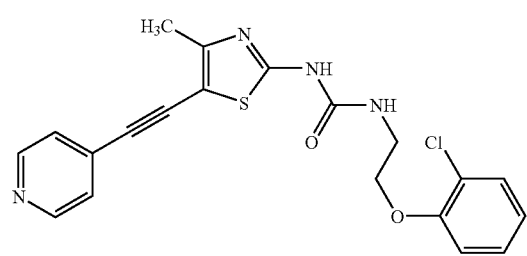
28
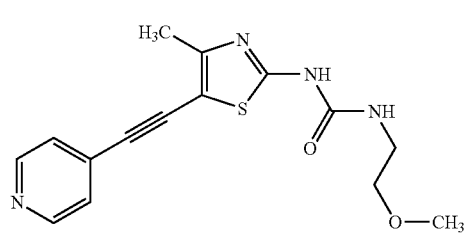
29
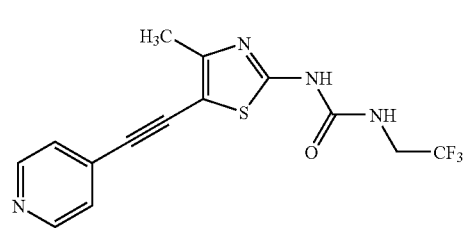
30
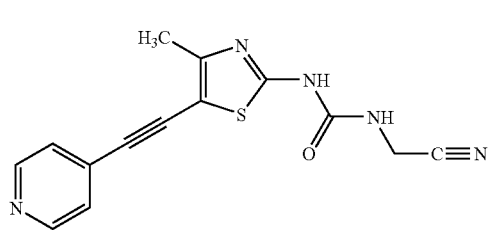
31
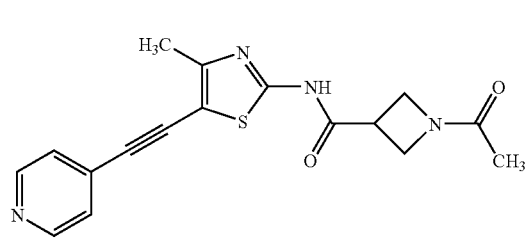
32
TABLE 1-continued
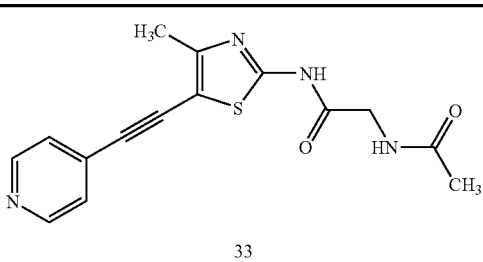
33
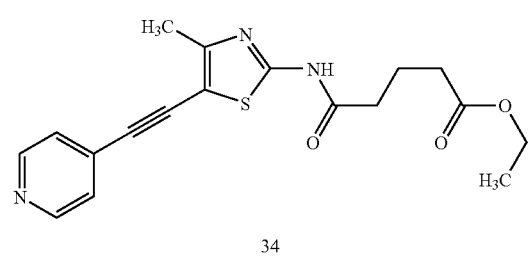 [SMILES: CCOC(=O)CCCC(=O)Nc1nc(C)c(C#Cc2ccncc2)s1]
34
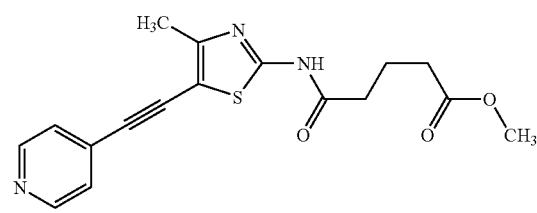
35
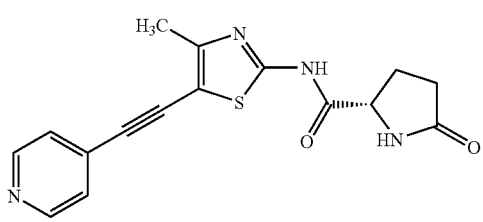
36
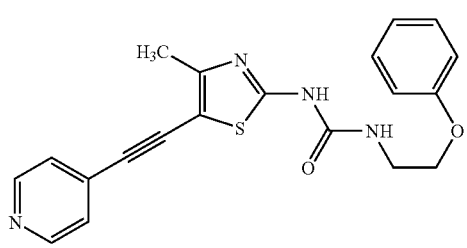
37
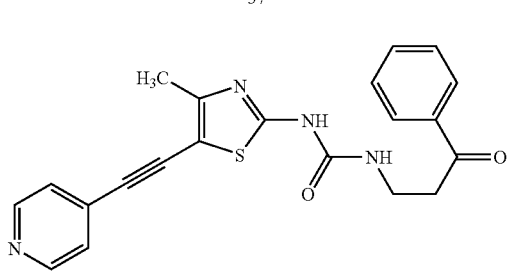
38

TABLE 1-continued
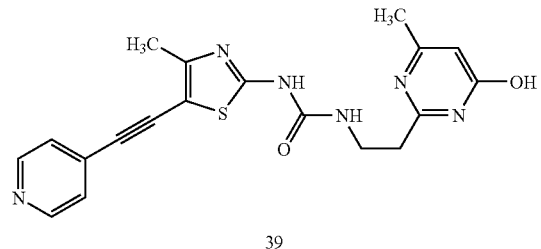 [SMILES: Cc1cc(O)nc(CCNC(=O)Nc2nc(C)c(C#Cc3ccncc3)s2)n1]
39
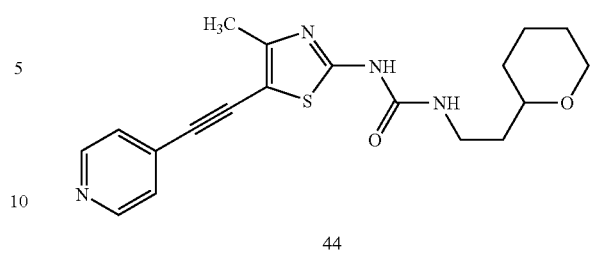
44
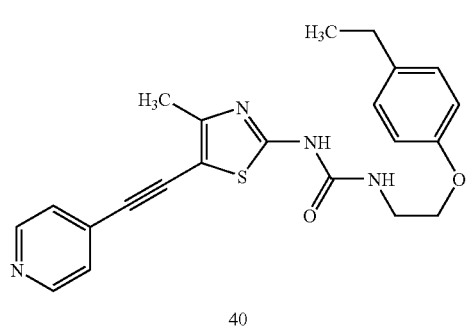 [SMILES: COc1ccc(OCCNC(=O)Nc2nc(C)c(C#Cc3ccncc3)s2)cc1]
40
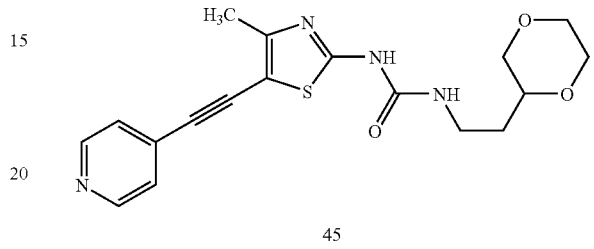
45
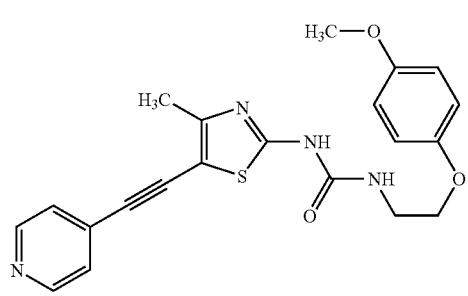
41
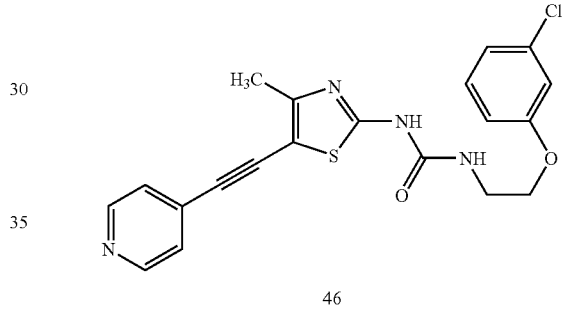
46
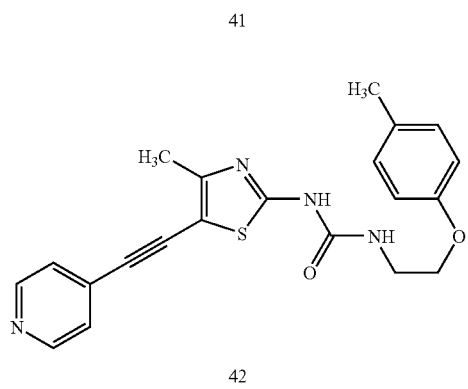
42
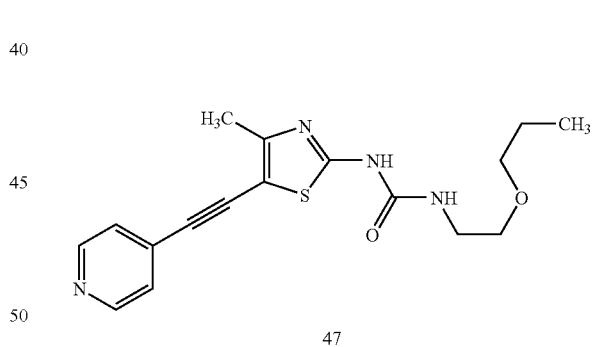
47
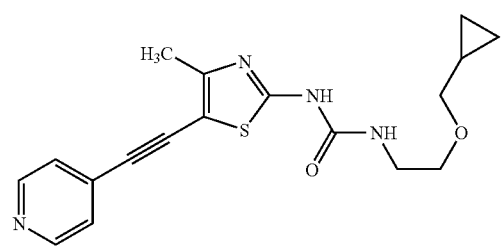
43
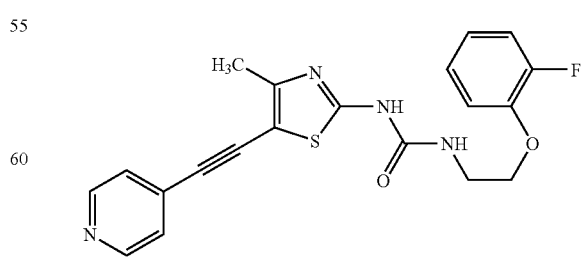
48

TABLE 1-continued
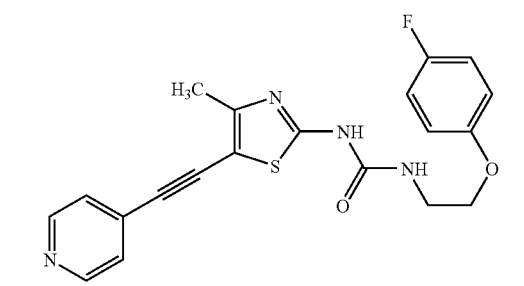
49
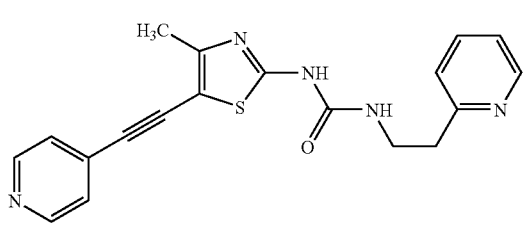
50
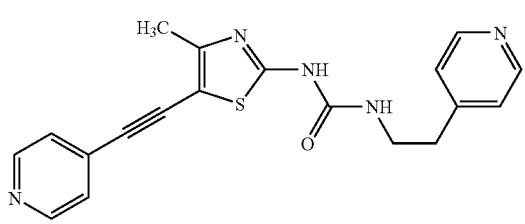
51
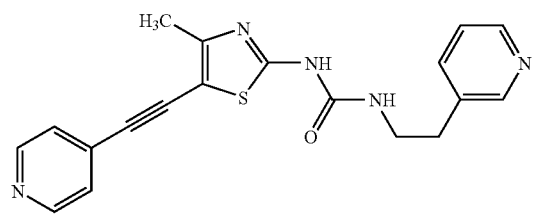
52
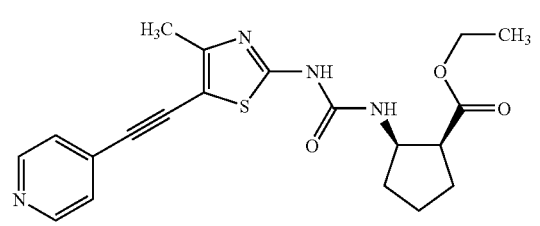
53
TABLE 1-continued
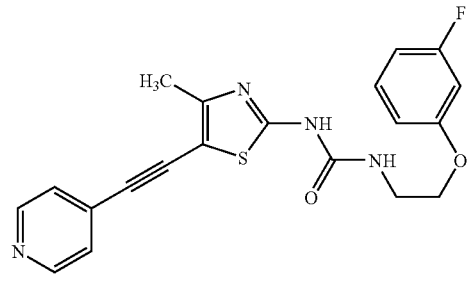
54
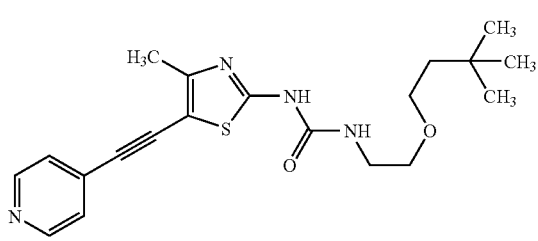
55
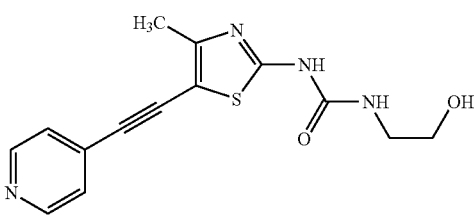
56
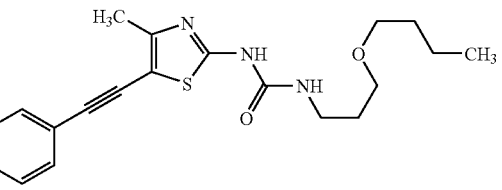
57
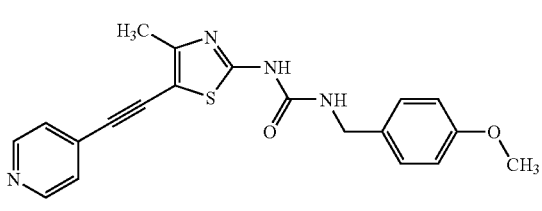
58
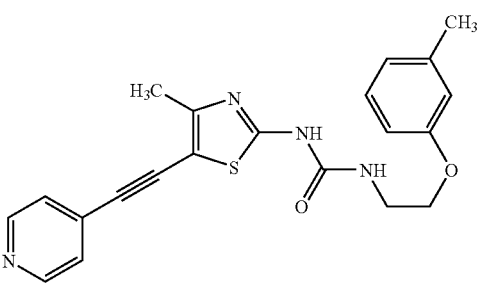
59

TABLE 1-continued
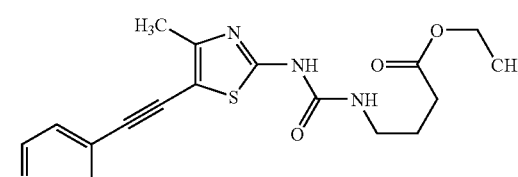
60
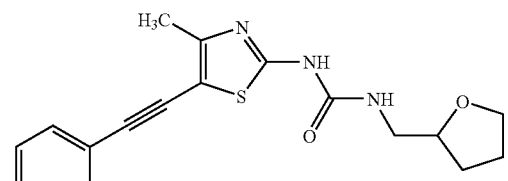
66
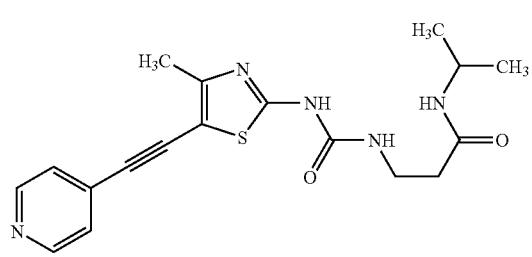
61
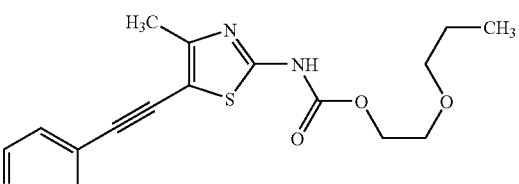
67
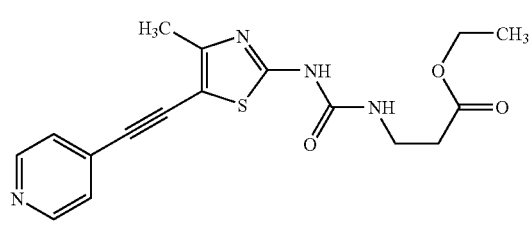
62
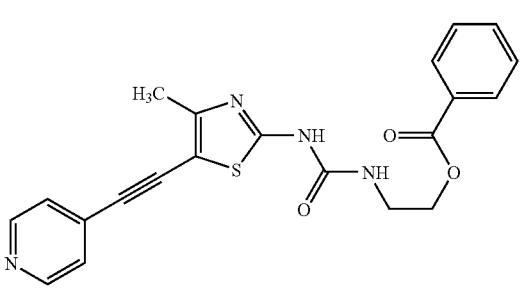
68
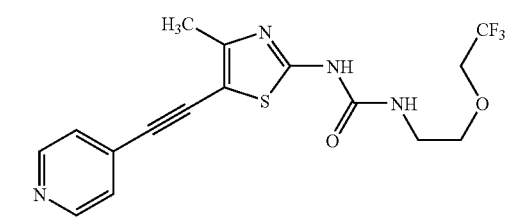
63
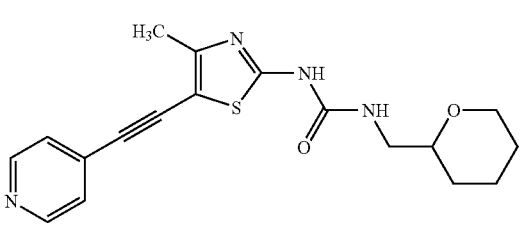
69
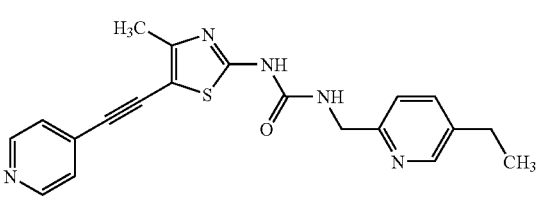
64
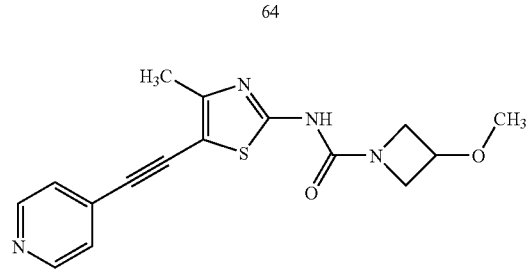
65
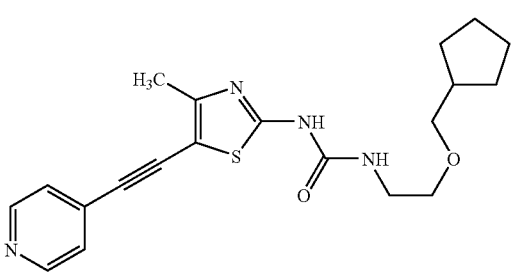
70

TABLE 1-continued
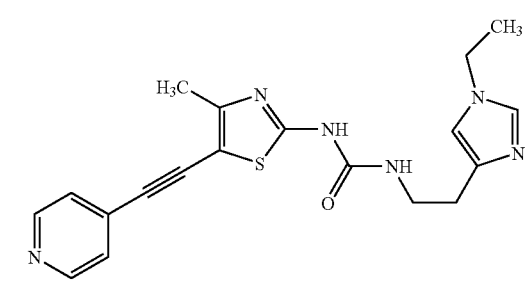
71
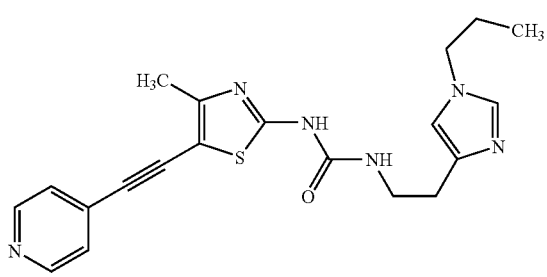
72
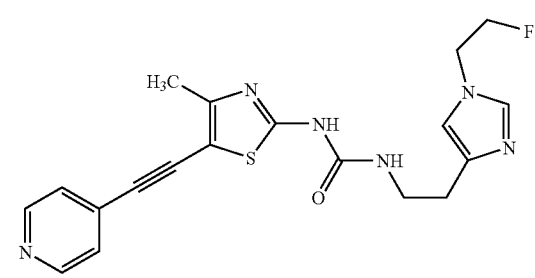
73
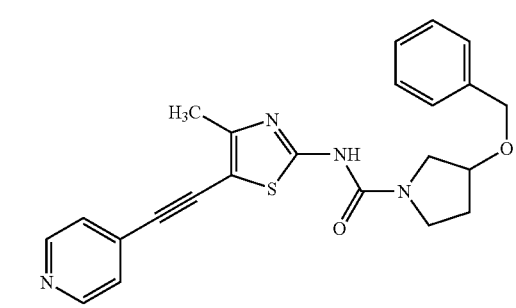
74
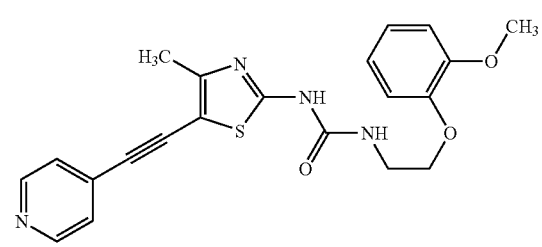
75
TABLE 1-continued
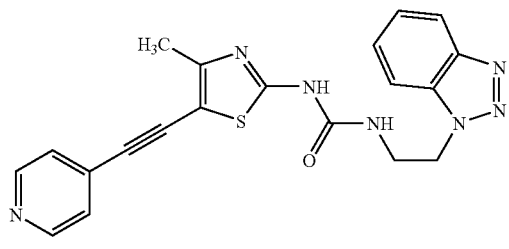
76
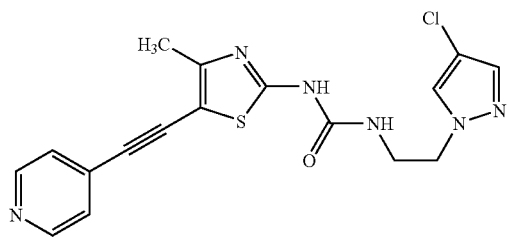
77
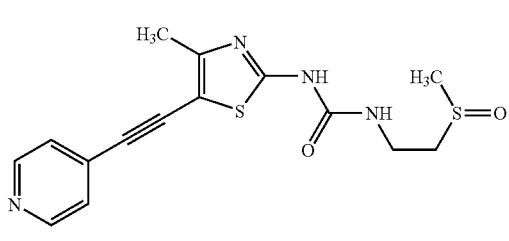
78
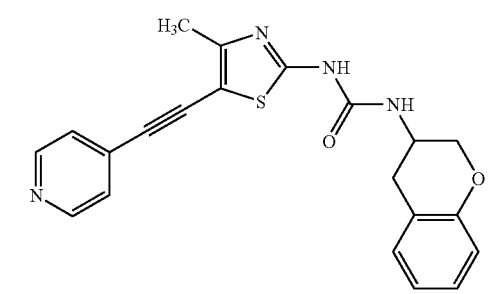
79
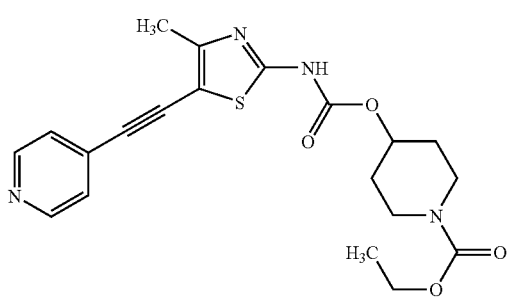
80

TABLE 1-continued
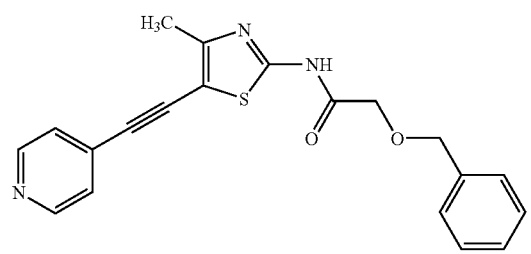
81
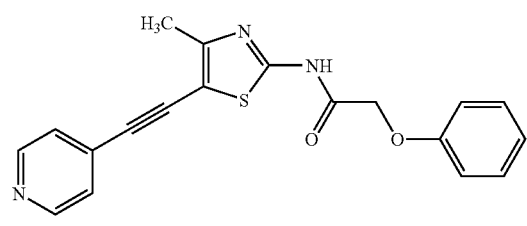
82
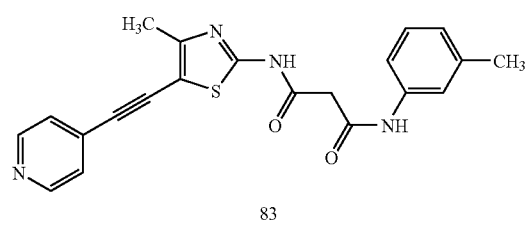 [SMILES: Cc1cccc(NC(=O)CC(=O)Nc2nc(C)c(C#Cc3ccncc3)s2)c1]
83
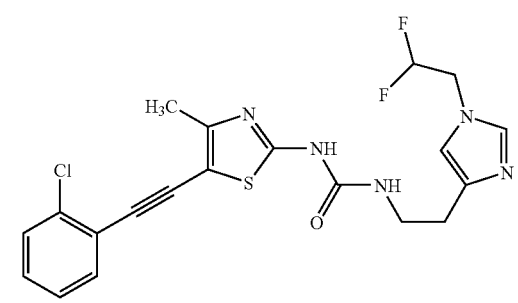
84
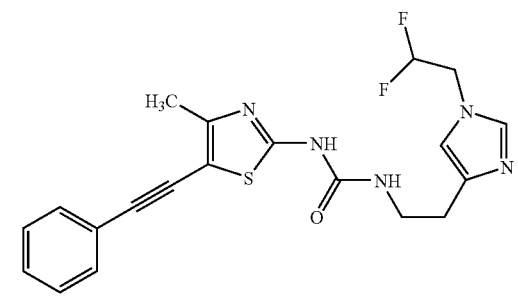
85
TABLE 1-continued
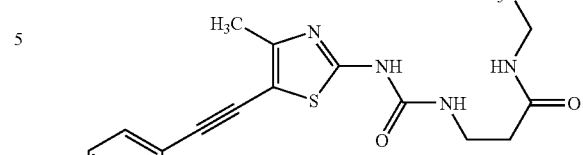
86
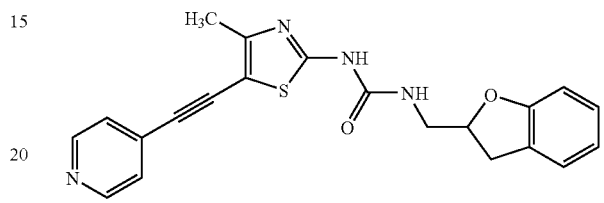
87
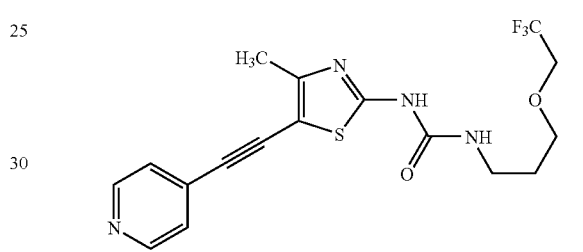
88
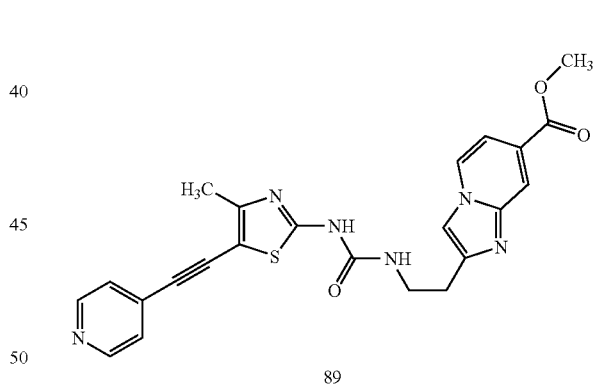
89
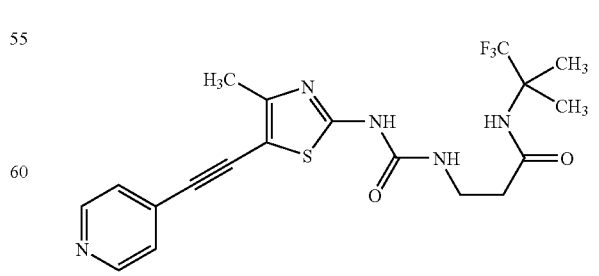
90

TABLE 1-continued
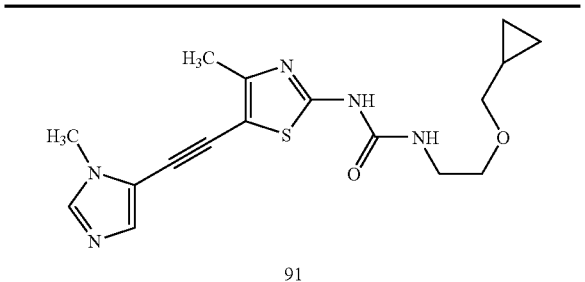
91
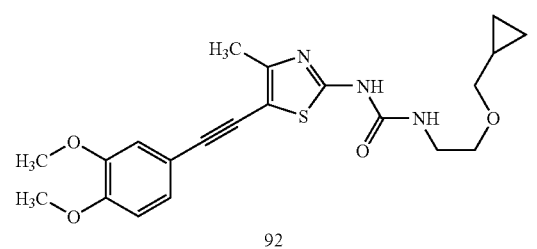 [SMILES: COc1ccc(C#Cc2sc(NC(=O)NCCOCC3CC3)nc2C)cc1OC]
92
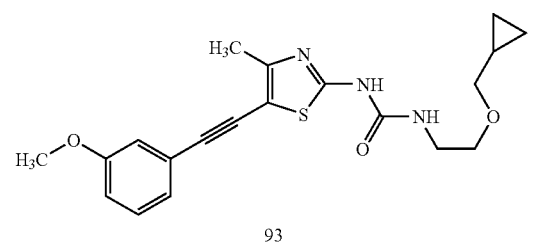 [SMILES: COc1cccc(C#Cc2sc(NC(=O)NCCOCC3CC3)nc2C)c1]
93
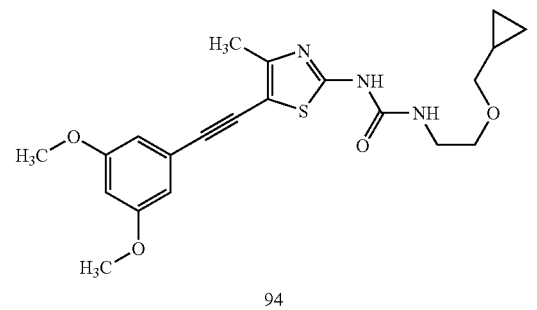 [SMILES: COc1cc(C#Cc2sc(NC(=O)NCCOCC3CC3)nc2C)cc(OC)c1]
94
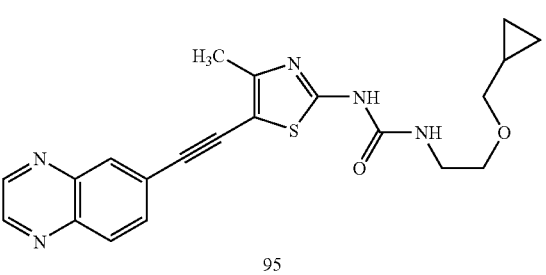 [SMILES: Cc1nc(NC(=O)NCCOCC2CC2)sc1C#Cc1ccc2nccnc2c1]
95
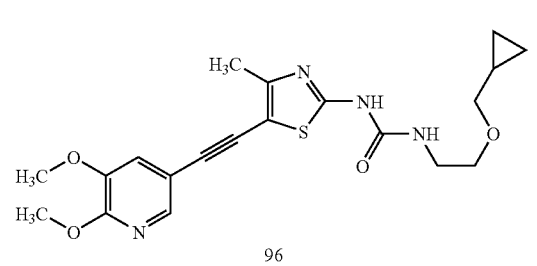 [SMILES: COc1cc(C#Cc2sc(NC(=O)NCCOCC3CC3)nc2C)cnc1OC]
96
TABLE 1-continued
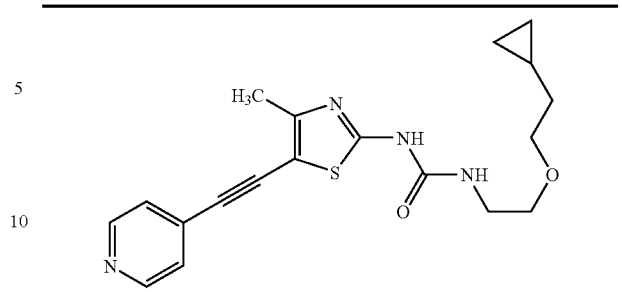
97
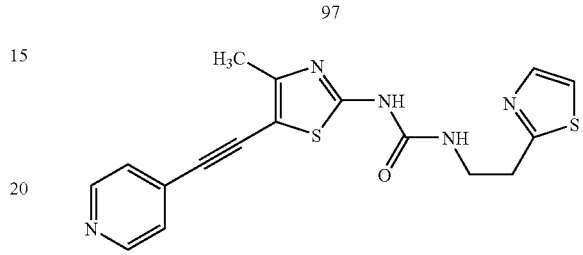
98
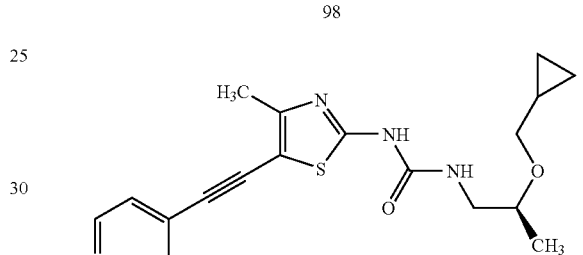
99
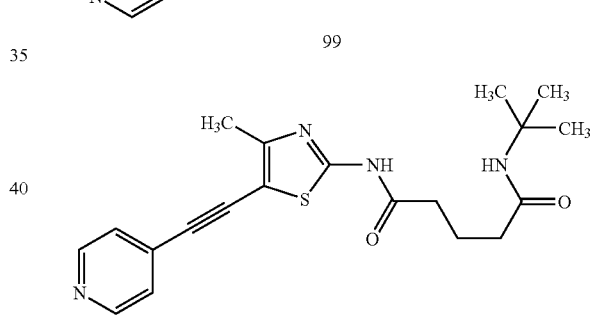
100
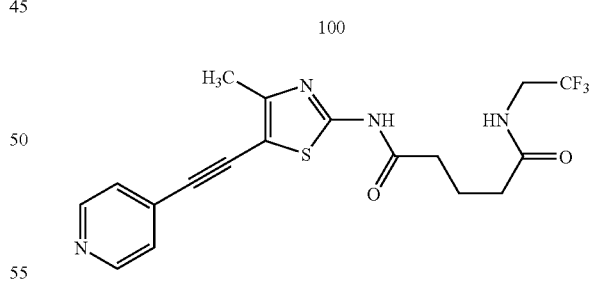
101
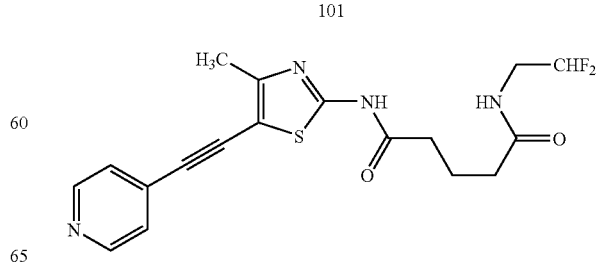
102

TABLE 1-continued
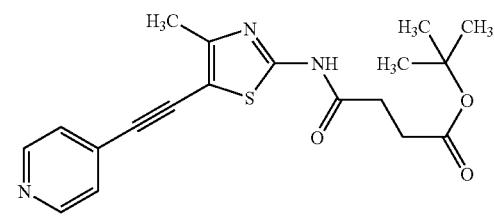
103
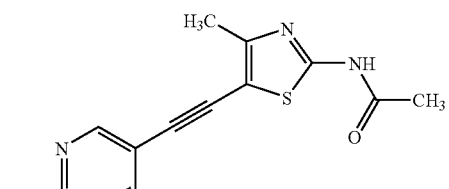
104
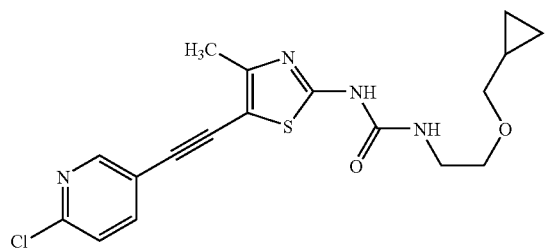
105
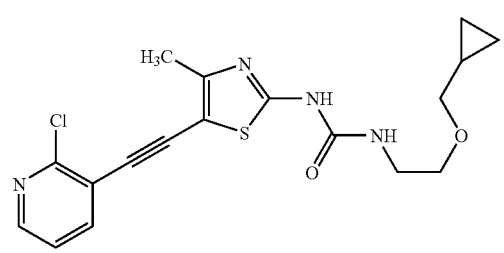
106
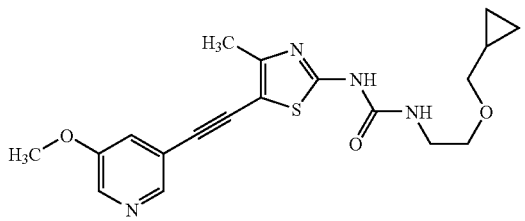
107
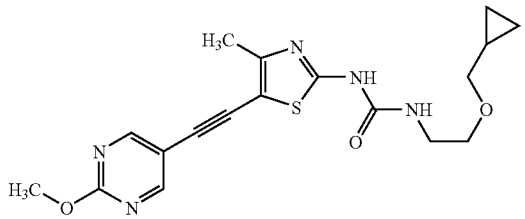
108
TABLE 1-continued
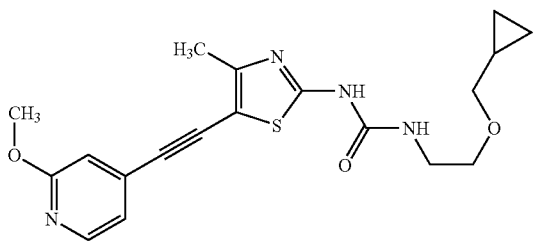
109
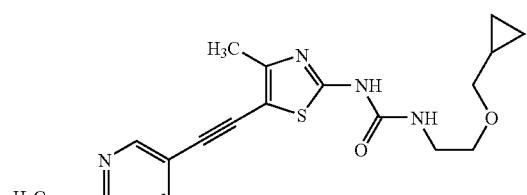
110
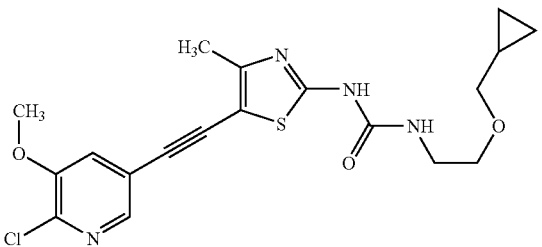
111
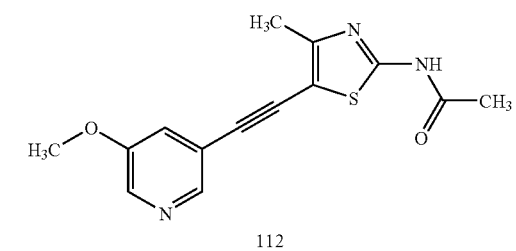 [SMILES: COc1cncc(C#Cc2sc(NC(C)=O)nc2C)c1]
112
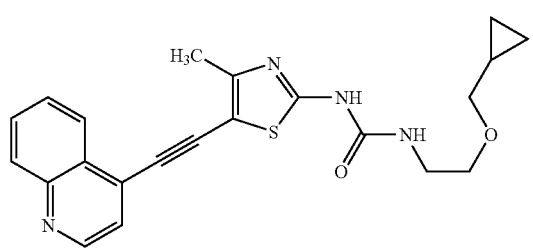
113
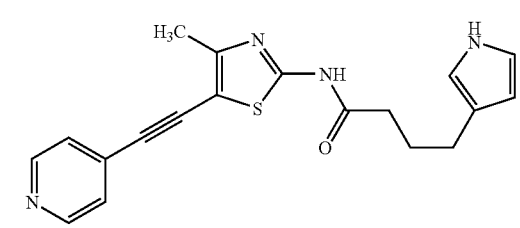
114

TABLE 1-continued
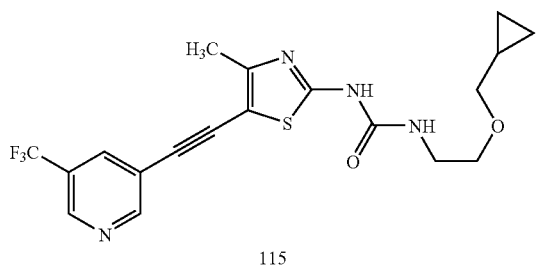 [SMILES: Cc1nc(NC(=O)NCCOCC2CC2)sc1C#Cc1cncc(C(F)(F)F)c1]
115
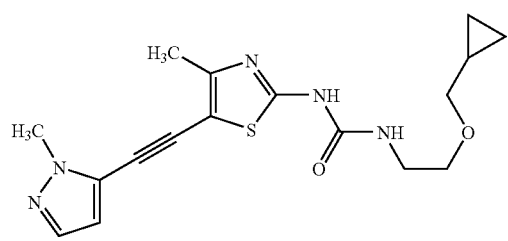
116
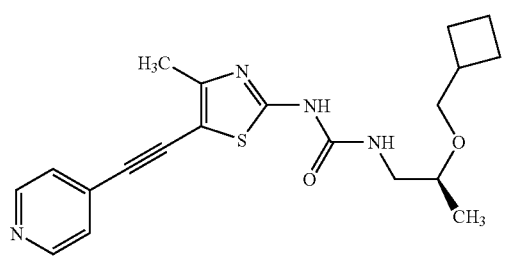
117
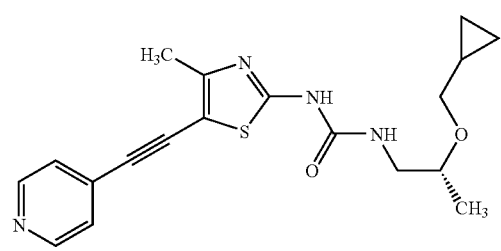
118
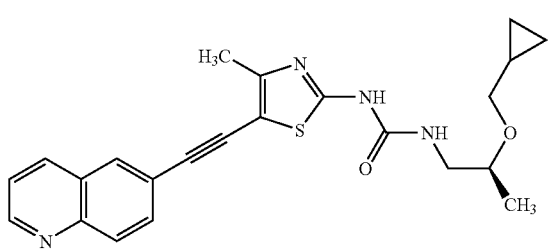
119
TABLE 1-continued
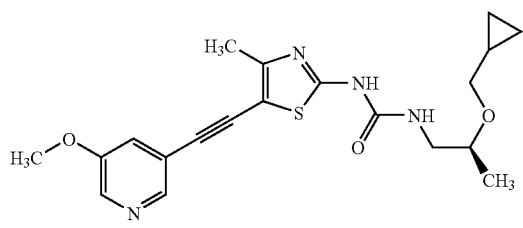
120
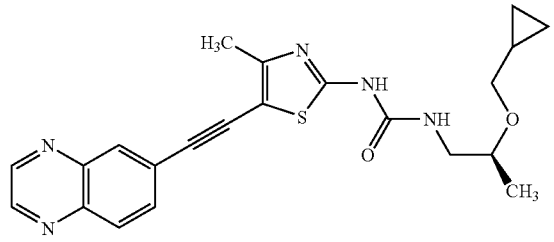
121
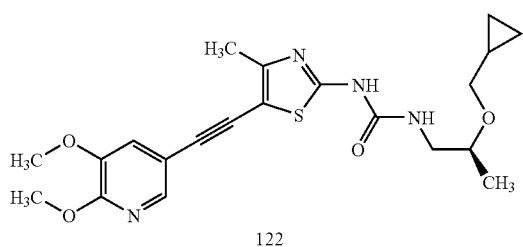 [SMILES: COc1cc(C#Cc2sc(NC(=O)NC[C@H](C)OCC3CC3)nc2C)cnc1OC]
122
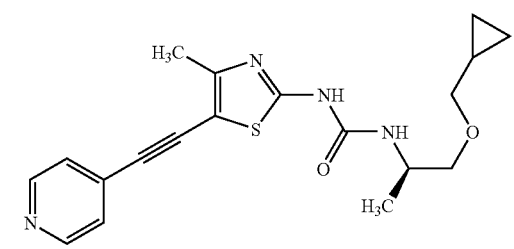
123
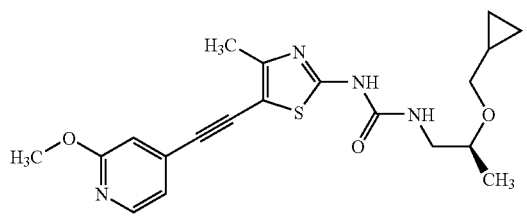
124
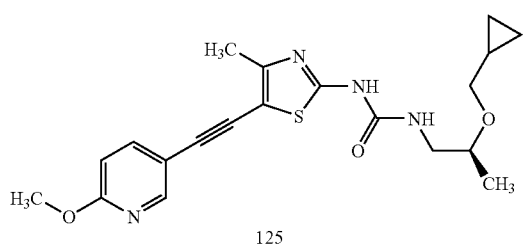 [SMILES: COc1ccc(C#Cc2sc(NC(=O)NC[C@H](C)OCC3CC3)nc2C)cn1]
125

TABLE 1-continued
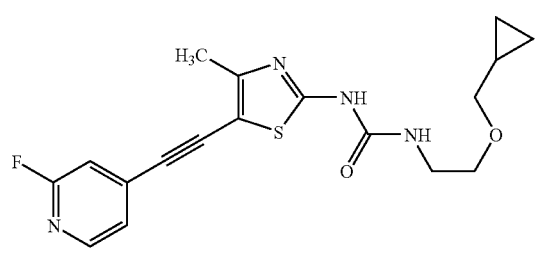
126
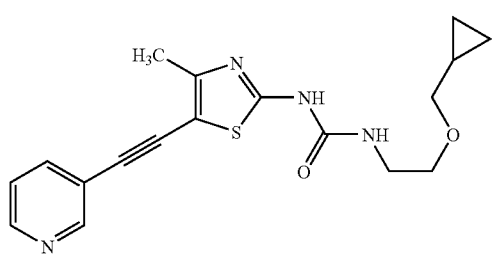
127
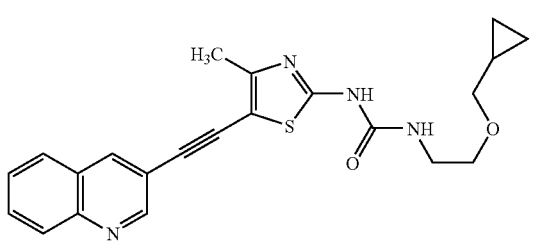
128
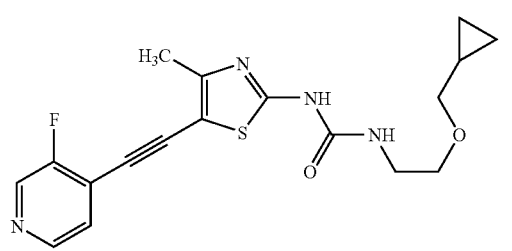
129
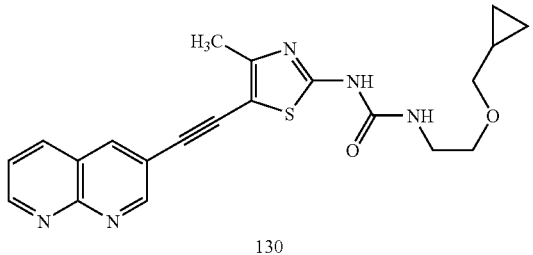 [SMILES: Cc1nc(NC(=O)NCCOCC2CC2)sc1C#Cc1cnc2ncccc2c1]
130
TABLE 1-continued
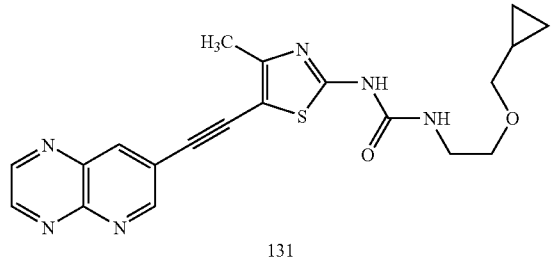 [SMILES: Cc1nc(NC(=O)NCCOCC2CC2)sc1C#Cc1cnc2nccnc2c1]
131
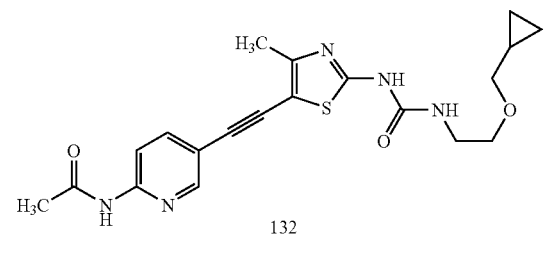 [SMILES: CC(=O)Nc1ccc(C#Cc2sc(NC(=O)NCCOCC3CC3)nc2C)cn1]
132
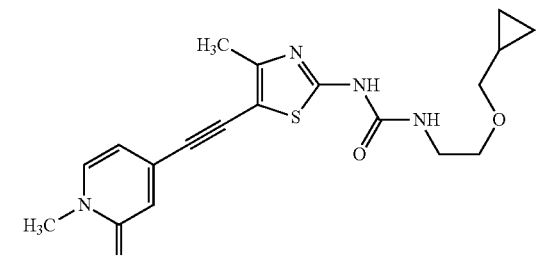
133
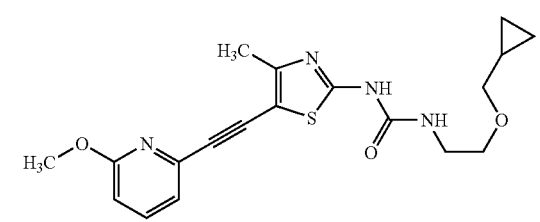
134
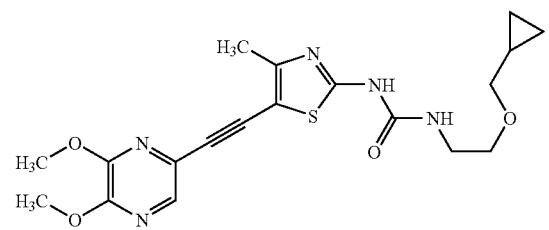
135
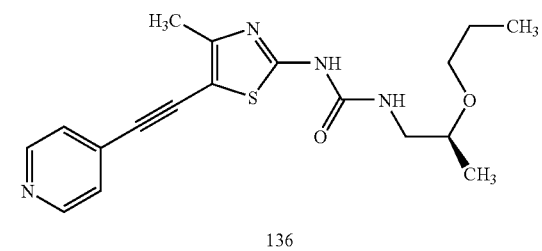 [SMILES: CCCO[C@@H](C)CNC(=O)Nc1nc(C)c(C#Cc2ccncc2)s1]
136

TABLE 1-continued
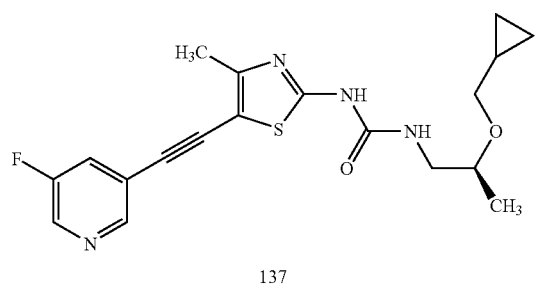 [SMILES: Cc1nc(NC(=O)NC[C@H](C)OCC2CC2)sc1C#Cc1cncc(F)c1]
137
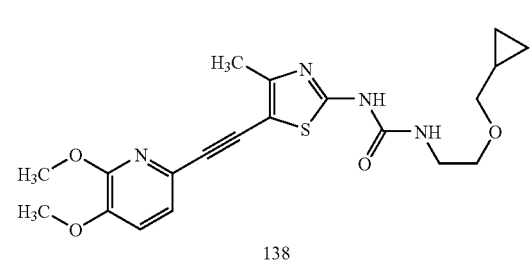
138
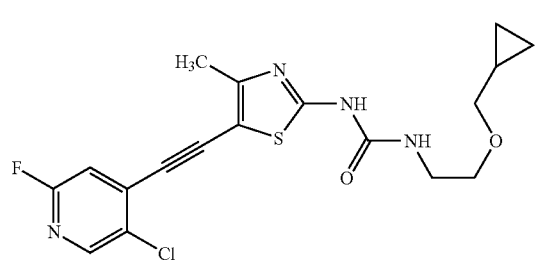
139
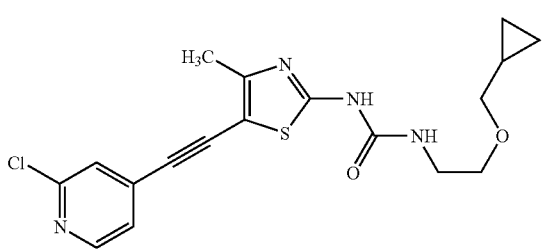
140
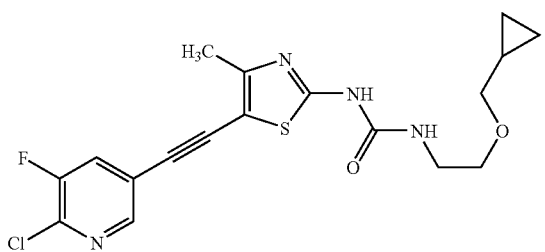
141
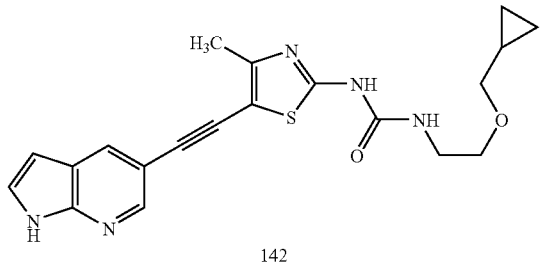 [SMILES: Cc1nc(NC(=O)NCCOCC2CC2)sc1C#Cc1cnc2[nH]ccc2c1]
142
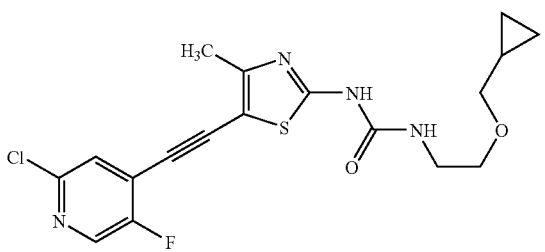
143
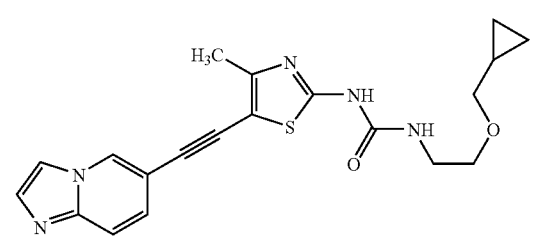
144
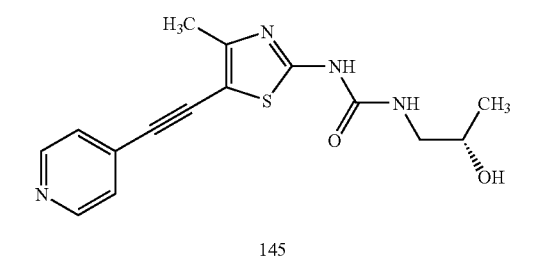 [SMILES: Cc1nc(NC(=O)NC[C@H](C)O)sc1C#Cc1ccncc1]
145
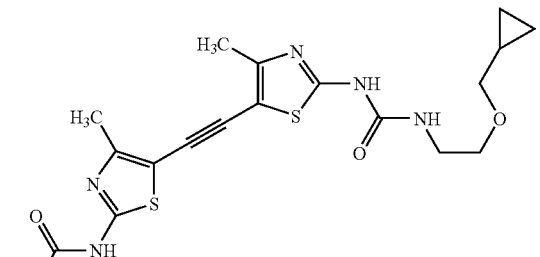
146

TABLE 1-continued
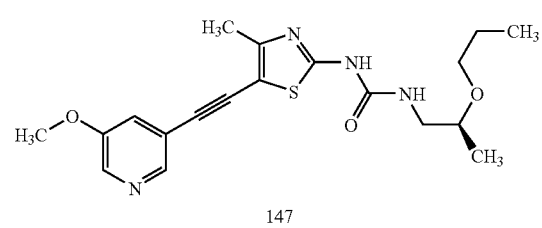 [SMILES: CCCO[C@@H](C)CNC(=O)Nc1nc(C)c(C#Cc2cncc(OC)c2)s1]
147
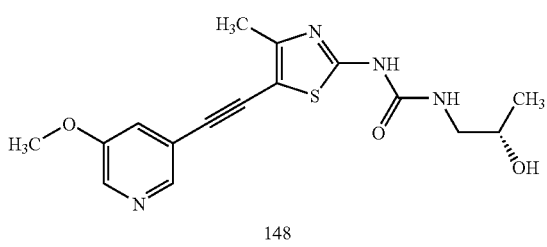 [SMILES: COc1cncc(C#Cc2sc(NC(=O)NC[C@H](C)O)nc2C)c1]
148
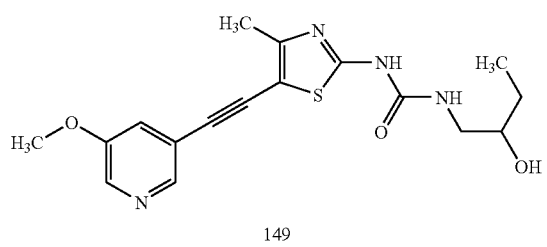 [SMILES: CCC(O)CNC(=O)Nc1nc(C)c(C#Cc2cncc(OC)c2)s1]
149
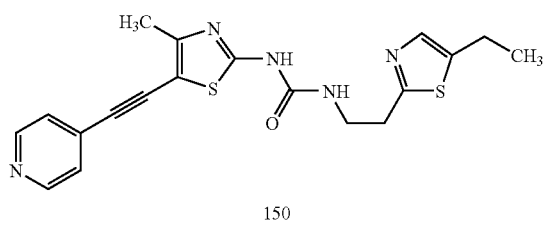 [SMILES: CCc1cnc(CCNC(=O)Nc2nc(C)c(C#Cc3ccncc3)s2)s1]
150
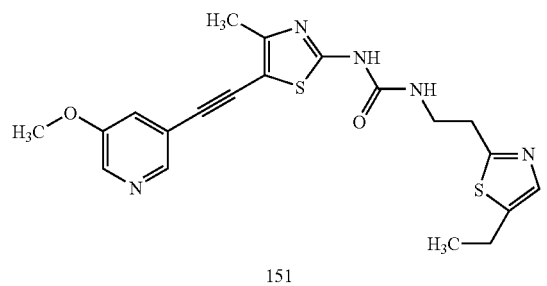 [SMILES: CCc1cnc(CCNC(=O)Nc2nc(C)c(C#Cc3cncc(OC)c3)s2)s1]
151
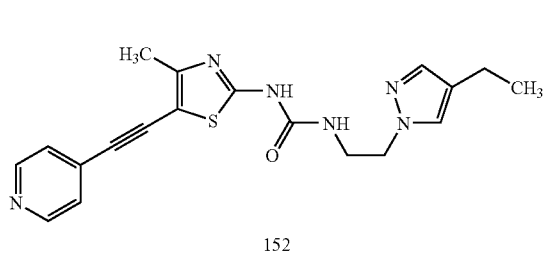 [SMILES: CCc1cnn(CCNC(=O)Nc2nc(C)c(C#Cc3ccncc3)s2)c1]
152
TABLE 1-continued
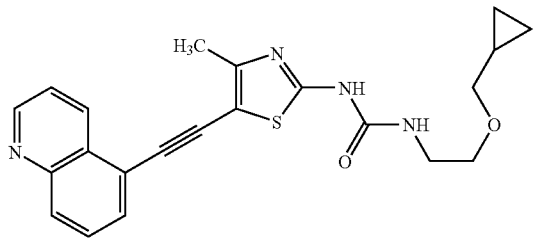
153
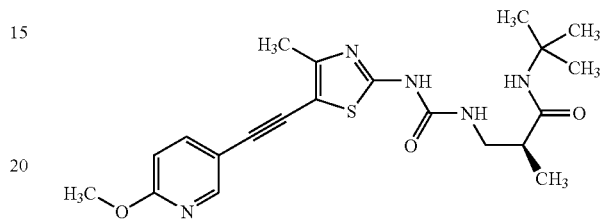
154
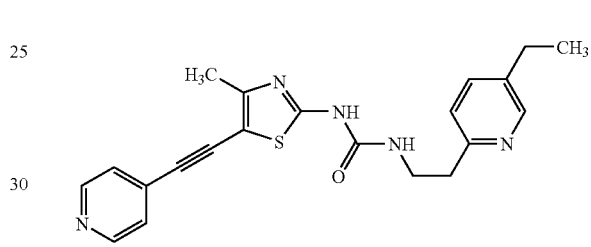
155
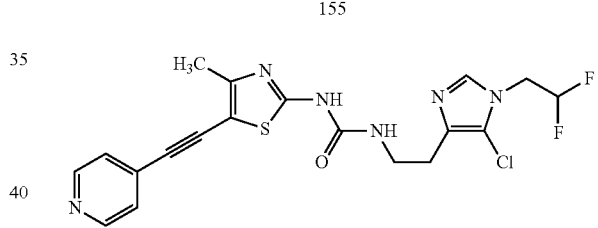
156
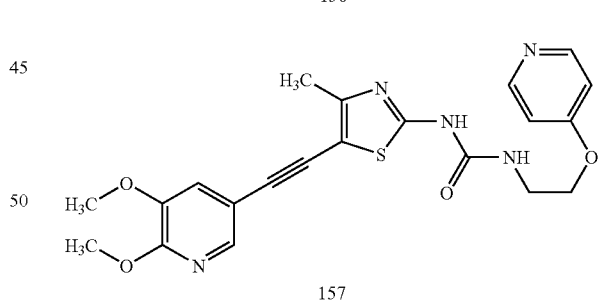
157
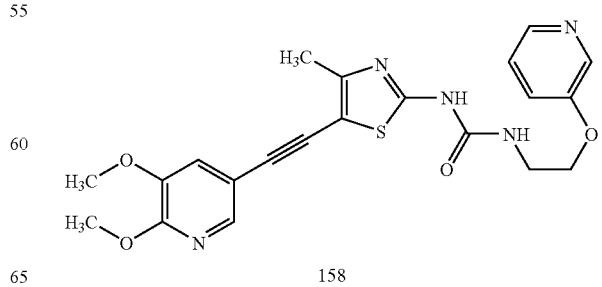
158

TABLE 1-continued

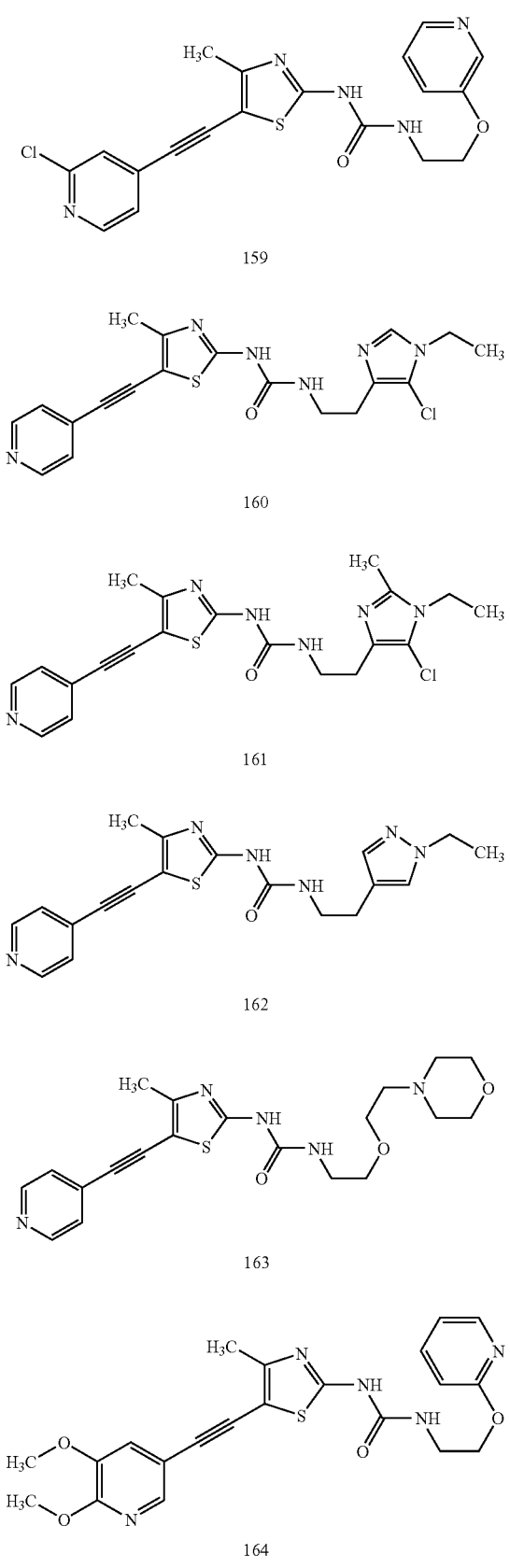

159

160

161

162

163

164

TABLE 1-continued

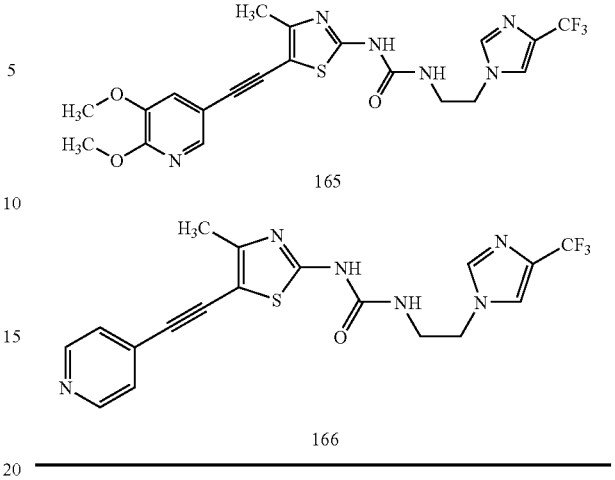

165

166

The invention also features a pharmaceutical composition comprising a compound of the invention and a pharmaceutically acceptable carrier, adjuvant, or vehicle.

In one embodiment, the composition includes a therapeutic agent selected from an agent for treating multiple sclerosis, an anti-inflammatory agent, an immunomodulatory agent, or an immunosuppressive agent.

In another embodiment, the invention features a method of treating or lessening the severity of a disease or condition selected from an autoimmune disease or an inflammatory disease of the brain or spinal cord, comprising the step of administering to said patient a compound of the invention or a pharmaceutical composition thereof.

In a further embodiment, the disease or disorder is multiple sclerosis.

In another embodiment, the method of treatment includes administering to a patient a compound or composition of the invention and an additional therapeutic agent, wherein the additional therapeutic agent is appropriate for the disease being treated and is administered together with the compound or composition as a single dosage form, or separately as part of a multiple dosage form. Examples of such additional therapeutic agents are those useful for treating multiple sclerosis, such as beta interferon, glatiramir, natalizumab, or mitoxantrone.

The invention also features a non-therapeutic method of inhibiting PI3K-gamma kinase activity in a biological sample comprising contacting said biological sample with a compound of formula I, or a composition containing said compound.

Compositions, Formulations, and Administration of Compounds of the Invention

In another embodiment, the invention provides a pharmaceutical composition comprising a compound of any of the formulae or classes described herein. In a further embodiment, the invention provides a pharmaceutical composition comprising a compound of Table 1. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a PI3K, particularly PI3Kγ, in a biological sample or in a patient. In another embodiment, the amount of compound in the compositions of this invention is such that is effective to measurably inhibit PI3Kα. In one embodiment, the composition of this invention is formulated for administration to a patient in need of such composition. In a further embodiment, the composition of this invention is formulated for oral administration to a patient.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitory active metabolite or residue thereof" means that a metabolite or residue thereof is also an inhibitor of PI3K.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In one embodiment, the invention provides a method of inhibiting PI3K activity in the brain or spinal cord of a patient, the method comprising administering to said patient a compound or composition of the invention.

In another embodiment, the invention comprises a method of treating or lessening the severity of a PI3K-mediated condition or disease in the brain or spinal cord of a patient. The term "PI3K-mediated disease", as used herein means any disease or other deleterious condition in which a PI3K isoform is known to play a role. In one embodiment, the PI3K isoform is PI3Kγ. In another embodiment, the PI3K isoform is PI3Kα. In a further embodiment, the invention comprises a method of treating a PI3K-mediated disease of the central nervous system. Such conditions include, without limitation, inflammatory diseases, cancer, and autoimmune-related diseases of the central nervous system. Accordingly, the invention provides a method of treating or lessening the severity of a disease of condition selected from a cancer, an autoimmune disease, or an inflammatory disease of the central nervous system of a patient, comprising administering to said patient a compound or composition of the invention.

In one embodiment, the invention provides a method of treating or lessening the severity of cancers of the brain and spinal cord. Examples of such cancers include, without limitation, high-grade invasive astrocytomas (e.g. anaplastic astrocytoma, gliobastoma multiforme), high-grade invasive astrocytomas, oligodendrogliomas, ependymomas, brain metastases, carcinomatous/lymphomatous meningitis, primary CNS lymphoma, and metastatic spinal tumors.

In another embodiment, the invention provides a method of treating or lessening the severity of an inflammatory or autoimmune disease or disorder of the central nervous system. In another embodiment, the invention provides a method of treating or lessening the severity of a symptom of an inflammatory or autoimmune disease or disorder of the central nervous system. In a further embodiment, the invention provides a method of treating neuroinflammation. Such diseases or disorders include, without limitation, multiple sclerosis, transverse myelitis, progressive multifocal leukoencephalopathy, meningitis, encephalitis, myelitis, encephalomyelitis, intracranial or intraspinal abscess, phlebitis or thrombophlebitis of intracranial venous sinuses, stroke, Parkinson's Disease, Alzheimer's Disease, Huntington's Disease, Pick's Disease, amyotrophic lateral sclerosis, HIV type-I dementia, frontotemporal lobe dementia, traumatic brain or spinal cord injury, autism, or a prion disease.

Compounds or compositions of the invention may be administered with one or more additional therapeutic agents, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration may be staggered by, for example, 6 hours, 12 hours, 1 day, 2 days, 3 days, 1 week, 2 weeks, 3 weeks, 1 month, or 2 months.

Non-limiting examples of chemotherapeutic agents or other anti-proliferative agents that may be combined with the compounds of this invention include taxanes, aromatase inhibitors, anthracyclines, microtubule targeting drugs, topoisomerase poison drugs, targeted monoclonal or polyconal antibodies, inhibitors of a molecular target or enzyme (e.g., a kinase inhibitor), or cytidine analogues. In one embodiment, the additional chemotherapeutic agent is amsacrine, anastrozole, asparaginase, Avastin™ (bevacizumab) azathioprine, bicalutamide, bleomycin, camptothecin, carmustine, chlorambucil, cyclophosphamide, cytarabine (araC), daunonibicin, dactinomycin, doxorubicin (adriamycin), epirubicin, epothilone, etoposide, exemestane, fludarabine, 5-fluorouracil (5-FU), flutamide, Gemzar™ (gemcitabine), Gleevec™ (imatanib), Herceptin™ (trastuzumab), idarubicin, ifosfamide, an interferon, an interleukin, irinotecan, letrozole, leuprolide, lomustine, lovastatin, mechlorethamine, megestrol, melphalan, 6-mercaptopurine, methotrexate (MTX), minosine, mitomycin, mitoxantrone, navelbine, nocodazole, platinum derivatives such as cisplatin, carboplatin and oxaliplatin, raloxifene, tamoxifen, Taxotere™ (docetaxel), Taxol™ (paclitaxel), teniposide, topotecan, tumor necrosis factor (TNF), vinblastin, vincristin, vindesine, vinorelbine, or Zoladex™ (goserelin). Another chemotherapeutic agent can also be a cytokine such as G-CSF (granulocyte colony stimulating factor). In yet another embodiment, a compound of the present invention, or a pharmaceutically acceptable salt, prodrug, metabolite, analog or derivative thereof, may be administered in combination with surgery, radiation therapy, or with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

Additional therapeutic agents also include those useful for treating multiple sclerosis (MS), such as, for example, beta interferon (e.g., Avonex® and Rebif®), glatiramir (Copaxone®), Tysabri® (natalizumab), Betaseron® (IFN-beta), and mitoxantrone.

The invention provides a method of inhibiting PI3K kinase activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly PI3K kinase activity, in a biological sample is useful for a variety of purposes known to one of skill in the art. Examples of such purposes include, but are not limited to, biological specimen storage and biological assays. In one embodiment, the method of inhibiting PI3K kinase activity in a biological sample is limited to non-therapeutic methods.

Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations used herein:

| | |
|---|---|
| ATP | adenosine triphosphate |
| Boc | t-butoxylcarbonyl |
| Brine | a saturated NaCl solution in water |
| DCM | dichloromethane |
| DIEA | diisopropylethylamine |
| DMA | dimethylacetamide |
| DMAP | 4-dimethylaminopyridine |
| DMF | dimethylformamide |
| DMSO | methylsulfoxide |
| DTT | dithiothreitol |
| ESMS | electrospray mass spectrometry |
| Et₂O | ethyl ether |
| EtOAc | ethyl acetate |
| EtOH | ethyl alcohol |
| HEPES | 4-(2-hydroxyethyl)-1-piperazineethanesulfonic acid |
| HPLC | high performance liquid chromatography |
| LC-MS | liquid chromatography-mass spectrometry |
| Me | methyl |

-continued

| MeOH | methanol |
| MTBE | methyl t-butyl ether |
| MC | methyl cellulose |
| NIS | N-iodosuccinimide |
| NMP | N-methylpyrrolidine |
| PBS | phosphate buffered saline |
| Ph | phenyl |
| RT or rt | room temperature |
| tBu | tertiary butyl |
| TCA | trichloroacetic acid |
| THF | tetrahydrofuran |
| TEA | triethylamine |
| TFA | trifluoacetic acid |

General Synthetic Procedures

In general, the compounds of this invention may be prepared by methods described herein or by other methods known to those skilled in the art.

EXAMPLE 1

General Preparation of the Compounds of Formula I

The preparation of compounds of formula I, wherein $R^1$ is —C(O)$R^{1a}$ or —C(O)N($R^{1a}$)$_2$, is shown in Scheme 1. Accordingly, the amine a compound of formula A1, where $R^2$ is as defined for a compound of formula I, is protected to form a compound of formula A2. Commonly used protecting groups are disclosed in Greene and Wuts, *Protective Groups In Organic Synthesis*, 3$^{rd}$ *Edition* (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz). Subsequent reaction with N-iodosuccinamide in acetonitrile produces a compound of formula A3 (where J is iodo). The iodothiazole of formula A3 can be reacted with an optionally substituted phenyl or heteroaryl acetylene (e.g., R is phenyl or 5-6 membered heteroaryl) under Sonogashira coupling conditions (PdCl$_2$(PPh$_3$)$_2$/CuI/triethylamine/acetonitrile) to produce a compound of formula A5. See Chinchilla et al., *Chemical Reviews* 107(3): 874, 2007 for a review of the Sonogashira coupling. Compounds of formula A5 can also be prepared by (i) reacting compounds of formula A3 with trimethylsilylacetylene under Sonogashira conditions to produce a compound of formula A4, (ii) removal of the trimethylsilyl group, and (iii) reacting the resulting terminal alkyne with an aryl or heteroaryl iodide under Sonogashira conditions. Removal of the amine protecting group from a compound of formula A2 produces a compound of formula A6. The primary amine of a compound of formula A3 can be used to form ureas such as compounds of formulae A7 and A8, wherein $R^{1a}$ and $R^{1b}$ are as defined for a compound of formula I. The primary amine of a compound of formula A6 can also be reacted with esters or carboxylic acids (through their activated esters) by methods known to those skilled in the art to form compounds having the formula A9.

Scheme 1

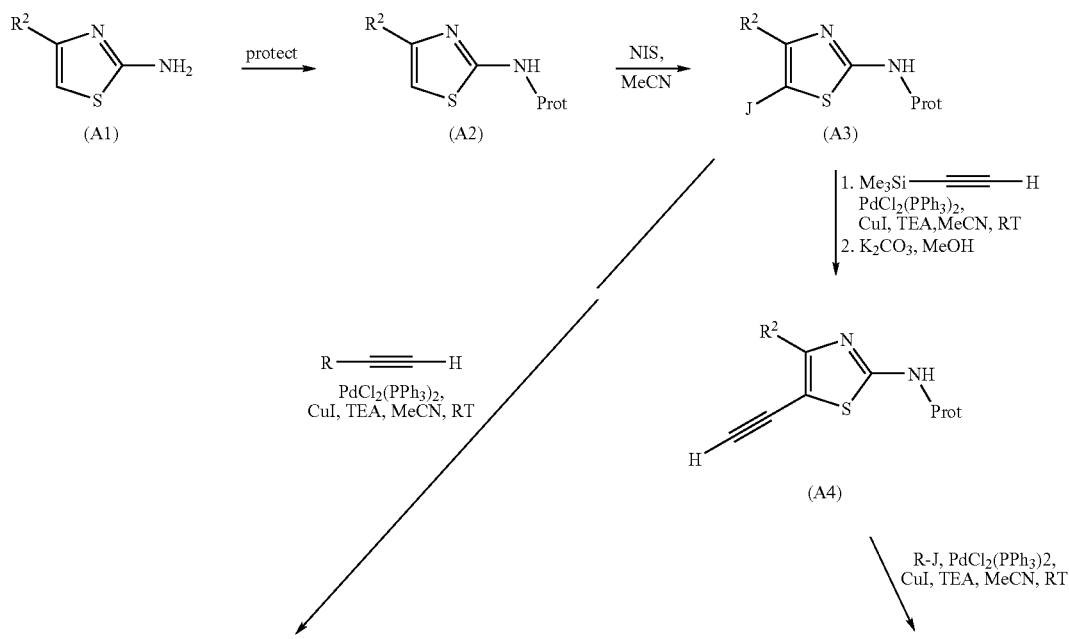

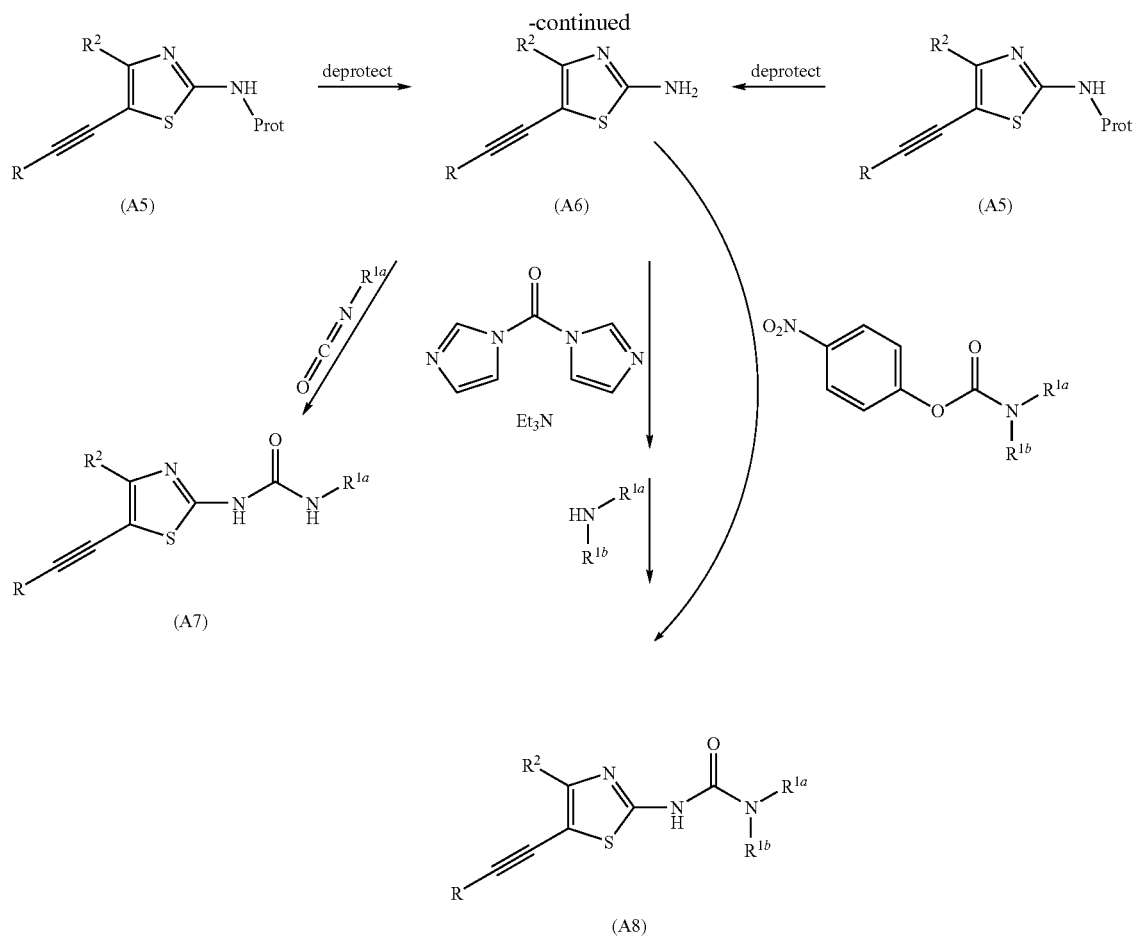

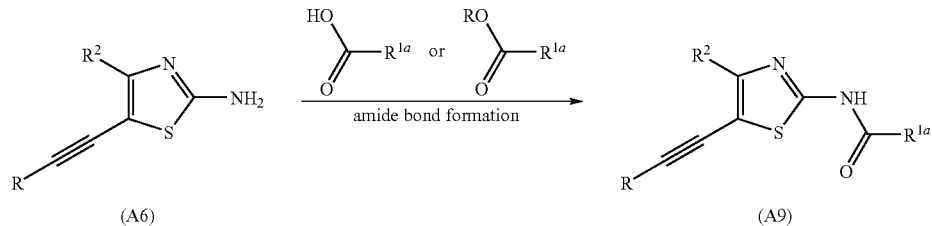

EXAMPLE 2

Preparation of 3-N-(4-methyl-5-(2-(pyridin-3-yl) ethynyl)thiazol-2-yl)-1H-imidazole-1-carboxamide (compound 1005)

N-(5-iodo-4-methylthiazol-2-yl)acetamide (compound 1001) was prepared according to the procedure of *J. Org. Chem.* 30(4): 1101-1104, 1965. As shown in step 2-i of Scheme 2, compound 1001 (500 mg, 1.77 mmol) and 3-ethynylpyridine (228 mg, 2.22 mmol) were stirred in 5 mL of THF. After purging the solution with nitrogen gas, CuI (34 mg, 0.177 mmol) and bis(triphenylphosphine)palladium(II) chloride (124 mg, 0.177 mmol) were added, followed by the addition of triethylamine (538 mg, 5.32 mmol). The reaction mixture was stirred at RT for 1.5 hours. The reaction mixture was filtered and the volatiles were removed under reduced pressure to produce N-(4-methyl-5-(pyridin-3-ylethynyl) thiazol-2-yl)acetamide (compound 1003, 300 mg, 77% yield): $^1$H-NMR (DMSO-$d_6$) δ 12.43 (s, 1H), 8.74 (s, 1H), 8.57 (d, J=2.9 Hz, 1H), 7.96 (d, J=8.0 Hz, 1H), 7.46 (dd, J=4.8, 7.9 Hz, 1H), 8.57 (d, J=2.9 Hz, 1H), 7.96 (d, J=8.0 Hz, 1H), 7.46 (dd, J=4.8, 7.9 Hz, 1H), 2.41 (s, 3H), and 2.16 (s, 3H) ppm.

As shown in step 2-ii of Scheme 2, compound 1003 (400 mg, 1.56 mmol) was stirred in hydrazine hydrate at 70° C. for 20 minutes. Water was added and the resulting precipitate was collected by filtration, washed with water, and dried under high vacuum to produce 4-methyl-5-(pyridin-3-ylethynyl) thiazol-2-amine (compound 1004), which was used in subsequent reactions as is.

As shown in step 2-iii of Scheme 2, compound 1004 (91 mg, 0.423 mmol), 1,1'-carbonyldiimidazole (103 mg, 0.634 mmol), and triethylamine (85.6 mg, 0.845 mmol) were stirred in 2.1 mL of DMF at 60° C. for 2 hours. After this time, MTBE was added and the resulting precipitate collected by filtration to produce N-(4-methyl-5-(pyridin-3-ylethynyl)thiazol-2-yl)-1H-imidazole-1-carboxamide (compound 1005, 120 mg), which was immediately used in subsequent reactions as is.

Scheme 2

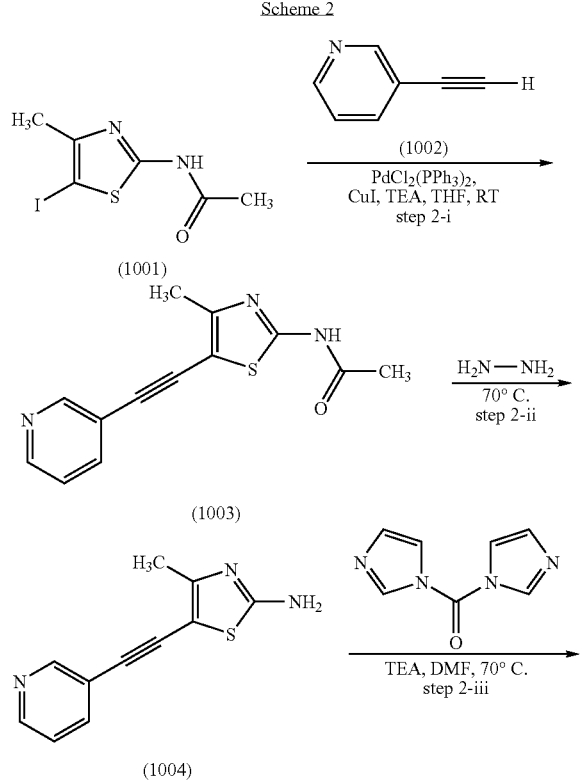

ethylamine (29 mg, 0.32 mmol, Aldrich Chem. Co. cat. no. 44, 840-0). After stirring for 20 hours, the mixture purified by medium pressure silica gel chromatography (20-60% EtOAc/hexanes) to provide 1-(4-methyl-5-(2-(pyridin-3-yl)ethynyl)thiazol-2-yl)-3-(2-phenoxyethyl)urea (compound 9).

Scheme 3

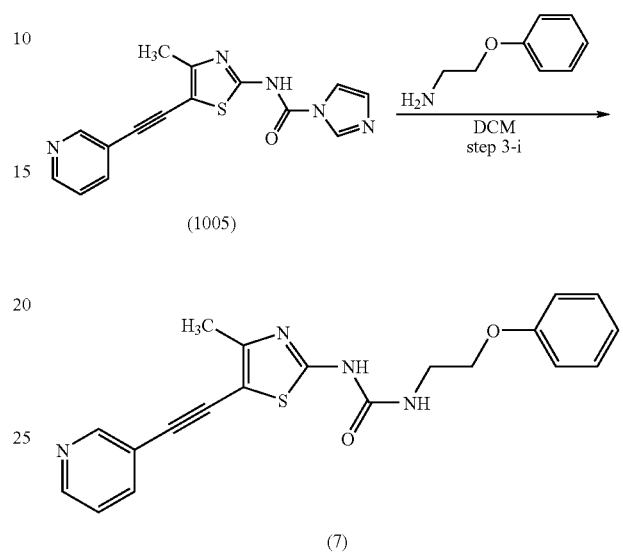

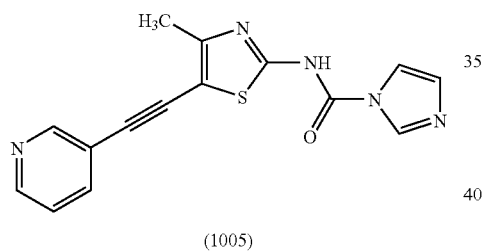

EXAMPLE 3

Preparation of 1-(4-methyl-5-(2-(pyridin-3-yl)ethynyl)thiazol-2-yl)-3-(2-phenoxyethyl)urea (compound 9)

As shown in step 3-i of Scheme 3, compound 1005 (25 mg, 0.08 mmol) in 0.40 mL of DCM was reacted with 2-phenoxy-

EXAMPLE 4

Preparation of 1-(2-(1-(2,2-difluoroethyl)-1H-imidazol-4-yl)ethyl)-3-(4-methyl-5-(2-(pyridin-3-yl)ethynyl)thiazol-2-yl)urea (compound 8)

Intermediate 2-heteroarylethanamines can be prepared according to the procedures set forth in International Patent Application Publication Nos. PCT/EP2004/009586 and PCT/EP2008/059298. As shown in step 4-i of Scheme 4, compound 1005 (25 mg, 0.08 mmol) in 0.40 mL of DCM was treated with triethylamine (82 mg, 0.81 mmol) and 2-(1-(2,2-difluoroethyl)-1H-imidazol-4-yl)ethanamine (80 mg, 0.32 mmol). After stirring for 20 hours, the reaction mixture was filtered, treated with cold methyl t-butylether, and filtered once more. The filtrate was concentrated under reduced pressure and purified by medium pressure silica gel chromatography (0-10% MeOH/DCM) to provide 1-(2-(1-(2,2-difluoroethyl)-1H-imidazol-4-yl)ethyl)-3-(4-methyl-5-(2-(pyridin-3-yl)ethynyl)thiazol-2-yl)urea (compound 8).

Scheme 4

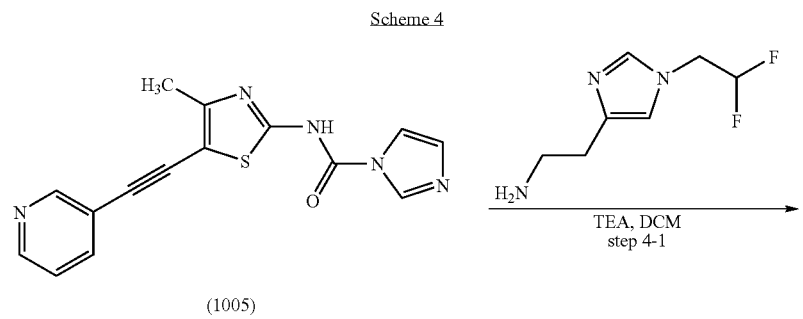

-continued

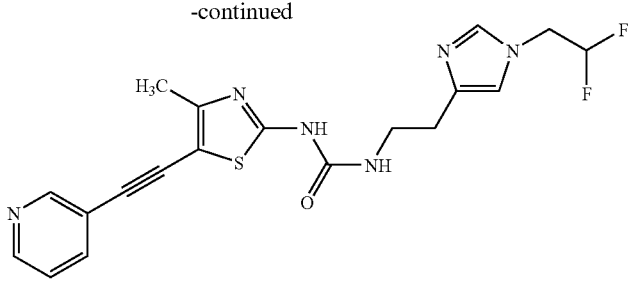

(6)

Table 2 provides analytical characterization data for certain compounds of formula I (blank cells indicate that the test was not performed). Compound numbers in Table 2 correspond to those depicted in Table 1.

TABLE 2

| Compound No. | ESMS (M + H) | $^1$H NMR (300 MHz, unless indicated otherwise) NMR peaks given as δ values |
|---|---|---|
| 1 | 326.2 | (DMSO-$d_6$): 12.48 (s, 1H), 9.03 (s, 1H), 8.96 (s, 1H), 8.46 (s, 1H), 2.44 (s, 3H), 2.17 (s, 3H) and 0.00 (s, H) ppm |
| 2 | 258.2 | (DMSO-$d_6$): 12.43 (s, 1H), 8.74 (s, 1H), 8.57 (d, J = 2.9 Hz, 1H), 7.96 (d, J = 8.0 Hz, 1H), 7.46 (dd, J = 4.8, 7.9 Hz, 1H), 2.41 (s, 3H) and 2.16 (s, 3H) ppm |
| 3 | 258.3 | (DMSO-$d_6$) δ 12.55 (s, 1H), 8.70 (d, J = 6.4 Hz, 2H), 7.80 (d, J = 6.4 Hz, 2H), 2.46 (s, 3H), 2.18 (s, 3H) |
| 4 | 378.5 | (DMSO-$d_6$): 12.67 (s, 1H), 9.13 (t, J = 5.9 Hz, 1H), 8.83 (s, 1H), 8.70 (d, J = 4.6 Hz, 1H), 8.62 (d, J = 4.4 Hz, 1H), 8.11-8.00 (m, 3H), 7.68-7.63 (m, 1H), 7.56 (dd, J = 5.0, 8.0 Hz, 1H), 4.25 (d, J = 6.0 Hz, 2H), 2.44 (s, 3H), 2.32 (s, 2H) |
| 5 | 392.6 | (DMSO-$d_6$): 12.52 (s, 1H), 8.93-8.89 (m, 1H), 8.79 (d, J = 1.5 Hz, 1H), 8.65-8.59 (m, 2H), 8.06-7.97 (m, 3H), 7.63-7.59 (m, 1H), 7.52 (dd, J = 5.0, 7.9 Hz, 1H), 3.63 (dd, J = 6.6, 12.9 Hz, 2H), 2.81 (t, 2H), 2.42 (s, 3H), 2.37 (s, 1.5H) |
| 6 | 417.6 | (DMSO-$d_6$): 10.84 (s, 1H), 8.71 (d, J = 1.5 Hz, 1H), 8.55 (dd, J = 1.6, 4.9 Hz, 1H), 8.18 (s, 1H), 7.94 (dt, J = 7.9, 2.5 Hz, 1H), 7.44 (dd, J = 4.9, 7.9 Hz, 1H), 7.20 (s, 1H), 6.72 (s, 1H), 6.64-6.37 (m, 1H), 4.60 (dt, J = 2.9, 15.9 Hz, 2H), 3.40 (m, 2H), 2.73 (t, J = 6.8 Hz, 2H), 2.35 (s, 3H), 2.29 (s, 2H) |
| 7 | 379.6 | (DMSO-$d_6$): 10.83 (s, 1H), 8.78 (d, J = 1.8 Hz, 1H), 8.60 (dd, J = 1.5, 5.0 Hz, 1H), 8.04 (dt, J = 8.0, 2.5 Hz, 1H), 7.53 (dd, J = 5.1, 7.9 Hz, 1H), 7.30 (dd, J = 7.2, 8.7 Hz, 2H), 6.98-6.86 (m, 4H), 4.24-3.99 (m, 2H), 3.56-3.43 (m, 2H), 2.42 (s, 3H), 2.36 (s, 5H) |
| 8 | 257.4 | (DMSO-$d_6$): 12.38 (s, 1H), 7.52 (m, 2H), 7.46-7.39 (m, 3H), 2.37 (s, 3H), 2.35 (s, 3H), 2.15 (s, 3H) |
| 9 | 272.0 | (DMSO-$d_6$): 12.7 (s, 1H), 8.82 (m, 2H), 7.94 (d, 2H), 2.86 (quar, 2H), 2.18 (s, 3H), 1.259 (t, 3H) |
| 10 | 287.2 | (DMSO-$d_6$): 12.35 (s, 1H), 7.32 (m, 1H), 7.11-7.07 (m, 2H), 6.99-6.96 (m, 1H), 3.79 (s, 3H), 2.38 (s, 3H), 2.14 (s, 3H) |
| 11 | 287.2 | (DMSO-$d_6$): 12.30 (s, 1H), 7.49-7.44 (m, 2H), 6.99-6.96 (m, 2H), 3.79 (s, 3H), 2.38 (s, 3H), 2.15 (s, 3H) |
| 12 | 272.2 | (DMSO-$d_6$): 12.26 (s, 1H), 7.24 (d, J = 8.4 Hz, 2H), 6.68 (d, J = 8.4 Hz, 2H), 2.34 (s, 3H), 2.14 (s, 3H) |
| 13 | 263.2 | (DMSO-$d_6$): 12.33 (s, 1H), 7.88 (dd, J = 1.1, 2.9 Hz, 1H), 7.66-7.57 (m, 1H), 7.29-7.21 (m, 1H), 2.36 (s, 3H), 2.15 (s, 3H) |
| 14 | 271.2 | (DMSO-$d_6$): 12.34 (s, 1H), 7.47 (d, J = 7.2 Hz, 1H), 7.34-7.20 (m, 3H), 2.44 (s, 3H), 2.36 (s, 3H), 2.17 (s, 3H) |
| 15 | 271.2 | |
| 16 | 272.2 | (DMSO-$d_6$): 12.36 (s, 1H), 7.32-6.99 (m, 6H), 2.38 (s, 3H), 2.15 (s, 3H) |
| 17 | 261.2 | (DMSO-$d_6$): 12.51 (s, 1H), 9.00 (s, 1H), 8.00 (s, 1H), 3.86 (s, 3H), 2.41 (s, 3H), 2.18 (s, 3H) |
| 18 | 275.2 | (DMSO-$d_6$): 12.38 (s, 1H), 7.50-7.36 (m, 3H), 7.29-7.22 (m, 1H), 2.37 (s, 3H), 2.17 (s, 3H) |
| 19 | 312.0 | |
| 20 | 350.0 | |
| 21 | 395.0 | |
| 22 | 435.0 | |
| 23 | 387.0 | |
| 24 | 411.7 | (DMSO-$d_6$): 10.67 (s, 1H), 8.61-8.57 (m, 1H), 7.53-7.39 (m, 5H), 6.72-6.68 (m, 1H), 3.97-3.85 (m, 2H), 3.36 (dd, J = 6.4, 12.5 Hz, 2H), 2.42 (t, J = 6.5 Hz, 2H), 2.32 (s, 3H) |

TABLE 2-continued

| Compound No. | ESMS (M + H) | ¹H NMR (300 MHz, unless indicated otherwise) NMR peaks given as δ values |
|---|---|---|
| 25 | 425.7 | (DMSO-$d_6$): 10.69 (s, 1H), 7.52-7.39 (m, 5H), 6.75-6.71 (m, 1H), 4.34-4.13 (m, 2H), 3.37 (q, J = 6.0 Hz, 2H), 3.07 (s, 3H), 2.62 (m, 2H), 2.61 (s, H), 2.34 (d, J = 12.9 Hz, 3H) |
| 26 | 331.4 | (methanol-$d_4$): 8.77 (s, 1H), 8.08 (s, 2H), 3.54 (m, 4H), 3.44 (t, J = 6 Hz, 2H), 2.52 (s, 3H), 1.21 (s, J = 6.0 Hz, 3H) |
| 27 | 417.5 | (methanol-$d_4$): 9.00 (s, 1H), 8.77 (d, J = 5.4 Hz, 2H), 8.06 (d, J = 5.5 Hz, 2H), 7.53 (s, 1H), 6.1 (t, J = 51 Hz, 1H), 4.73 (t, J = 15 Hz, 2H), 3.58 (m, 2H), 3.00 (m, 2H), 2.50 (s, 3H) |
| 28 | 413.4 | |
| 29 | 317.4 | |
| 30 | 341.3 | |
| 31 | 298.0 | |
| 32 | 341.4 | (DMSO-$d_6$): 12.82 (s, 1H), 8.85 (d, J = 6.7 Hz, 2H), 8.04 (d, J = 6.6 Hz, 2H), 4.27 (dt, J = 14.3, 8.6 Hz, 2H), 3.98 (dt, J = 15.2, 9.4 Hz, 2H), 3.76-3.61 (m, 1H), 2.51 (s, 3H), 1.76 (s, 3H) |
| 33 | 315.4 | (DMSO-$d_6$): 12.65 (s, 1H), 8.75 (dd, J = 5.1, 1.4 Hz, 2H), 8.31 (t, J = 5.7 Hz, 1H), 7.82 (d, J = 6.5 Hz, 2H), 4.00 (d, J = 5.8 Hz, 2H), 2.47 (s, 3H), 1.87 (s, 3H) |
| 34 | 358.4 | (DMSO-$d_6$): 12.48 (s, 1H), 8.65 (d, J = 5.6 Hz, 2H), 7.59 (d, J = 6.0 Hz, 2H), 4.05 (q, J = 7.1 Hz, 2H), 2.43 (s, 3H), 2.35 (t, J = 7.3 Hz, 2H), 1.85 (p, J = 7.3 Hz, 2H), 1.18 (t, J = 7.1 Hz, 3H) |
| 35 | 344.4 | (DMSO-$d_6$): 12.54 (s, 1H), 8.76 (d, J = 6.8 Hz, 1H), 7.79 (d, J = 6.2 Hz, 1H), 3.59 (s, 3H), 2.46 (s, 3H), 2.37 (t, J = 7.4 Hz, 2H), 1.96-1.80 (m, 2H) |
| 36 | 327.3 | (DMSO-$d_6$): 12.74 (s, 1H), 8.68 (d, J = 6.3 Hz, 2H), 7.88 (s, 1H), 7.67 (d, J = 6.1 Hz, 2H), 4.35 (dd, J = 8.4, 4.1 Hz, 2H), 2.71 (d, J = 10.6 Hz, 1H), 2.44 (s, 3H), 2.40-1.79 (m, 4H) |
| 37 | 379.0 | |
| 38 | 391.0 | |
| 39 | 395.0 | |
| 40 | 407.0 | |
| 41 | 409.0 | |
| 42 | 393.0 | |
| 43 | 357.3 | |
| 44 | 371.4 | |
| 45 | 359.3 | |
| 46 | 413.3 | |
| 47 | 345.2 | |
| 48 | 397.3 | |
| 49 | 397.3 | |
| 50 | 364.4 | |
| 51 | 350.5 | |
| 52 | 350.4 | |
| 53 | 399.2 | |
| 54 | 397.4 | |
| 55 | 387.5 | |
| 56 | 303.3 | |
| 57 | 373.5 | |
| 58 | 379.5 | |
| 59 | 392.0 | |
| 60 | 372.0 | |
| 61 | 372.0 | |
| 62 | 358.0 | |
| 63 | 384.0 | |
| 64 | 377.0 | |
| 65 | 328.0 | |
| 66 | 342.0 | |
| 67 | 346.4 | (methanol-$d_4$): 8.74 (d, J = 5.7 Hz, 2H), 8.00 (d, J = 6.6 Hz, 2H), 4.37 (t, J = 3 Hz, 2H), 3.70 (t, J = 3.3 Hz, 2H), 3.46 (T, J = 6.6 Hz, 2H), 2.49 (s, 3H), 1.57 (m, 2H), 0.92 (t, J = 7.5 Hz, 3H) |
| 68 | 407.5 | |
| 69 | 357.5 | |
| 70 | 385.5 | |
| 71 | 381.0 | |
| 72 | 395.0 | |
| 73 | 399.0 | |
| 74 | 419.0 | |
| 76 | 404.0 | |
| 77 | 387.0 | |
| 78 | 349.3 | |
| 79 | 391.4 | |
| 80 | 415.5 | |
| 81 | 364.4 | (methanol-$d_4$): 8.75 (d, J = 6.7 Hz, 1H), 7.99 (d, J = 6.7 Hz, 1H), 7.54-7.22 (m, 2H), 4.71 (s, 1H), 4.28 (s, 1H), 2.55 (s, 1H) |

TABLE 2-continued

| Compound No. | ESMS (M + H) | ¹H NMR (300 MHz, unless indicated otherwise) NMR peaks given as δ values |
|---|---|---|
| 82 | 350.4 | (methanol-$d_4$): 8.77 (d, J = 6.8 Hz, 1H), 8.25-7.94 (m, 1H), 7.45-7.25 (m, 1H), 7.12-6.91 (m, 1H), 4.84 (s, 1H), 2.54 (s, 2H) |
| 84 | 450.8 | (DMSO-$d_6$): 10.97 (s, 1H), 9.12 (s, 1H), 7.65-7.56 (m, 3H), 7.43-7.28 (m, 2H), 7.07-7.03 (m, 1H), 6.66-6.30 (tt, 1H), 4.82-4.71 (td, 2H), 3.49-3.38 (m, 2H), 2.89-2.85 (t, 2H), 2.36 (s, 3H) |
| 85 | 416.2 | (DMSO-$d_6$): 10.89 (s, 1H), 9.12 (s, 1H), 7.56 (s, 1H), 7.52-7.39 (m, 5H), 7.03-6.99 (m, 1H), 6.66-6.48 (tt, 1H), 4.81-4.71 (td, 2H), 3.43 (m, 2H), 2.89-2.85 (m, 2H), 2.33 (s, 3H) |
| 86 | 412.4 | |
| 87 | 391.5 | |
| 88 | 399.4 | |
| 89 | 461.5 | |
| 90 | 386.00 | (DMSO-$d_6$): 11.2 (m exch, 1H), 8.08 (d, 2H), 7.92 (d, 2HH), 7.5 (s, 1H), 5.7 (t, 1H). 3.3 (dt, 2H), 2.4 (s, 3H), 2.25 (t, 2H), 1.25 (s, 9H) |
| 91 | 360.60 | (DMSO-$d_6$): 10.9 (s, 1H), 8.9 (s, 1H), 7.9 (s, 1H), 6.75 (t, 1H), 3.8 (s, 3H), 3.4 (m, 2H), 3.3 (m, 2H), 3.25 (d, 2H), 2.3 (s, 3H), 1.0 (m, 1H), 0.5 (m, 2H), 0.2 (m, 2H) |
| 92 | 416.7 | (DMSO-$d_6$): 10.62 (s, 1H), 7.06 (m, 2H), 6.97 (d, J = 8.1 Hz, 1H), 6.66 (t, J = 5.4 Hz, 1H), 3.78 (s, 6H), 3.45 (d, J = 5.3 Hz, 2H), 3.28 (dd, J = 11.3, 6.2 Hz, 4H), 2.31 (s, 3H), 1.05-0.95 (m, 1H), 0.47 (dd, J = 8.1, 1.8 Hz, 2H), 0.18 (dd, J = 4.8, 1.5 Hz, 2H) |
| 93 | 386.6 | (DMSO-$d_6$): 10.76-10.59 (s, 1H), 7.35-7.27 (m, 1H), 7.07 (dd, J = 8.6, 5.1 Hz, 2H), 6.97 (dd, J = 8.3, 2.5 Hz, 1H), 6.69 (t, J = 5.2 Hz, 1H), 3.78 (s, 3H), 3.45 (d, J = 5.3 Hz, 2H), 3.28 (dd, J = 11.3, 6.2 Hz, 4H), 2.33 (s, 3H), 0.98 (m, 1H), 0.53-0.40 (m, 2H), 0.22-0.13 (m, 2H) |
| 94 | 416.7 | (DMSO-$d_6$): 10.66 (s, 1H), 6.66 (m, 3H), 6.52 (t, J = 2.3 Hz, 1H), 3.76 (s, 6H), 3.46 (m, 2H), 3.34-3.22 (m, 4H), 2.33 (s, 3H), 0.99 (m, 1H), 0.50-0.42 (m, 2H), 0.21-0.14 (m, 2H) |
| 95 | 408.6 | (DMSO-$d_6$): 10.76 (s, 1H), 8.97 (dd, J = 10.4 Hz, 2H), 8.22 (d, J = 1.6 Hz, 1H), 8.10 (d, J = 8.7 Hz, 1H), 7.93 (dd, J = 8.7, 1.8 Hz, 1H), 6.70 (t, 1H), 3.47 (m, 2H), 3.27 (m, 4H), 2.40 (s, 3H), 1.01 (m, 1H), 0.52-0.43 (m, 2H), 0.19 (m, 2H) |
| 96 | 417.7 | (DMSO-$d_6$): 10.66 (s, 1H), 7.89 (d, J = 1.8 Hz, 1H), 7.40 (d, J = 1.8 Hz, 1H), 6.66 (t, 1H), 3.89 (s, 3H), 3.82 (s, 3H), 3.46 (t, J = 5.5 Hz, 2H), 3.34-3.23 (m, 4H), 2.33 (s, 3H), 2.31 (s, 1.5H), 1.00 (m, 1H), 0.51-0.41 (m, 2H), 0.22-0.13 (m, 2H) |
| 97 | 371.5 | |
| 98 | 370.4 | |
| 98 | 371.5 | (methanol-$d_4$): 8.73 (d, J = 6.0 HZ, 2H), 8.03 (d, J-6.0 Hz, 2H), 3.62 (m, 1H), 3.39-3.30 (m, 3H), 3.15 (m, 1H), 2.48 (s, 3H), 1.15 (d, J = 6.0 HZ, 3H), 0.90 (m, 1H), 0.49 (m, 2H), 0.01 (m, 2H) |
| 100 | 385.8 | |
| 101 | 411.6 | |
| 102 | 393.7 | |
| 103 | 372.7 | |
| 104 | 292.3 | (DMSO-$d_6$): 12.42 (s, 1H), 8.59 (d, J = 2.0 Hz, 1H), 8.02 (dd, J = 8.3, 2.2 Hz, 1H), 7.58 (d, J = 8.3 Hz, 1H), 2.41 (s, 3H), 2.16 (s, 3H) |
| 105 | 391.4 | (methanol-$d_4$): 8.49 (d, J = 2.2 Hz, 1H), 7.90 (dd, J = 8.3, 2.3 Hz, 1H), 7.48 (d, J = 8.3 Hz, 1H), 3.58 (t, J = 5.2 Hz, 2H), 3.43 (t, J = 5.2 Hz, 2H), 2.41 (s, 3H), 1.06 (m, 1H), 0.52 (q, J = 5.8 Hz, 2H), 0.22 (q, J = 4.7 Hz, 2H) |
| 106 | 391.4 | (methanol-$d_4$): 8.32 (d, J = 3.0 Hz, 1H), 7.98 (dd, J = 7.7, 1.7 Hz, 1H), 7.40 (dd, J = 7.6, 5.0 Hz, 1H), 3.58 (t, J = 5.3 Hz, 2H), 3.44 (t, J = 5.3 Hz, 2H), 3.35 (s, 2H), 2.44 (s, 3H), 1.06 (m, 1H), 0.52 (dd, J = 12.3, 5.9 Hz, 2H), 0.22 (dd, J = 10.7, 4.6 Hz, 2H) |
| 107 | 387.4 | (DMSO-$d_6$): 10.79 (br.s, 1H), 8.40 (br. s, 2H), 7.60 (s, 1H), 6.76 (s, 1H), 3.87 (s, 3H), 3.46 (t, J = 5.2 Hz, 2H), 3.30 (q, J = 5.3 Hz, 2H), 3.26 (d, J = 6.7 Hz, 2H), 2.36 (s, 3H), 1.00 (m, 1H), 0.46 (q, J = 7.4 Hz, 2H), 0.18 (q, J = 4.6 Hz, 2H) |
| 108 | 388.6 | (DMSO-$d_6$): 10.72 (s, 1H), 8.79 (s, 2H), 6.69 (t, 1H), 3.97 (s, 3H), 3.46 (t, 2H), 3.29 (m, 4H), 2.33 (s, 3H), 1.00 (m, 1H), 0.46 (m, 2H), 0.18 (m, 2H) |
| 109 | 387.6 | (DMSO-$d_6$): 10.79 (s, 1H), 8.17 (d, 1H), 7.05 (dd, 1H), 6.91 (s, 1H), 6.70 (t, 1H), 3.86 (s, 3H), 3.46 (t, 2H), 3.29 (m, 4H), 2.35 (s, 3H), 0.99 (m, 1H), 0.46 (m, 2H), 0.18 (m, 2H) |
| 110 | 387.6 | |
| 111 | 435.6 | (DMSO-$d_6$): 10.75 (s, 1H), 8.11 (d, 1H), 7.70 (d, 1H), 6.70 (t, 1H), 4.21 (q, 2H), 3.46 (t, 2H), 3.29 (m, 4H), 2.36 (s, 3H), 1.37 (t, 3H). 0.98 (m, 1H), 0.46 (m, 2H), 0.18 (m, 2H) |
| 112 | 288.3 | (DMSO-$d_6$): 12.30 (s, 1H), 8.28 (d, J = 2.8 Hz, 1H), 8.25 (d, J = 1.6 Hz, 1H), 7.47 (t, 1H), 3.89 (s, 3H), 2.32 (s, 3H), 2.16 (s, 3H) |

TABLE 2-continued

| Compound No. | ESMS (M + H) | $^1$H NMR (300 MHz, unless indicated otherwise) NMR peaks given as δ values |
|---|---|---|
| 113 | 407.5 | (DMSO-$d_6$): 11.12 (s, 1H), 9.08 (d, J = 5.2 Hz, 1H), 8.37 (d, J = 8.2 Hz, 1H), 8.24 (d, J = 8.4 Hz, 1H), 8.04 (t, J = 7.1 Hz, 1H), 7.96 (d, J = 5.1 Hz, 1H), 7.95-7.85 (m, 1H), 6.92 (t, J = 5.4 Hz, 1H), 3.48 (t, J = 5.5 Hz, 2H), 3.33 (dd, J = 11.0, 5.6 Hz, 2H), 3.27 (d, J = 6.8 Hz, 2H), 2.53 (d, J = 4.1 Hz, 2H), 1.08-0.91 (m, 1H), 0.52-0.37 (m, 2H), 0.25-0.12 (m, 2H) |
| 114 | 351.3 | |
| 115 | 425.4 | (DMSO-$d_6$): 10.77 (s, 1H), 9.01 (s, 1H), 8.93 (s, 1H), 8.42 (s, 1H), 6.68 (t, 1H), 3.46 (m, 2H), 3.27 (m, 4H), 2.38 (s, 3H), 1.00 (m, 1H), 0.47 (m, 2H), 0.19 (m, 2H) |
| 116 | 360.4 | (DMSO-$d_6$): 10.74 (s, 1H), 7.49 (d, 1H), 6.69 (t, 1H), 6.59 (d, 1H) 3.89 (s, 3H), 3.46 (m, 2H), 3.29 (m, 4H), 2.33 (s, 3H), 0.98 (m, 1H), 0.47 (m, 2H), 0.18 (m, 2H) |
| 117 | 385.4 | |
| 118 | 371.4 | |
| 119 | 421.4 | 1H NMR (300 MHz, CDCl3) d 8.95 (s, 1H), 8.36-8.09 (m, 2H), 8.01 (s, 1H), 7.81 (d, J = 7.5 Hz, 1H), 7.49 (s, 1H), 3.82-3.45 (m, 3H), 3.44-3.16 (m, 3H), 2.50 (s, 3H), 1.37-0.91 (m, 4H), 0.55 (dt, J = 5.4, 4.9 Hz, 2H), 0.35-0.09 (m, 2H). |
| 120 | 401.2 | (methanol-$d_4$): 8.30 (s, 2H), 7.83-7.35 (m, 5H), 3.91 (s, 3H), 3.75-3.51 (m, 1H), 3.47-3.25 (m, 9H), 3.16 (dd, J = 13.8, 6.6 Hz, 1H), 2.39 (s, 3H), 1.15 (d, J = 6.2 Hz, 3H), 1.10-0.92 (m, 1H), 0.61-0.42 (m, 2H), 0.34-0.13 (m, 2H). |
| 121 | 422.2 | (CDCl$_3$): 8.85 (dd, J = 13.3, 1.8 Hz, 2H), 8.22 (d, J = 1.6 Hz, 1H), 8.07 (d, J = 8.7 Hz, 1H), 7.83 (dd, J = 8.7, 1.8 Hz, 1H), 3.67 (ddd, J = 36.5, 19.9, 16.4 Hz, 2H), 3.47-3.08 (m, 3H), 2.51 (s, 3H), 1.23 (t, J = 8.9 Hz, 3H), 1.09 (s, 1H), 0.55 (dt, J = 5.6, 5.1 Hz, 2H), 0.35-0.06 (m, 2H). |
| 122 | 431.3 | (methanol-$d_4$): 7.83 (d, J = 1.8 Hz, 1H), 7.28 (d, J = 1.8 Hz, 1H), 3.96 (s, 3H), 3.86 (s, 3H), 3.71-3.53 (m, 1H), 3.47-3.26 (m, 14H), 3.23-3.03 (m, 1H), 2.37 (s, 3H), 1.15 (d, J = 6.2 Hz, 3H), 1.11-0.94 (m, 1H), 0.51 (dd, J = 8.1, 1.6 Hz, 2H), 0.21 (s, 2H). |
| 123 | 371.4 | |
| 124 | 401.4 | (CDCl$_3$): 8.13 (d, J = 5.3 Hz, 1H), 6.91 (d, J = 5.3 Hz, 1H), 6.80 (s, 1H), 3.95 (s, 3H), 3.77-3.45 (m, 2H), 3.46-3.09 (m, 3H), 2.45 (s, 3H), 1.32-0.88 (m, 4H), 0.65-0.41 (m, 2H), 0.21 (q, J = 4.8 Hz, 2H). |
| 125 | 401.4 | (CDCl$_3$): 8.13 (d, J = 5.3 Hz, 1H), 6.91 (d, J = 5.3 Hz, 1H), 6.80 (s, 1H), 3.95 (s, 3H), 3.77-3.45 (m, 2H), 3.46-3.09 (m, 3H), 2.45 (s, 3H), 1.32-0.88 (m, 4H), 0.65-0.41 (m, 2H), 0.21 (q, J = 4.8 Hz, 2H). |
| 126 | 375.4 | (DMSO-$d_6$): 10.90 (m, 1H), 8.25 (d, J = 5.2 Hz, 1H), 7.44 (d, J = 5.2 Hz, 1H), 7.33 (s, 1H), 6.75 (m, 1H), 3.46 (t, J = 5.5 Hz, 2H), 3.30 (t, J = 5.0 Hz, 2H), 3.26 (d, J = 6.8 Hz, 2H), 2.34 (s, 3H), 1.13-0.86 (m, 1H), 0.55-0.40 (m, 2H), 0.18 (q, J = 4.9 Hz, 2H). |
| 127 | 357.3 | |
| 128 | 407.4 | (DMSO-$d_6$): 10.87 (m, 1H), 9.05 (d, J = 2.0 Hz, 1H), 8.69 (d, J = 1.8 Hz, 1H), 8.06 (dd, J = 12.2, 8.1 Hz, 2H), 7.85 (t, J = 7.1 Hz, 1H), 7.71 (t, J = 7.4 Hz, 1H), 6.83 (t, J = 5.4 Hz, 1H), 3.47 (t, J = 5.5 Hz, 2H), 3.40-3.29 (m, 2H), 3.27 (d, J = 6.8 Hz, 2H), 2.41 (s, 3H), 1.12-0.85 (m, 1H), 0.58-0.35 (m, 2H), 0.33-0.05 (m, 2H). |
| 129 | 375.4 | (DMSO-$d_6$): 10.91 (s, 1H), 8.73 (s, 2H), 7.7 (m, 2H), 6.76 (m, 1H), 3.46 (t, J = 5.5 Hz, 2H), 3.40-3.28 (m, 2H), 3.26 (d, J = 6.8 Hz, 2H), 2.37 (s, 3H), 0.99 (m, 1H), 0.53-0.40 (m, 2H), 0.18 (q, J = 4.9 Hz, 2H). |
| 130 | 408.4 | (DMSO-$d_6$): 10.83 (m, 1H), 9.20 (m, 1H), 8.72 (s, 1H), 8.52 (d, J = 8.2 Hz, 1H), 7.76 (m, 1H), 6.78 (t, J = 5.3 Hz, 1H), 3.47 (t, J = 5.5 Hz, 2H), 3.31 (dd, J = 11.1, 5.5 Hz, 2H), 3.27 (d, J = 6.8 Hz, 2H), 2.41 (s, 3H), 1.12-0.90 (m, 1H), 0.55-0.39 (m, 2H), 0.18 (dd, J = 6.1, 4.6 Hz, 2H). |
| 131 | 409.4 | (DMSO-$d_6$): 10.74 (m, 1H), 9.0 (m, 2H), 8.52 (s, 1H), 7.79-7.25 (m, 2H), 6.64 (s, 1H), 3.34-3.25 (m, 2H), 3.14 (dd, J = 10.7, 5.3 Hz, 2H), 3.09 (d, J = 6.8 Hz, 2H), 2.25 (s, 3H), 0.94-0.66 (m, 1H), 0.39-0.23 (m, 2H), 0.08--0.02 (m, 2H). |
| 132 | 414.4 | (DMSO-$d_6$): 10.68 (s, 1H), 8.49 (s, 1H), 8.12 (d, J = 8.7 Hz, 1H), 7.90 (d, J = 8.6 Hz, 1H), 6.74 (t, J = 5.3 Hz, 1H), 3.46 (t, J = 5.4 Hz, 2H), 3.30 (dd, J = 10.0, 4.4 Hz, 2H), 3.26 (d, J = 6.8 Hz, 2H), 2.33 (s, 3H), 2.11 (s, 3H), 1.07-0.91 (m, 1H), 0.54-0.40 (m, 2H), 0.24-0.14 (m, 2H). |
| 133 | 387.4 | (DMSO-$d_6$): 10.83 (s, 1H), 7.73 (dd, J = 18.1, 7.2 Hz, 1H), 6.48 (d, J = 1.7 Hz, 1H), 6.24 (dt, J = 16.7, 8.3 Hz, 1H), 3.46 (t, J = 5.5 Hz, 2H), 3.41 (s, 3H), 3.30 (dd, J = 10.8, 5.4 Hz, 2H), 3.26 (d, J = 6.8 Hz, 2H), 2.34 (s, 3H), 1.17-0.81 (m, 1H), 0.58-0.37 (m, 2H), 0.26-0.10 (m, 2H). |

TABLE 2-continued

| Compound No. | ESMS (M + H) | ¹H NMR (300 MHz, unless indicated otherwise) NMR peaks given as δ values |
|---|---|---|
| 134 | 387.3 | (DMSO-$d_6$): 10.80 (s, 1H), 7.72 (dd, J = 8.3, 7.4 Hz, 1H), 7.21 (d, J = 7.2 Hz, 1H), 6.83 (t, J = 8.3 Hz, 1H), 3.87 (s, 3H), 3.46 (t, J = 5.5 Hz, 2H), 3.37-3.28 (m, 2H), 3.26 (d, J = 6.8 Hz, 2H), 2.35 (s, 3H), 1.10-0.90 (m, 1H), 0.65-0.37 (m, 2H), 0.25-0.08 (m, 2H). |
| 135 | 418.3 | (DMSO-$d_6$): 10.73 (s, 1H), 7.96 (s, 1H), 3.94 (s, 3H), 3.93 (s, 3H), 3.46 (t, J = 5.5 Hz, 2H), 3.39-3.29 (m, 2H), 3.26 (d, J = 6.8 Hz, 2H), 2.33 (s, 3H), 0.97 (m, 1H), 0.54-0.37 (m, 2H), 0.24-0.10 (m, 2H). |
| 136 | 359.4 | (methanol-$d_4$): 8.73 (d, J = 6.0 Hz, 2H), 8.03 (d, J = 6.00 HZ, 2H), 3.50-3.14 (m, 5H), 2.48s, 3H), 1.57 (m, 2H), 1.15 (d, J = 6.0 HZ, 3H), 0.93 (t, J = 6.0 Hz, 3H) |
| 137 | 389.4 | |
| 138 | 417.5 | |
| 139 | 409.4 | (DMSO-$d_6$): 10.98 (s, 1H), 8.43 (s, 1H), 7.53 (s, 1H), 6.84 (t, J = 5.1 Hz, 1H), 3.47 (t, J = 5.4 Hz, 2H), 3.32 (t, J = 5.3 Hz, 2H), 3.26 (d, J = 6.8 Hz, 2H), 2.41 (s, 3H), 1.13-0.93 (m, 1H), 0.61-0.41 (m, 2H), 0.31-0.13 (m, 2H). |
| 140 | 391.4 | (DMSO-$d_6$): 10.82 (s, 1H), 8.45 (d, J = 1.8 Hz, 1H), 8.19 (dd, J = 9.4, 1.9 Hz, 1H), 3.46 (t, J = 5.5 Hz, 2H), 3.30 (dd, J = 10.3, 4.8 Hz, 2H), 3.26 (d, J = 6.8 Hz, 2H), 2.36 (s, 3H), 1.12-0.88 (m, 1H), 0.52-0.40 (m, 2H), 0.23-0.12 (m, 2H). |
| 141 | 409.4 | (DMSO-$d_6$): 10.82 (s, 1H), 8.45 (d, J = 1.8 Hz, 1H), 8.19 (dd, J = 9.4, 1.9 Hz, 1H), 6.74 (t, J = 5.3 Hz, 1H), 3.46 (t, J = 5.5 Hz, 2H), 3.37-3.28 (m, 2H), 3.26 (d, J = 6.8 Hz, 2H), 2.34 (s, 3H), 1.11-0.87 (m, 1H), 0.58-0.35 (m, 2H), 0.21-0.10 (m, 2H). |
| 142 | 396.4 | (DMSO-$d_6$): 11.94 (s, 1H), 8.17 (s, 1H), 7.55 (d, J = 3.3 Hz, 1H), 6.74 (s, 1H), 6.52 (s, 1H), 3.46 (t, J = 5.5 Hz, 2H), 3.39-3.15 (m, 4H), 2.31 (s, 3H), 0.97 (m, 1H), 0.58-0.36 (m, 2H), 0.29-0.13 (m, 2H). |
| 143 | 409.4 | (DMSO-$d_6$): 10.89 (s, 1H), 8.53 (s, 1H), 7.82 (d, J = 5.2 Hz, 1H), 6.70 (s, 1H), 3.46 (t, J = 5.4 Hz, 2H), 3.31 (m, 2H), 3.26 (d, J = 6.8 Hz, 2H), 2.38 (s, 3H), 1.17-0.85 (m, 1H), 0.57-0.35 (m, 2H), 0.18 (d, J = 4.9 Hz, 2H). |
| 144 | 396.4 | (DMSO-$d_6$): 10.86 (s, 1H), 9.23 (s, 1H), 8.26 (m, 2H), 7.99 (s, 2H), 6.81 (t, J = 5.4 Hz, 1H), 3.46-3.11 (m, 6H), 2.32 (s, 3H), 0.97 (dt, J = 14.7, 7.1 Hz, 1H), 0.58-0.30 (m, 2H), 0.29-0.11 (m, 2H). |
| 145 | 317.2 | |
| 146 | 434.4 | (DMSO-$d_6$): 12.34 (s, 1H), 10.72 (m, 1H), 6.75 (t, 1H), 3.46 (t, J = 5.4 Hz, 1H), 3.27 (m, 1H), 3.26 (d, J = 6.8 Hz, 1H), 2.35 (s, 3H), 2.29 (s, 3H), 2.15 (s, 3H), 0.97 (dd, J = 11.5, 7.4 Hz, 1H), 0.46 (dt, J = 5.6, 5.1 Hz, 2H), 0.29-0.13 (m, 2H). |
| 147 | 389.4 | (methanol-$d_4$): 8.41 (brs, 1H), 8.35 (brs, 1H), 7.84 (d, J = 3.0 HZ, 1H), 3.98 (s, 3H), 3.30-3.60 (m, 4H), 3.16 (m, 1H), 2.41 (s, 3H), 1.60 (m, 2H), 1.15 (d, J = 6.0 Hz, 3H), 0.94 (t, J = 6 HZ, 3H). |
| 148 | 347.2 | |
| 149 | 361.3 | (methanol-$d_4$): 8.62 (s, 1H), 8.54 (d, J = 2.5 Hz, 1H), 8.28 (dd, J = 2.6, 1.4 Hz, 1H), 3.58 (d, J = 4.0 Hz, 1H), 3.41 (dd, J = 13.7, 3.8 Hz, 1H), 3.13 (dd, J = 13.7, 7.4 Hz, 1H), 1.66-1.37 (m, 2H), 0.98 (t, J = 7.4 Hz, 3H). |
| 150 | 398.3 | (DMSO-$d_6$): 7.96 (s, 2H), 7.46 (s, 2H), 7.04 (s, 1H), 3.52 (m, 2H), 3.14 (t, 6.2 HZ, 2H), 2.81 (q, J = 7.5 Hz, 2H), 2.43 (s, 3H), 1.22 (t, J = 7.5 HZ, 3H). |
| 151 | 428.3 | |
| 152 | 381 | |
| 153 | 407.3 | |
| 154 | 430.3 | |
| 155 | 392 | |
| 156 | 451.3 | (DMSO-$d_6$): 8.58 (d, J = 4.9 Hz, 1H), 7.77 (s, 1H), 7.46 (d, J = 6.0 Hz, 1H), 6.77 (s, 1H), 6.33 (m, 1H), 4.48 (dd, J = 16.0, 12.9 Hz, 2H), 3.39 (m, 2H), 2.64 (t, J = 7.0 Hz, 1H), 2.36 (s, 1H). |
| 157 | 440 | |
| 158 | 440 | |
| 159 | 414 | |
| 160 | 415.3 | (CDCl$_3$): 8.57 (d, J = 6.0 Hz, 2H), 7.42 (s, 1H), 7.31 (d, J = 6.0 Hz, 2H), 3.94 (q, J = 7.3 Hz, 2H), 3.63 (m, 2H), 2.78 (m, 2H), 2.41 (s, 3H), 1.42 (t, J = 7.3 Hz, 3H). |
| 161 | 429 | (DMSO-$d_6$): 8.55 (d, J = 6.0 Hz, 1H), 7.42 (d, J = 5.9 Hz, 1H), 3.86 (q, J = 7.2 Hz, 1H), 2.65-2.50 (m, 2H), 2.30 (d, J = 5.0 Hz, 3H), 1.42-1.01 (m, 2H). |
| 162 | 367.5 | (methanol-$d_4$): 8.52 (dd, J = 4.7, 1.5 Hz, 1H), 7.62 (s, 1H), 7.46 (m, 3H), 4.29 (s, 2H), 4.14 (q, J = 7.3 Hz, 2H), 2.48 (s, 3H), 1.42 (t, J = 7.3 Hz, 2H). |

TABLE 2-continued

| Compound No. | ESMS (M + H) | $^1$H NMR (300 MHz, unless indicated otherwise) NMR peaks given as δ values |
|---|---|---|
| 163 | 416.4 | (CDCl$_3$): 8.57 (d, J = 6.0 Hz, 2H), 7.30 (d, J = 6.0 Hz, 2H), 3.54-3.69 (m, 10H), 2.59 (t, J = 6.0 Hz, 2H), 2.49 (m, 4H), 2.42 (s, 3H) |
| 164 | 440 | |
| 165 | 481 | |
| 166 | 420 | |

Biological Assay of Compounds of the Invention

EXAMPLE 28

PI3K Inhibition Assay

Using a Biomek FX from Beckman Coulter, 1.5 µL of each of ten 2.5-fold serial dilutions of a compound of the invention in 100% DMSO was added to an individual well (hereafter, "test well") in a 96 well polystyrene plate [Corning, Costar Item No. 3697]. One test well also contained 1.5 µL of DMSO with no compound. Another well contained an inhibitor in DMSO at a concentration known to completely inhibit the enzyme, (hereafter "background well"). Using a Titertek Multidrop, 50 µL of Reaction Mix [100 mM HEPES pH 7.5, 50 mM NaCl, 10 mM DTT, 0.2 mg/mL BSA, 60 µM phosphatidylinositol(4,5)bisphosphate diCl6 (PI(4,5)P$_2$; Avanti Polar Lipids, Cat. No. 840046P) and PI3K isoform of interest (see Table 3 for isoform concentrations)] was added to each well. To initiate the reaction, 50 µL of ATP Mix [20 mM MgCl$_2$, 6 µM ATP (100 µCi/µmole $^{33}$P-ATP)] was added each well, followed by incubating the wells for 30 min. at 25° C. Final concentrations in each well were 50 mM HEPES 7.5, 10 mM MgCl$_2$, 25 mM NaCl, 5 mM DTT, 0.1 mg/mL BSA, 30 µM PI(4,5)P$_2$, 3 µM ATP, and the PI3K isoform of interest (see Table 3). Final compound concentrations in each well ranged from 10 µM to 1 nM.

TABLE 3

| PI3K Isoform Concentrations | PI3K-α | PI3K-β | PI3K-γ | PI3K-δ |
|---|---|---|---|---|
| Enzyme concentration in Reaction Mix | 4 nM | 20 nM | 4 nM | 4 nM |
| Final enzyme concentration | 2 nM | 10 nM | 2 nM | 2 nM |

After incubation, the reactions in each well were quenched by addition of 50 µL of stop solution [30% TCA/Water, 10 mM ATP]. Each quenched reaction mixture was then transferred to a 96 well glass fiber filter plate [Corning, Costar Item No. 3511]. The plate was vacuum-filtered and washed three times with 150 µL of 5% TCA/water in a modified Bio-Tek Instruments ELX-405 Auto Plate Washer. 50 µL of scintillation fluid was added to each well and the plate read on a Perkin-Elmer TopCount™ NXT liquid scintillation counter to obtain $^{33}$P-counts representing inhibition values.

The value for the background well was subtracted from the value obtained for each test well and the data were fit to the competitive tight binding Ki equation described by Morrison and Stone, *Comments Mol. Cell. Biophys.* 2: 347-368, 1985.

Each of compounds 1 to 166 had a Ki of less than 0.25 micromolar for the inhibition of PI3Kγ. Each of compounds 3-7, 14, 19-23, 26-27, 29, 31, 33, 37-38, 41-50, 52, 54-62, 64-73, 75, 77-78, 86-87, 90, 92, 95-96, 99, 106-109, 112-113, 117, 119-122, 124-127, 129-131, 135-140, 142-145, 147-158, 160-162, and 164-165 had a Ki of less than 0.050 micromolar for the inhibition of PI3Kγ.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound having the formula:

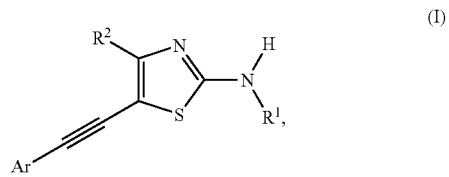

(I)

or a pharmaceutically acceptable salt thereof, wherein:
Ar is a phenyl ring or a 5-10 membered monocyclic or fused bicyclic heteroaryl ring having up to 2 atoms selected from nitrogen, wherein each ring is optionally substituted with up to 3 substituents independently selected from fluoro, chloro, C$_{1-4}$aliphatic, C$_{3-4}$cycloaliphatic, —OC$_{1-4}$aliphatic, —OC$_{3-4}$cycloaliphatic, —N(J$^{R1}$)C(O)C$_{1-4}$aliphatic, or N(J$^{R1}$)$_2$, wherein each of said aliphatic or cycloaliphatic is optionally substituted with up to 3 occurrences of fluoro;
R$^1$ is selected from —C(O)R$^{1a}$, —C(O)OR$^{1a}$, or —C(O)N(R$^{1a}$)(R$^{1b}$) wherein
R$^{1a}$ is C$_{1-4}$ aliphatic, C$_{3-6}$ cycloaliphatic, or C$_{5-10}$ heterocyclic having up to 2 atoms selected from oxygen, sulfur, or nitrogen, wherein R$^{1a}$ is optionally substituted with 1, 2, 3, or 4, occurrences of J$^R$;
each J$^R$ is independently fluoro, oxo, —C(O)J$^{R1}$, —C(O)N(J$^{R1}$)$_2$, —C(O)O(J$^{R1}$), —N(J$^{R1}$)C(O)J$^{R1}$, —OJ$^{R1}$, —SJ$^{R1}$, —S(O)J$^{R1}$, phenyl or a 5-10 membered heteroaryl or heterocyclyl ring having up to 2 atoms selected from nitrogen, oxygen, or sulfur, wherein said phenyl, heteroaryl, or heterocyclyl is optionally substituted with 1 or 2 J$^{R2}$ groups;
R$^{1b}$ is, independently, hydrogen, C$_{1-4}$aliphatic, C$_{3-6}$cycloaliphatic; or
R$^{1a}$ and R$^{1b}$, together with the nitrogen to which they are attached, form a 4-6 membered heterocyclic ring, wherein said heterocyclic ring optionally comprises one additional heteroatom selected from nitrogen and oxygen, and wherein said heterocyclic ring is optionally substituted with 1 or 2 J$^{R2}$ groups;
R$^2$ is C$_{1-4}$aliphatic optionally substituted with 1, 2, or 3 J$^{R2}$ groups;

each $J^{R1}$ is independently selected from hydrogen, $C_{1-4}$aliphatic, $C_{3-6}$cycloaliphatic, phenyl, benzyl, or 5-6 membered heteroaryl ring having up to two atom selected from nitrogen, oxygen, or sulfur, wherein each of said $C_{1-4}$aliphatic, phenyl, benzyl, or heteroaryl is optionally substituted with up to three $J^{R2}$ groups; and each $J^{R2}$ is, independently, selected from chloro, fluoro, —CN, —NO$_2$, oxo, $C_{1-4}$alkyl, $C_{3-6}$cycloalkyl, —OH, —OC$_{1-4}$alkyl, —OPhenyl, or —OCH$_2$Phenyl, wherein each of said alkyl, cycloalkyl or phenyl is optionally substituted with up to 3 fluoro groups.

2. The compound according to claim 1, or a pharmaceutically acceptable salt thereof, wherein Ar is an optionally substituted 5-10 membered heteroaryl ring.

3. The compound according to claim 2, or a pharmaceutically acceptable salt thereof, wherein Ar is an optionally substituted group selected from:

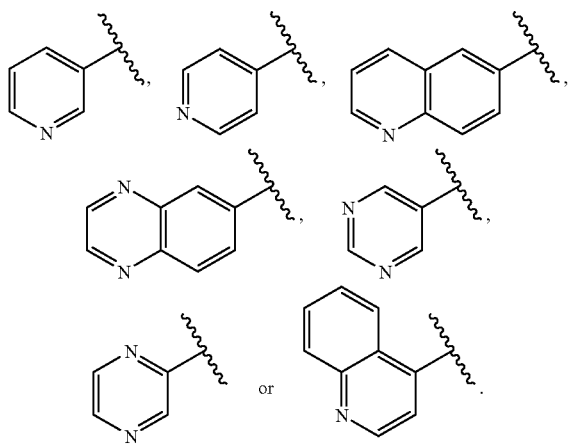

4. The compound according to claim 3, wherein Ar is substituted with 1 to 2 groups independently selected from —OCH$_3$, —OCF$_3$, —OCHF$_2$, Cl, F, or CF$_3$.

5. The compound according to claim 1, or a pharmaceutically acceptable salt thereof, wherein $R^2$ is CH$_3$.

6. The compound according to claim 1, or a pharmaceutically acceptable salt thereof, wherein $R^1$ is —C(O)N($R^{1a}$)($R^{1b}$).

7. The compound according to claim 6, or a pharmaceutically acceptable salt thereof, wherein $R^{1b}$ is hydrogen.

8. The compound according to claim 7, or a pharmaceutically acceptable salt thereof, wherein $R^{1a}$ is —CH$_2$CH(R)-$J^R$, wherein R is hydrogen or methyl and $J^R$ is —O$J^{R1}$ or a 5-membered heteroaryl having 2 nitrogen atoms and substituted with $C_{1-3}$alkyl or cyclopropyl, each optionally substituted with up to 3 fluoro groups.

9. The compound according to claim 8, or a pharmaceutically acceptable salt thereof, wherein $J^R$ is

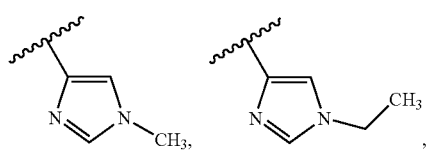

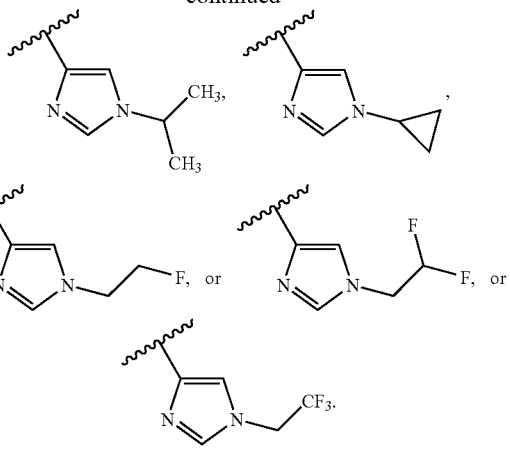

10. The compound according to claim 8, or a pharmaceutically acceptable salt thereof, wherein $J^R$ is —O$J^{R1}$ and $J^{R1}$ is $C_{1-4}$alkyl, optionally substituted with cyclopropyl or up to three fluoro or methyl groups.

11. The compound according to claim 10, or a pharmaceutically acceptable salt thereof, wherein $J^{R1}$ is —CH$_2$-cyclopropyl.

12. The compound according to claim 8, or a pharmaceutically acceptable salt thereof, wherein $J^R$ is —O$J^{R1}$ and $J^{R1}$ is phenyl or pyridyl, optionally substituted with up to three fluoro groups.

13. The compound according to claim 1, or a pharmaceutically acceptable salt thereof, wherein said compound is selected from

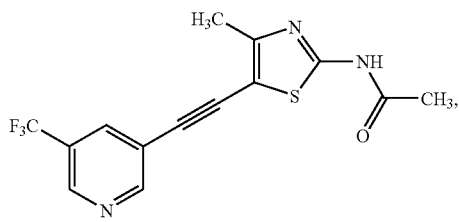

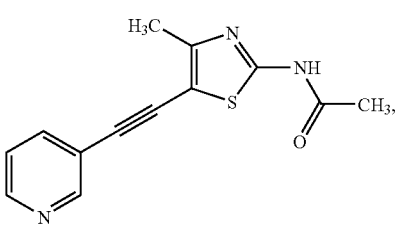

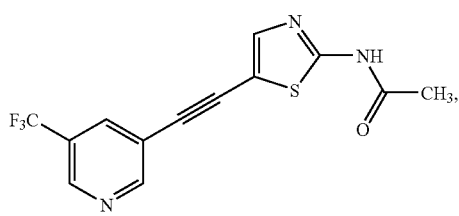

-continued
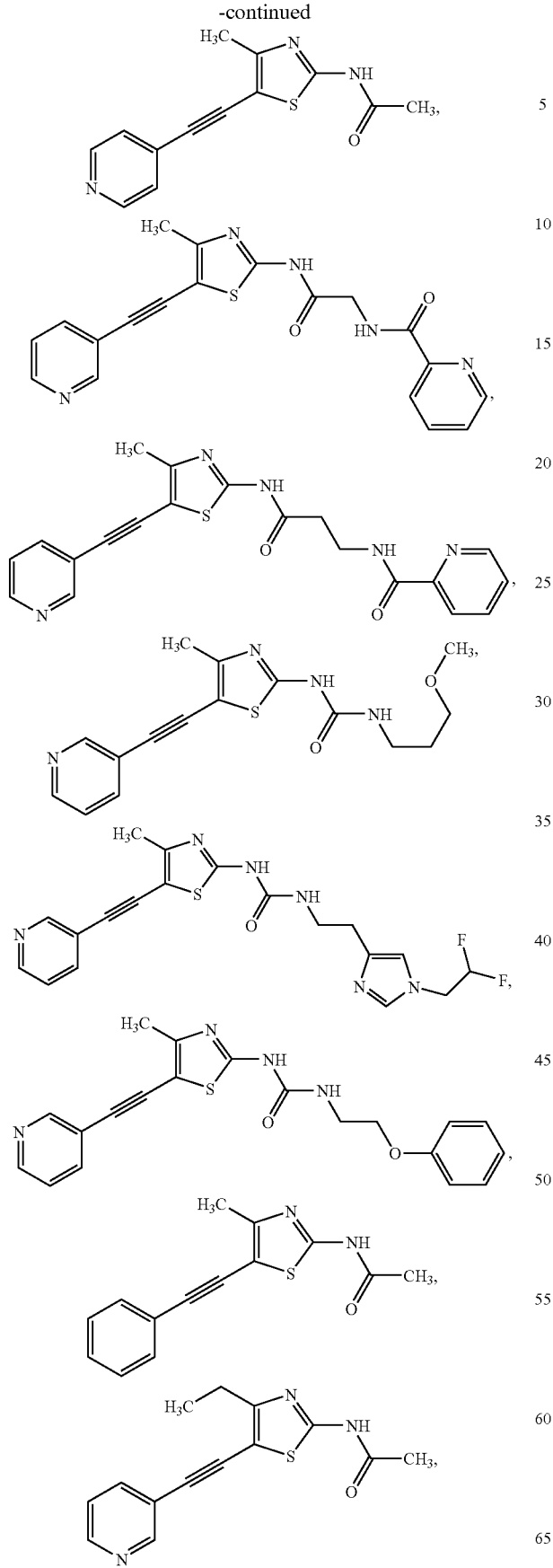
-continued
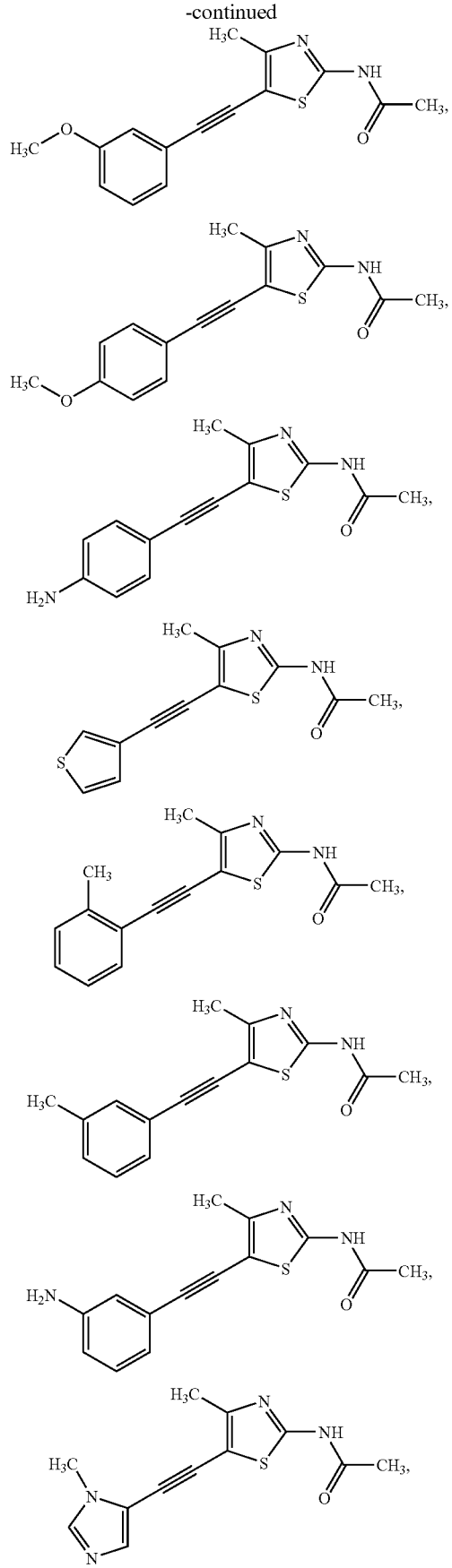

73
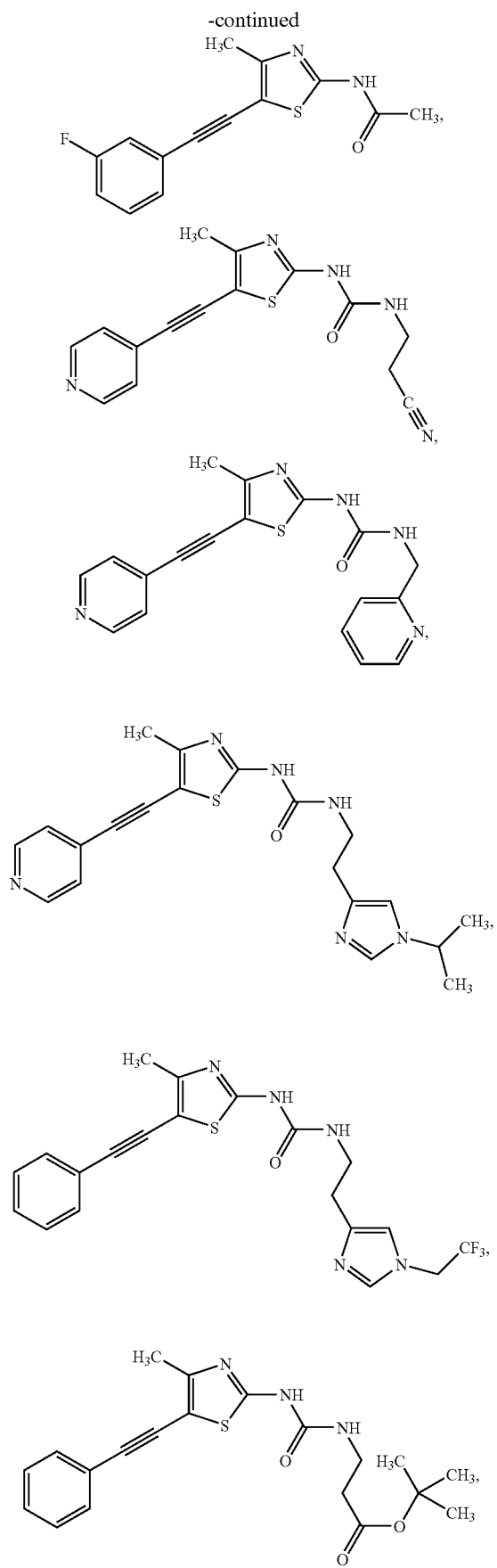
74
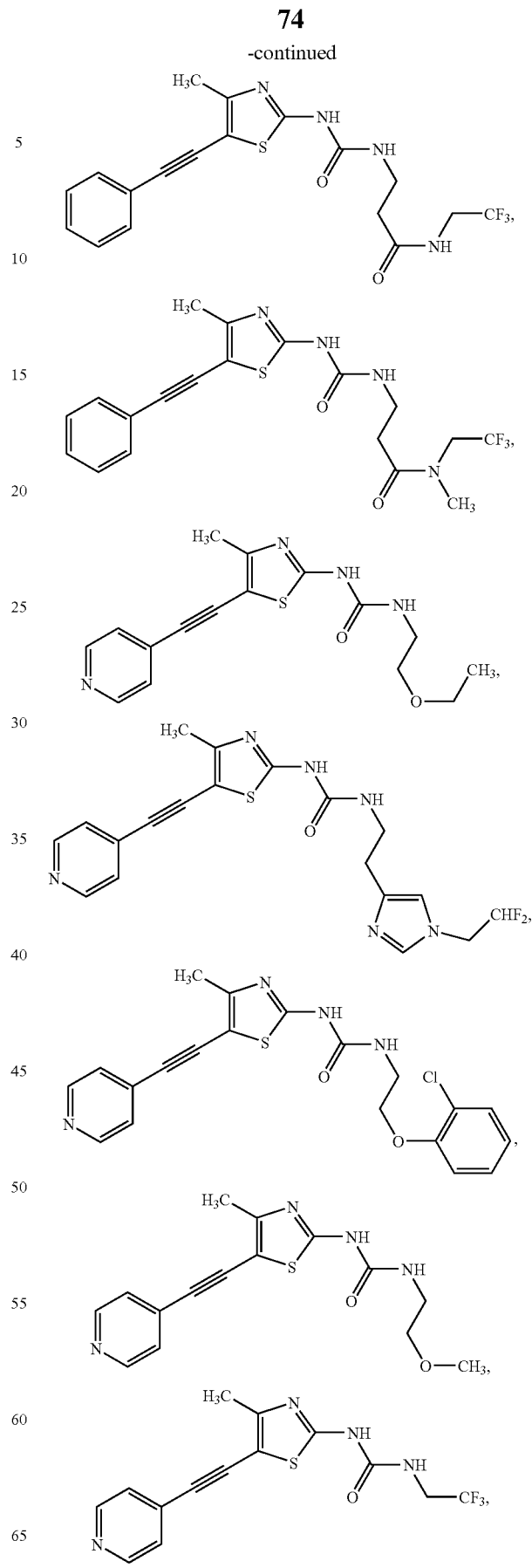

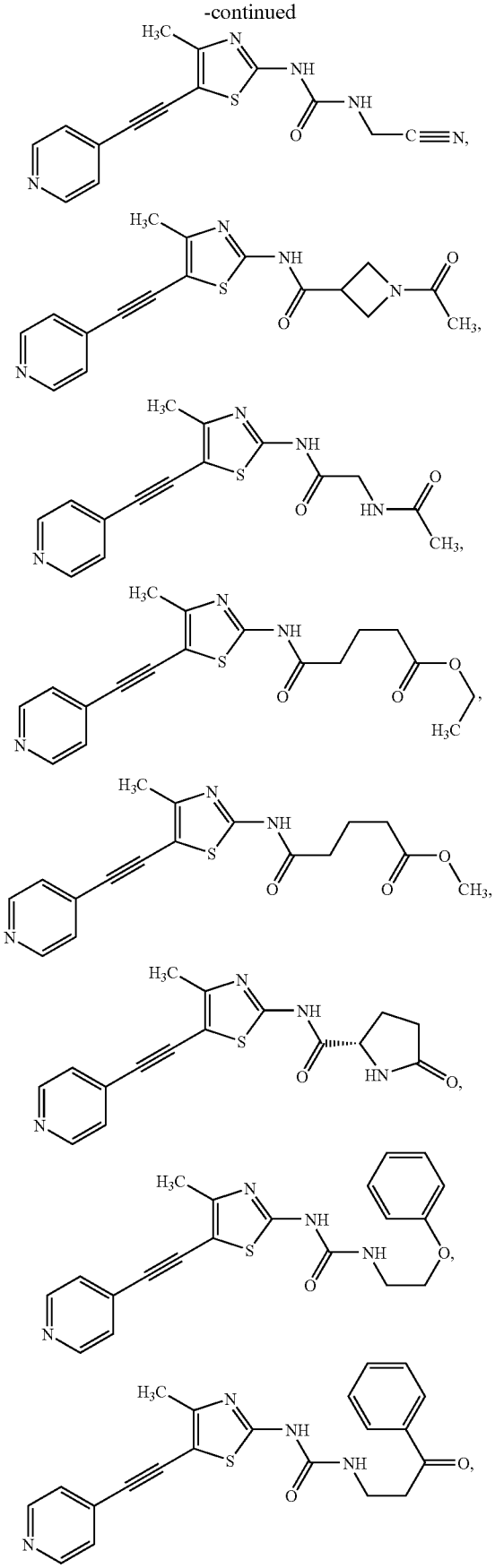
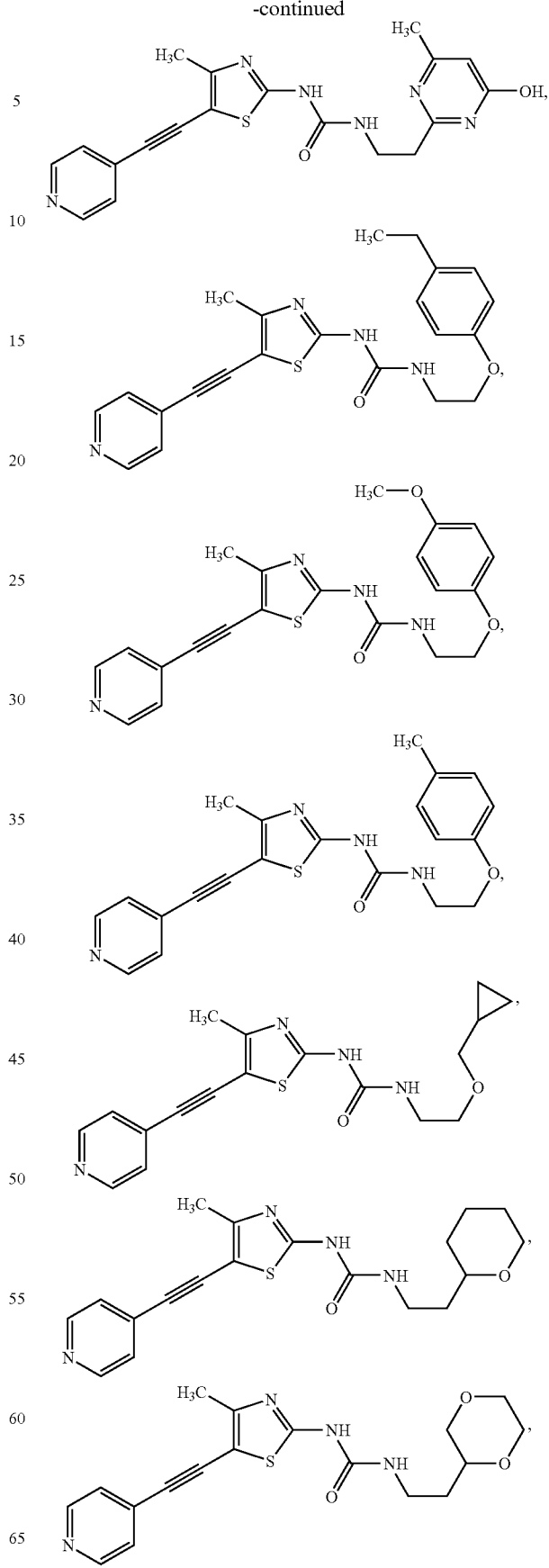

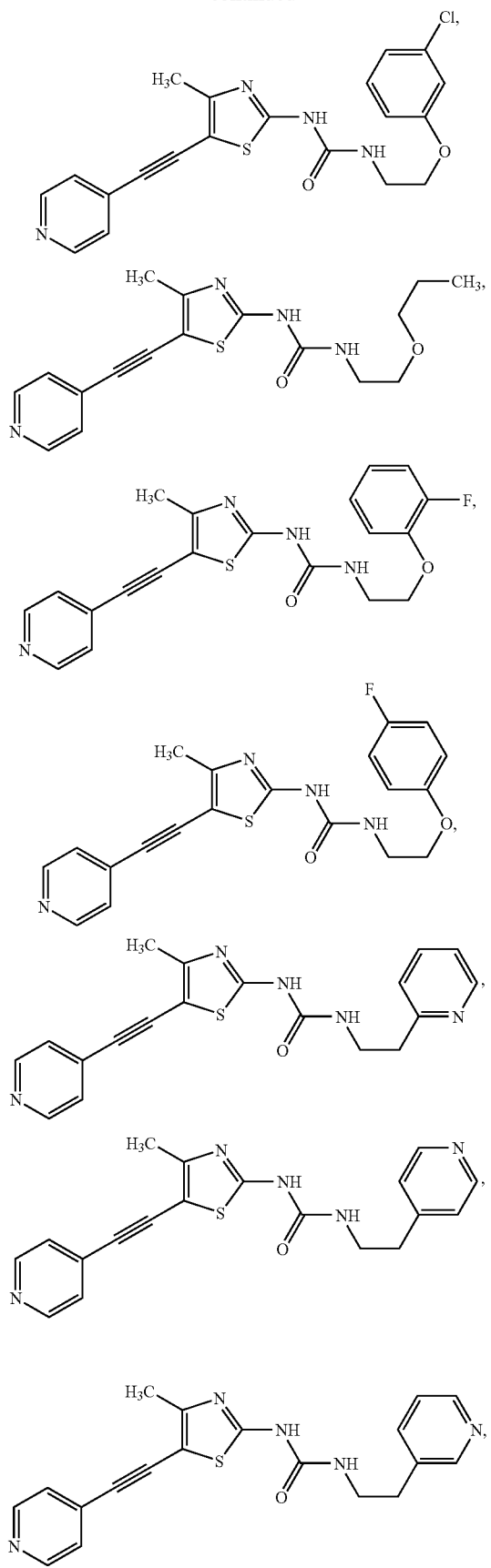
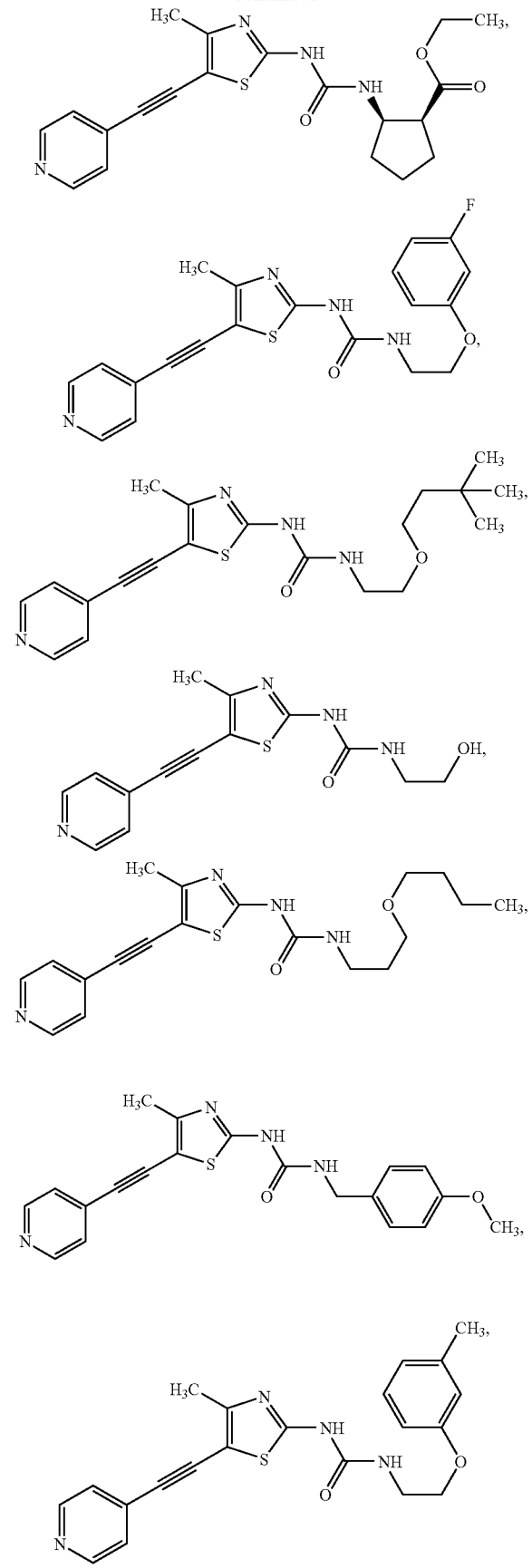

-continued

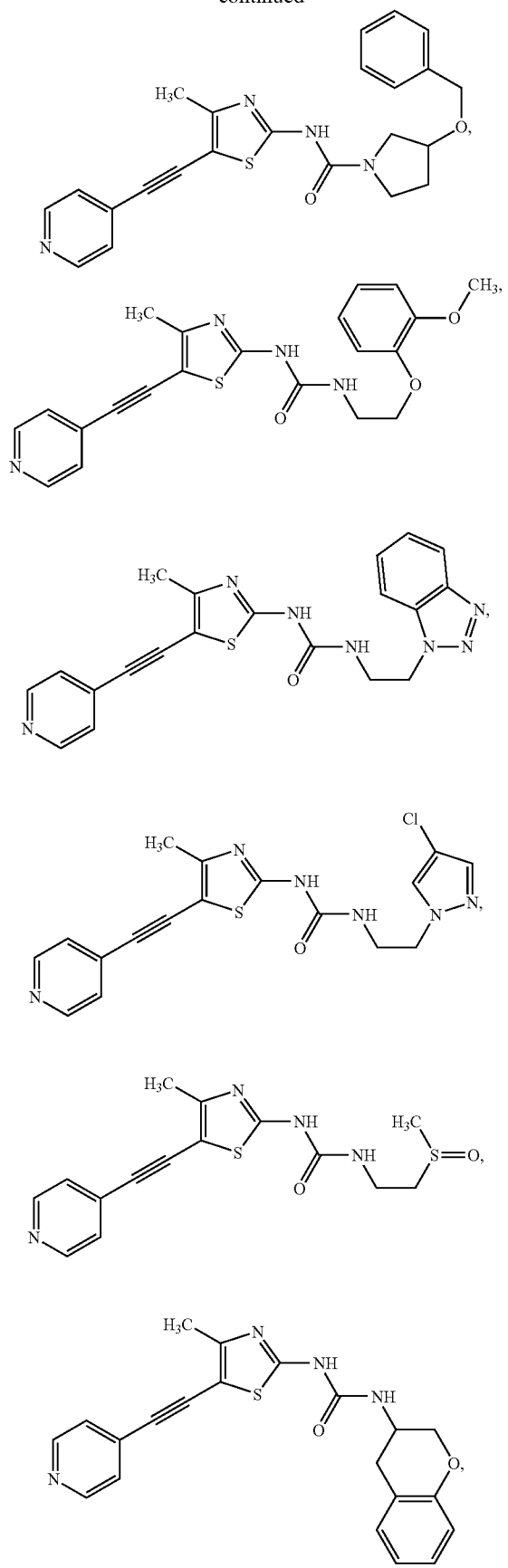
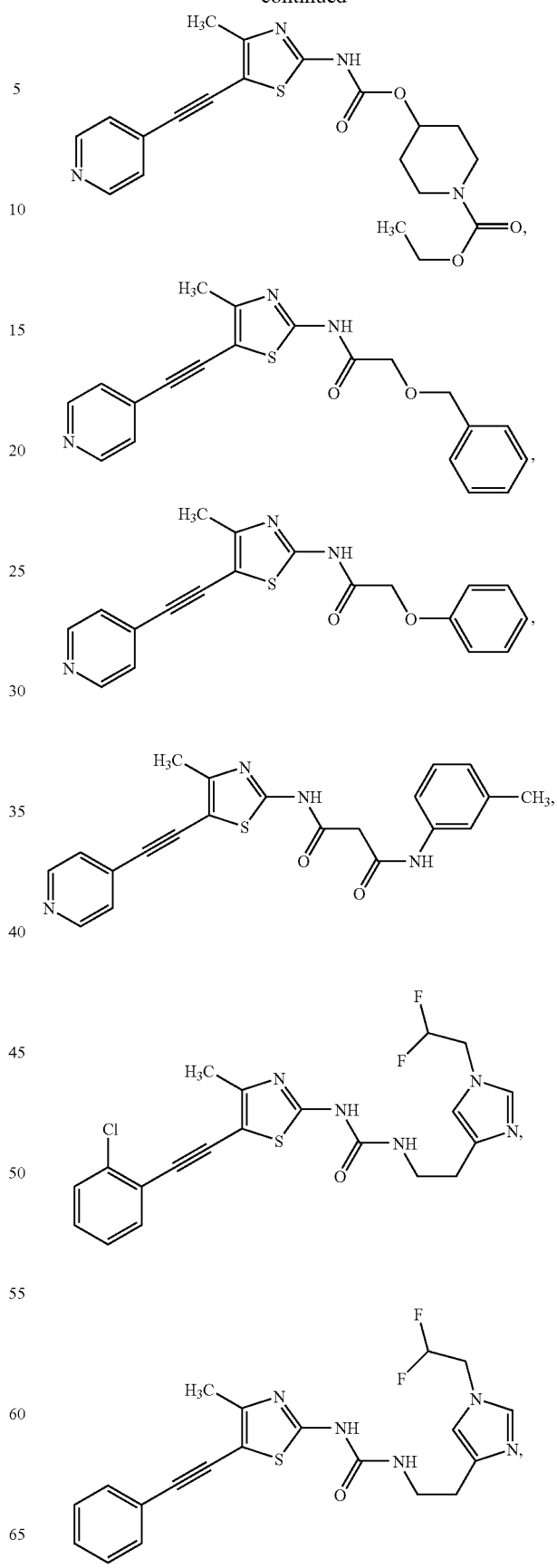

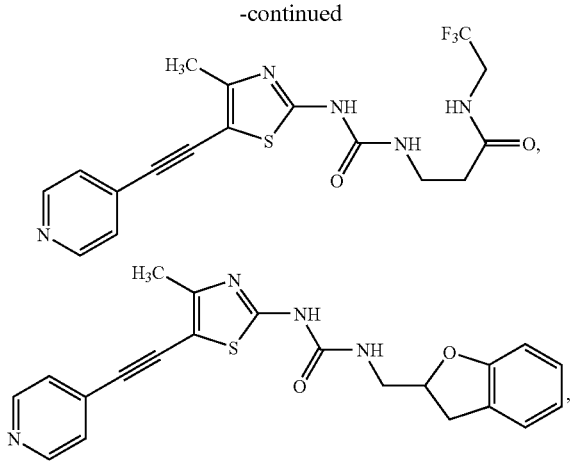
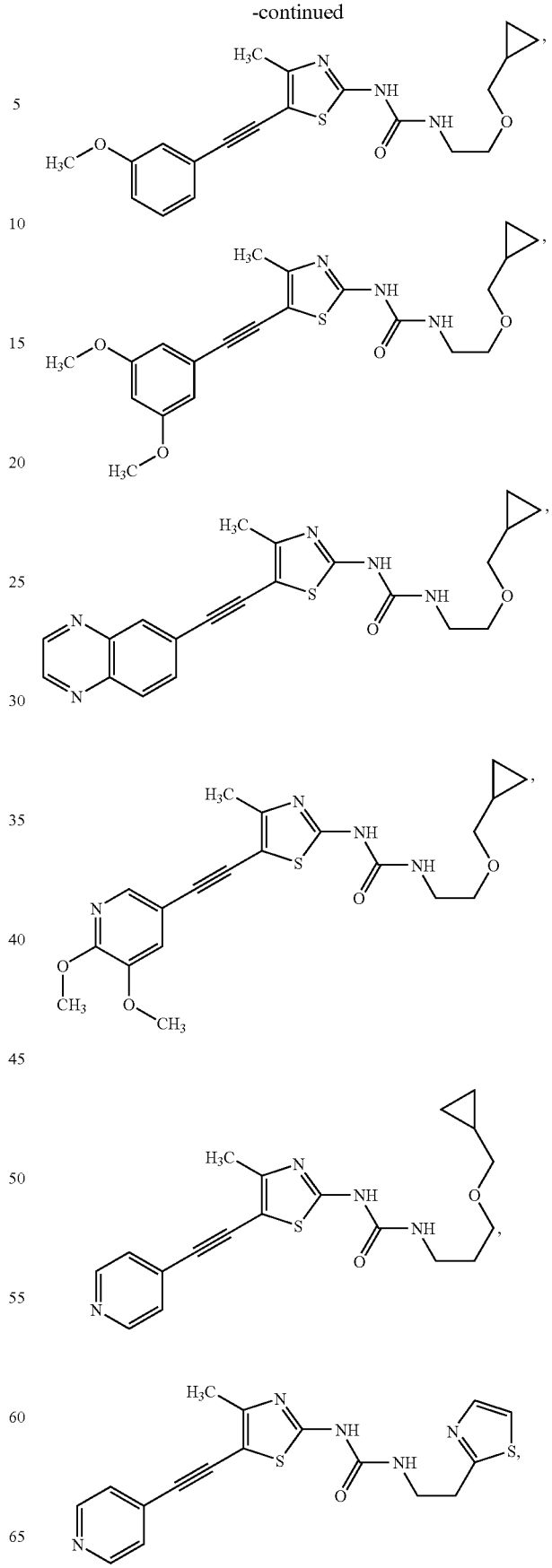

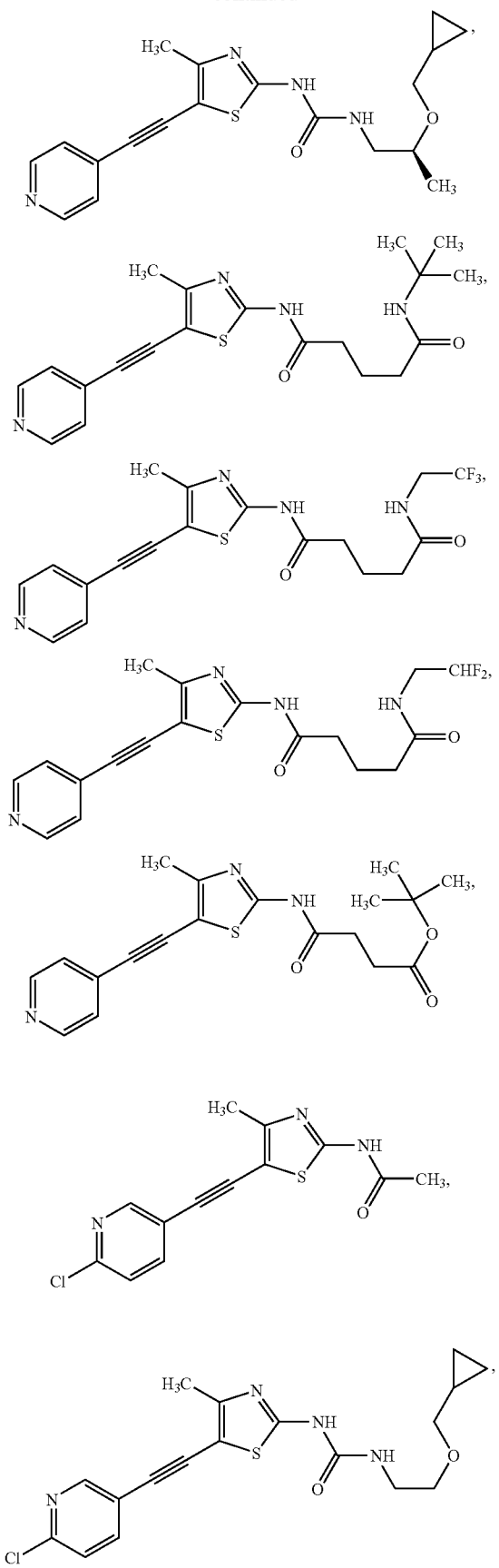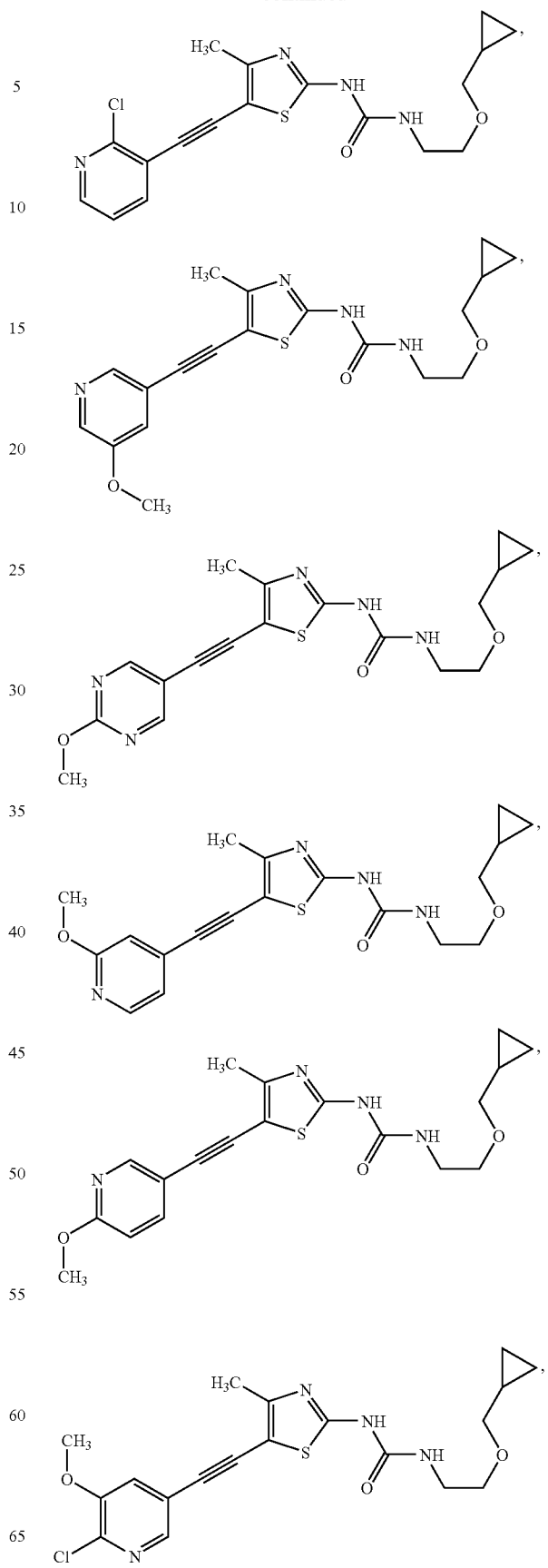

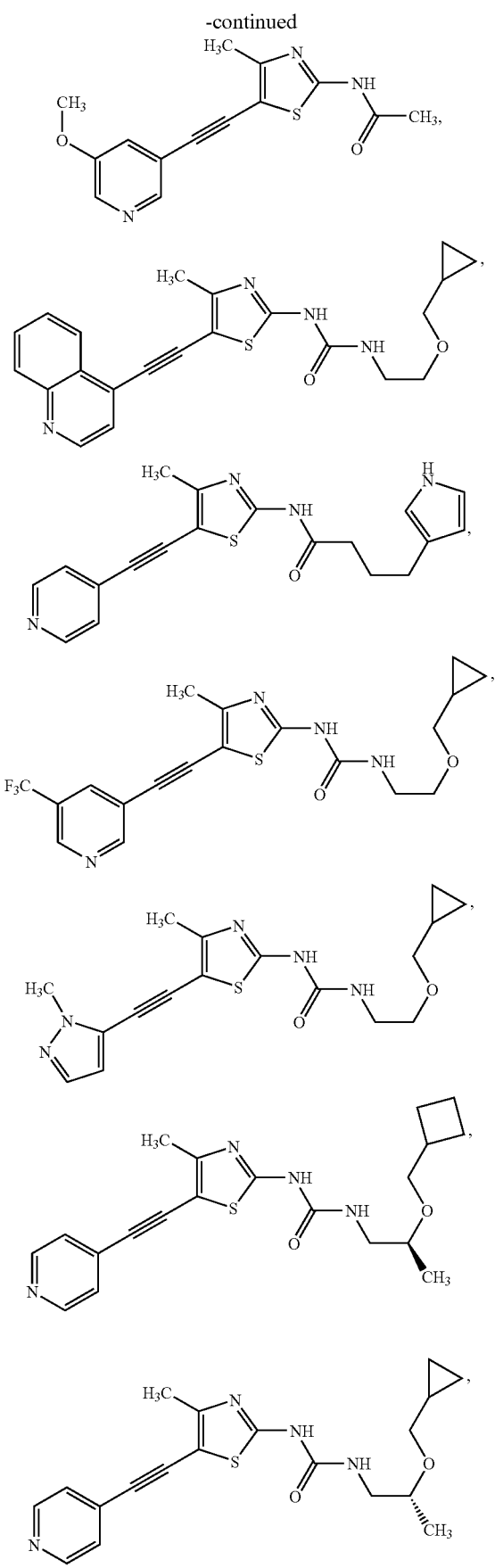
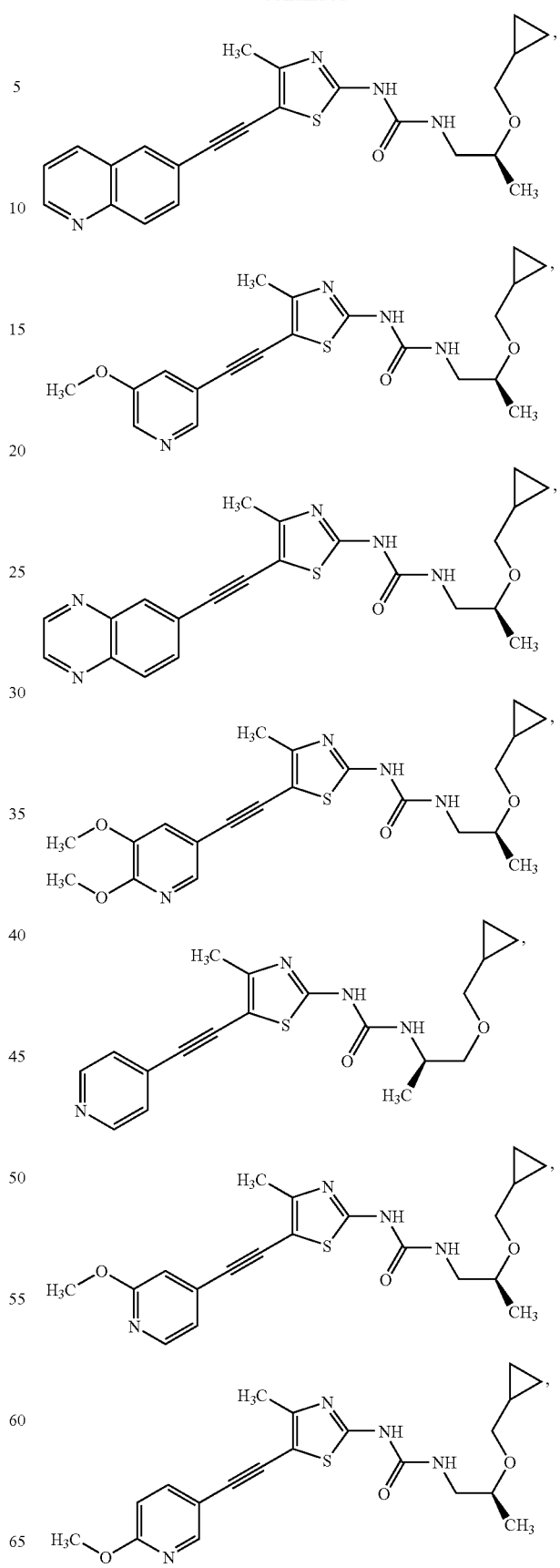

89
-continued
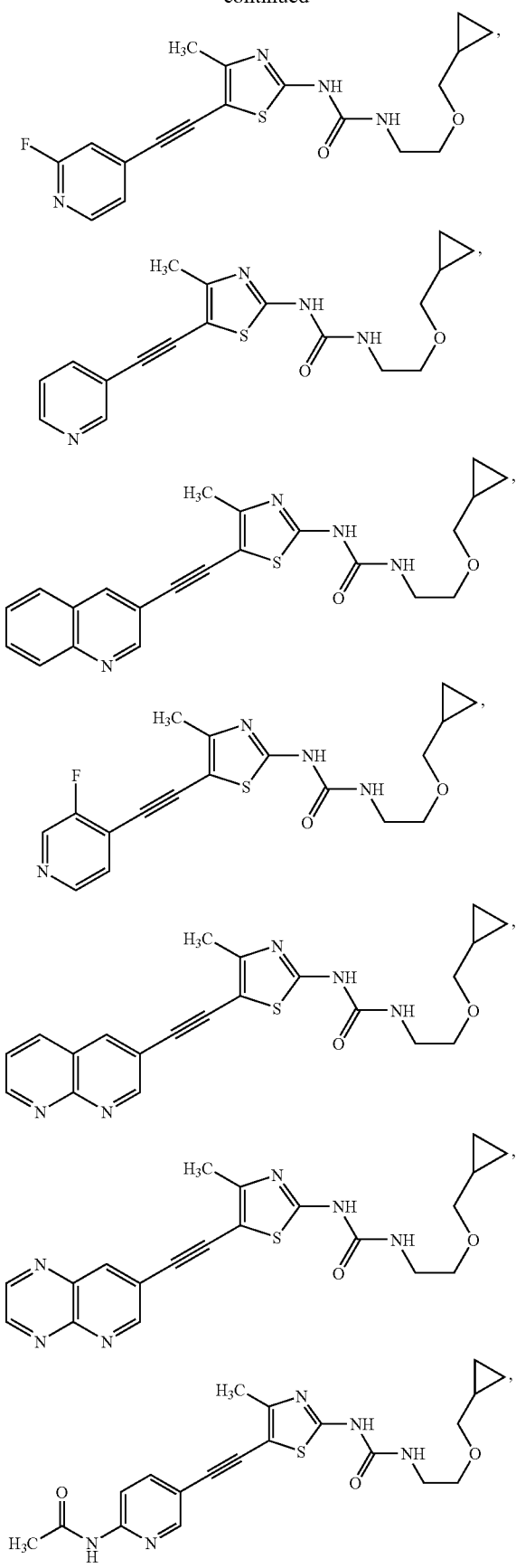
90
-continued
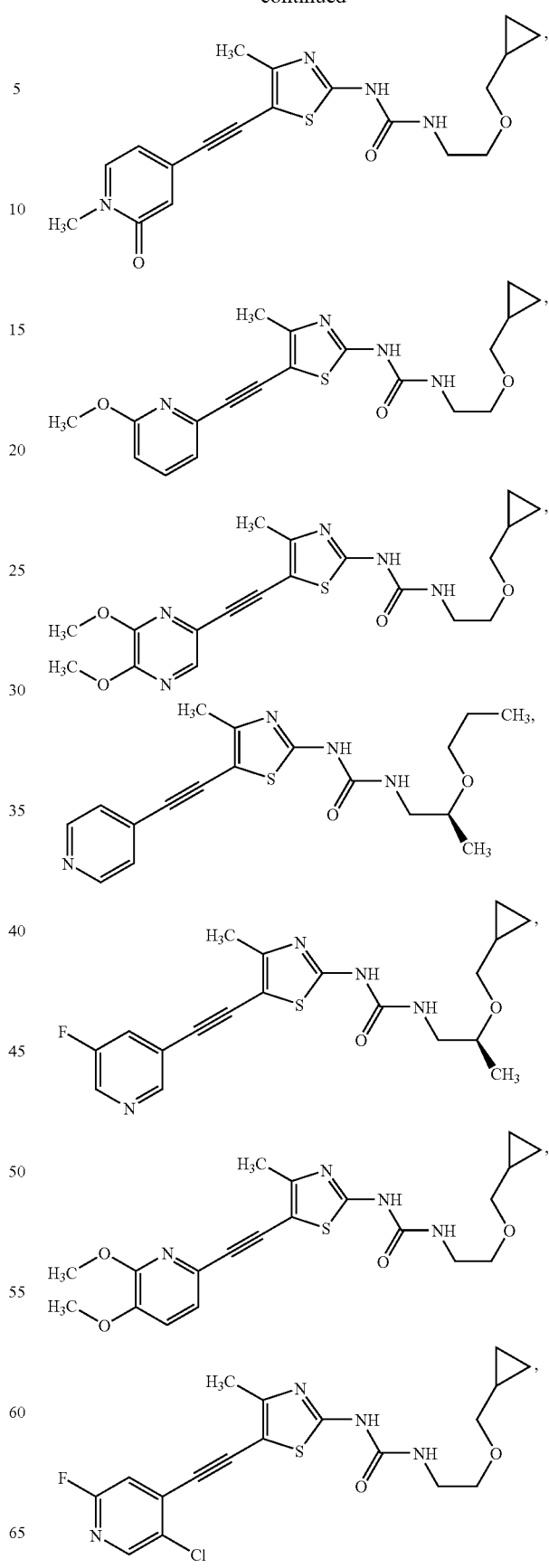

91
-continued
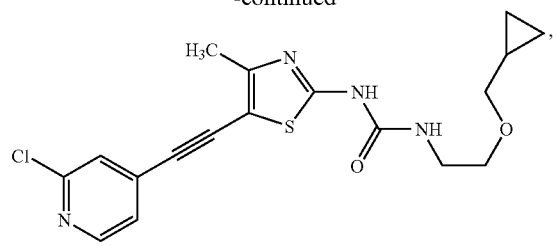
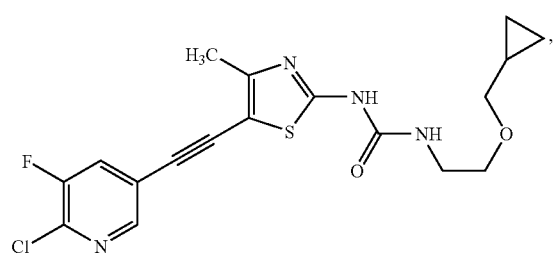
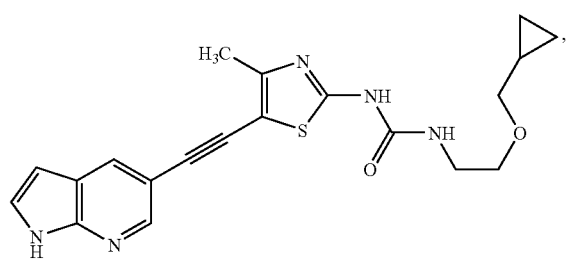
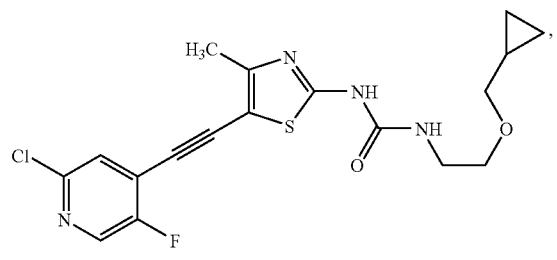
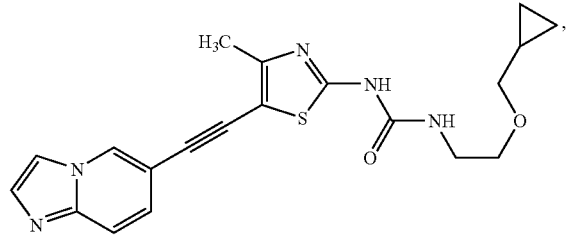
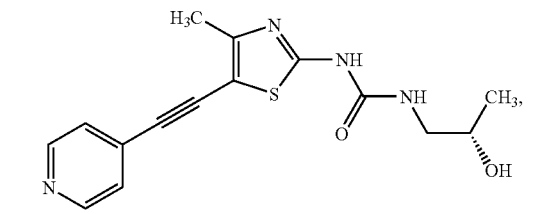
92
-continued
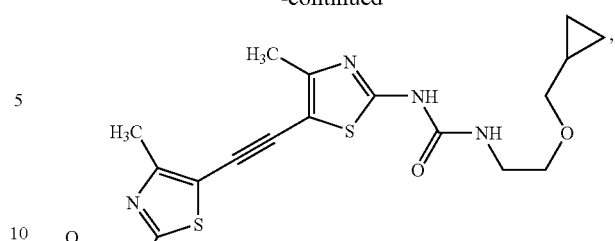
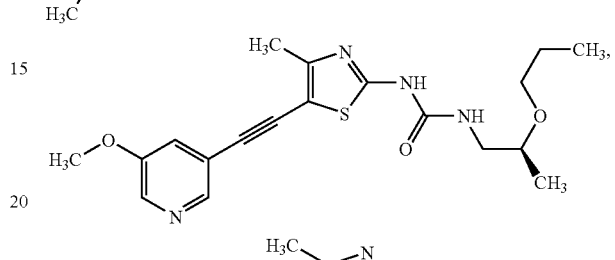
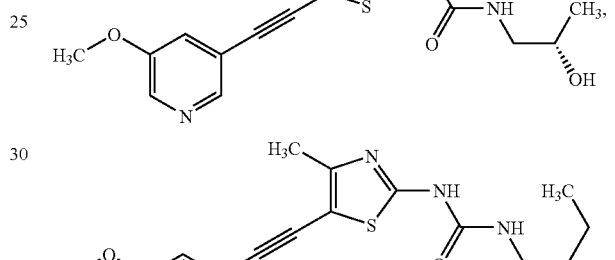
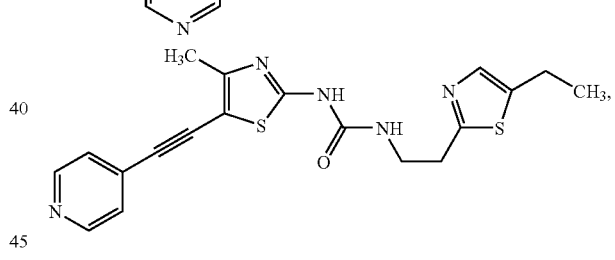
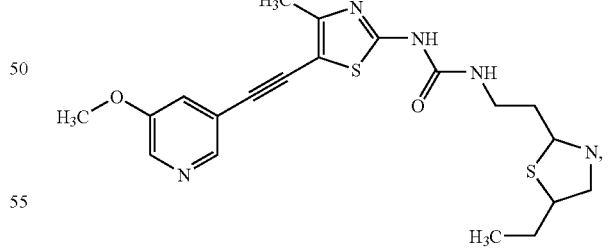
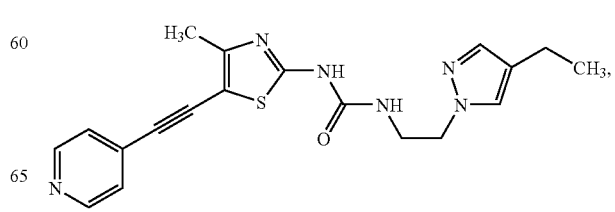

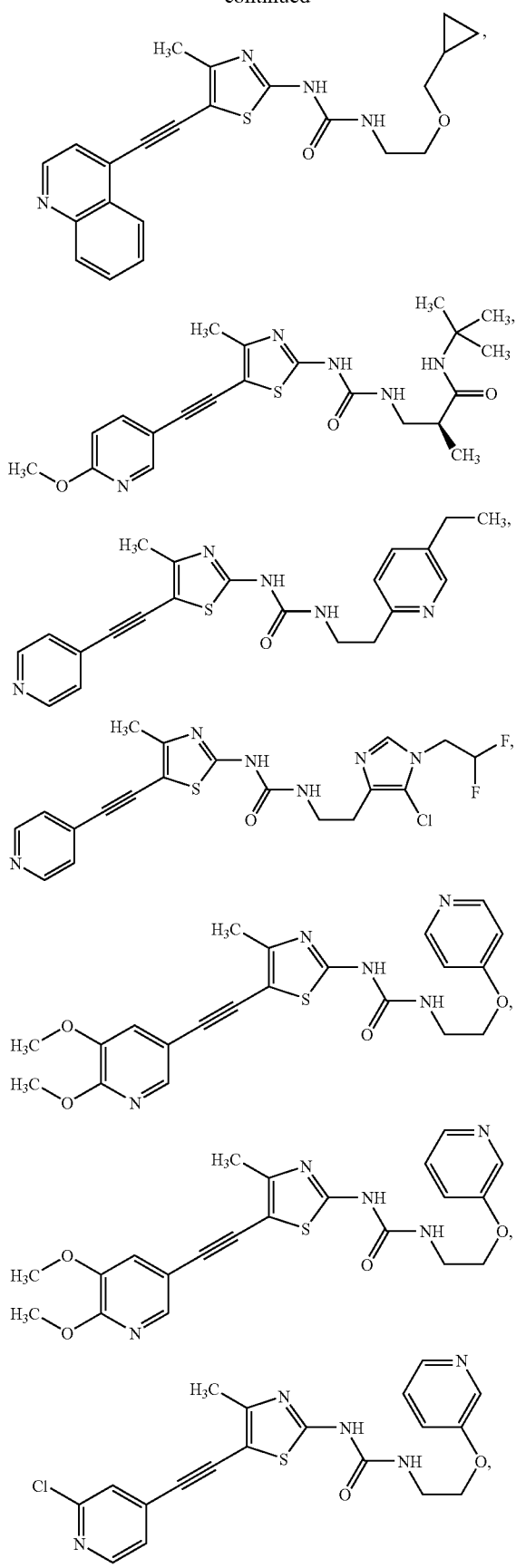
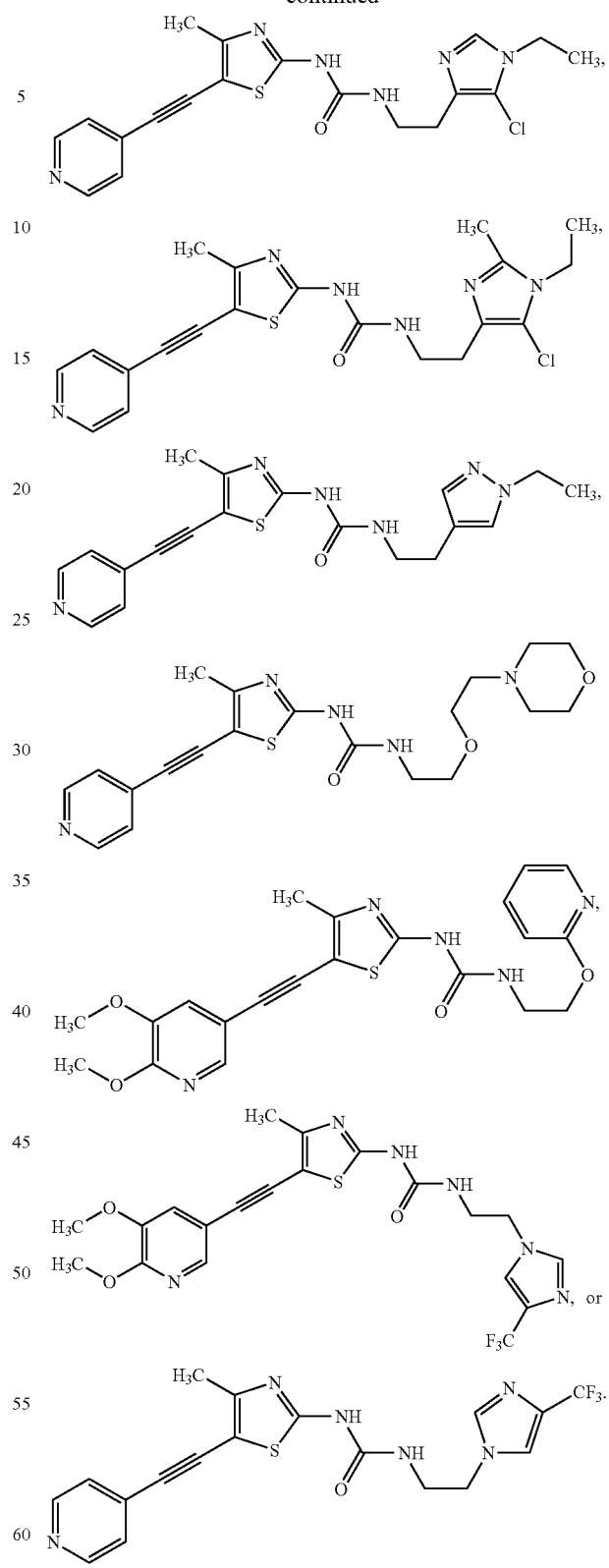
14. A pharmaceutical composition comprising a compound according to claim 1 and a pharmaceutically acceptable carrier, adjuvant, or vehicle.

15. The composition according to claim 14, additionally comprising a therapeutic agent selected from an agent for treating multiple sclerosis, an anti-inflammatory agent, an immunomodulatory agent, or an immunosuppressive agent.

16. The composition according to claim 15, wherein said therapeutic agent is beta interferon, glatiramir, natalizumab, or mitoxantrone.

* * * * *